United States Patent
Widenhouse et al.

(10) Patent No.: US 10,987,094 B2
(45) Date of Patent: Apr. 27, 2021

(54) SURGICAL BOWEL RETRACTOR DEVICES

(71) Applicant: Ethicon LLC, Guaynabo, PR (US)

(72) Inventors: Tamara S. Widenhouse, Clarksville, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 0 days.

(21) Appl. No.: 16/150,589

(22) Filed: Oct. 3, 2018

(65) Prior Publication Data

US 2019/0029661 A1 Jan. 31, 2019

Related U.S. Application Data

(63) Continuation of application No. 14/788,923, filed on Jul. 1, 2015, now Pat. No. 10,130,352, which is a
(Continued)

(51) Int. Cl.
*A61B 17/02* (2006.01)
*A61B 17/068* (2006.01)
(Continued)

(52) U.S. Cl.
CPC .... *A61B 17/0293* (2013.01); *A61B 17/00234* (2013.01); *A61B 17/0218* (2013.01);
(Continued)

(58) Field of Classification Search
CPC ............ A61B 17/0293; A61B 17/0206; A61B 17/0218; A61B 17/0231;
(Continued)

(56) References Cited

U.S. PATENT DOCUMENTS

| 357,351 A | * | 2/1887 | Welliver | ............... B43K 23/001 24/10 R |
| 768,658 A | * | 8/1904 | Dongille | .................. A45D 8/34 132/133 |

(Continued)

FOREIGN PATENT DOCUMENTS

| AU | 2012200178 B2 | 7/2013 |
| CA | 2795323 A1 | 5/2014 |

(Continued)

OTHER PUBLICATIONS

Disclosed Anonymously, "Motor-Driven Surgical Stapler Improvements," Research Disclosure Database No. 526041, Published: Feb. 2008.
(Continued)

*Primary Examiner* — Eduardo C Robert
*Assistant Examiner* — Steven J Cotroneo

(57) ABSTRACT

A bowel retractor device comprising a flexible endless collar member, a plurality of discrete first flexible fingers, and a plurality of discrete second flexible fingers is disclosed. The flexible endless collar member comprises an inner wall that defines a central open area. The plurality of discrete first flexible fingers protrude from a first portion of the inner wall. The discrete first flexible fingers are spaced from each other to define a first space therebetween. The plurality of discrete second flexible fingers protrude from a second portion of the inner wall that faces the first portion of the inner wall. Each discrete second flexible finger comprises a second end that extends into a corresponding first space. At least one of the discrete first flexible fingers and at least one of the discrete second flexible fingers each comprise a ball-shaped feature formed on an end thereof.

14 Claims, 22 Drawing Sheets

Related U.S. Application Data continuation of application No. 13/181,827, filed on Jul. 13, 2011, now Pat. No. 9,089,330.

(51) Int. Cl.
| | |
|---|---|
| *A61B 17/072* | (2006.01) |
| *A61B 17/115* | (2006.01) |
| *A61B 17/00* | (2006.01) |
| *A61B 17/34* | (2006.01) |

(52) U.S. Cl.
CPC .......... *A61B 17/068* (2013.01); *A61B 17/072* (2013.01); *A61B 17/07207* (2013.01); *A61B 17/1155* (2013.01); *A61B 17/3417* (2013.01); *A61B 2017/00287* (2013.01); *A61B 2017/00353* (2013.01); *A61B 2017/00477* (2013.01); *A61B 2017/0225* (2013.01); *A61B 2017/0287* (2013.01); *A61B 2017/07257* (2013.01); *A61B 2560/0443* (2013.01); *F04C 2270/0421* (2013.01)

(58) Field of Classification Search
CPC ..... A61B 17/0281–0293; A61B 17/132–1355; Y10T 24/44923; Y10T 24/44769; Y10T 24/44915; Y10T 24/15; Y10T 24/155; Y10T 24/23; Y10T 24/44222; Y10T 24/44231; Y10T 24/44641; Y10T 24/44983; F16B 2/20; F16B 2/22; A41F 1/00; A45D 8/34; A45D 8/36; A45D 2008/345; B65D 33/1625
USPC ....................................................... 600/235
See application file for complete search history.

(56) References Cited

U.S. PATENT DOCUMENTS

| | | | | |
|---|---|---|---|---|
| 811,742 | A | * | 2/1906 | Petrie .................... B65D 23/065 215/392 |
| 971,519 | A | * | 10/1910 | Brannen .................... A45D 8/34 132/107 |
| 2,224,882 | A | | 12/1940 | Peck |
| 2,445,071 | A | * | 7/1948 | Kovacs .................... A45D 8/34 132/133 |
| 2,457,274 | A | * | 12/1948 | Rifken .................... A47K 10/14 248/314 |
| 2,547,295 | A | * | 4/1951 | Weeks .................... A45D 8/36 132/273 |
| 2,718,894 | A | * | 9/1955 | Gresham .................... A45D 8/34 132/133 |
| 2,742,955 | A | | 4/1956 | Dominguez |
| D180,713 | S | * | 7/1957 | Hammond ..................... D28/23 |
| 2,853,074 | A | | 9/1958 | Olson |
| 2,975,788 | A | * | 3/1961 | Ardelyan .................... A45D 8/34 132/273 |
| 3,080,564 | A | | 3/1963 | Strekopitov et al. |
| 3,096,960 | A | * | 7/1963 | Kinney .................... A47L 13/512 248/113 |
| 3,166,072 | A | | 1/1965 | Sullivan, Jr. |
| 3,170,213 | A | * | 2/1965 | Thomas, Jr. ............. A44B 11/04 24/571 |
| 3,266,494 | A | | 8/1966 | Brownrigg et al. |
| 3,348,595 | A | * | 10/1967 | Stevens, Jr. ......... B65D 33/1625 206/525 |
| 3,357,070 | A | * | 12/1967 | Soloan .................... A45D 8/34 24/562 |
| 3,359,978 | A | | 12/1967 | Smith, Jr. |
| 3,490,675 | A | | 1/1970 | Green et al. |
| 3,494,533 | A | | 2/1970 | Green et al. |
| 3,551,987 | A | | 1/1971 | Wilkinson |
| 3,643,851 | A | | 2/1972 | Green et al. |
| 3,662,939 | A | | 5/1972 | Bryan |
| 3,717,294 | A | | 2/1973 | Green |
| 3,744,495 | A | | 7/1973 | Johnson |
| 3,746,002 | A | | 7/1973 | Haller |
| 3,819,100 | A | | 6/1974 | Noiles et al. |
| 3,863,639 | A | | 2/1975 | Kleaveland |
| 3,918,920 | A | * | 11/1975 | Barber ...................... B01L 9/06 422/560 |
| 3,962,757 | A | * | 6/1976 | Gedney ................ A47C 21/022 24/562 |
| RE28,932 | E | | 8/1976 | Noiles et al. |
| 4,111,206 | A | | 9/1978 | Vishnevsky et al. |
| 4,138,055 | A | * | 2/1979 | Harrison ................ B42D 17/00 232/1 C |
| 4,190,042 | A | | 2/1980 | Sinnreich |
| 4,198,982 | A | | 4/1980 | Fortner et al. |
| 4,203,180 | A | * | 5/1980 | Striplin .................. B65D 67/00 206/526 |
| 4,207,898 | A | | 6/1980 | Becht |
| 4,267,995 | A | * | 5/1981 | McMillan ................ H02G 3/32 174/153 G |
| 4,272,002 | A | | 6/1981 | Moshofsky |
| 4,274,398 | A | * | 6/1981 | Scott, Jr. ............ A61B 17/0293 600/233 |
| 4,289,133 | A | | 9/1981 | Rothfuss |
| 4,304,236 | A | | 12/1981 | Conta et al. |
| 4,305,539 | A | | 12/1981 | Korolkov et al. |
| 4,331,277 | A | | 5/1982 | Green |
| D265,877 | S | * | 8/1982 | Hardy ......................... 84/422.4 |
| 4,379,457 | A | | 4/1983 | Gravener et al. |
| 4,383,634 | A | | 5/1983 | Green |
| 4,396,139 | A | | 8/1983 | Hall et al. |
| 4,397,311 | A | | 8/1983 | Kanshin et al. |
| 4,402,445 | A | | 9/1983 | Green |
| 4,408,692 | A | | 10/1983 | Sigel et al. |
| 4,415,112 | A | | 11/1983 | Green |
| 4,417,890 | A | | 11/1983 | Dennehey et al. |
| 4,429,695 | A | | 2/1984 | Green |
| 4,434,796 | A | | 3/1984 | Karapetian et al. |
| 4,438,659 | A | | 3/1984 | Desplats |
| 4,439,884 | A | * | 4/1984 | Giorni ...................... B08B 1/00 15/104.04 |
| 4,470,180 | A | * | 9/1984 | Blomgren ................ F16B 2/22 206/306 |
| 4,473,077 | A | | 9/1984 | Noiles et al. |
| 4,475,679 | A | | 10/1984 | Fleury, Jr. |
| 4,483,455 | A | * | 11/1984 | Prophet, Jr. ............ A47G 23/06 220/23.83 |
| 4,489,875 | A | | 12/1984 | Crawford et al. |
| 4,500,024 | A | | 2/1985 | DiGiovanni et al. |
| 4,505,272 | A | | 3/1985 | Utyamyshev et al. |
| 4,505,273 | A | | 3/1985 | Braun et al. |
| 4,505,414 | A | | 3/1985 | Filipi |
| 4,506,671 | A | | 3/1985 | Green |
| 4,520,817 | A | | 6/1985 | Green |
| 4,522,327 | A | | 6/1985 | Korthoff et al. |
| 4,527,724 | A | | 7/1985 | Chow et al. |
| 4,530,453 | A | | 7/1985 | Green |
| 4,566,620 | A | | 1/1986 | Green et al. |
| 4,573,468 | A | | 3/1986 | Conta et al. |
| 4,573,622 | A | | 3/1986 | Green et al. |
| 4,576,167 | A | | 3/1986 | Noiles |
| 4,580,712 | A | | 4/1986 | Green |
| 4,585,153 | A | | 4/1986 | Failla et al. |
| 4,605,001 | A | | 8/1986 | Rothfuss et al. |
| 4,605,004 | A | | 8/1986 | Di Giovanni et al. |
| 4,608,981 | A | | 9/1986 | Rothfuss et al. |
| 4,610,383 | A | | 9/1986 | Rothfuss et al. |
| 4,612,933 | A | | 9/1986 | Brinkerhoff et al. |
| 4,619,262 | A | | 10/1986 | Taylor |
| 4,619,391 | A | | 10/1986 | Sharkany et al. |
| 4,629,107 | A | | 12/1986 | Fedotov et al. |
| 4,631,783 | A | * | 12/1986 | Hayashi ................ F16M 13/00 211/70.6 |
| 4,632,290 | A | | 12/1986 | Green et al. |
| 4,633,874 | A | | 1/1987 | Chow et al. |
| 4,634,419 | A | | 1/1987 | Kreizman et al. |
| 4,644,610 | A | * | 2/1987 | Fish ...................... A01G 13/04 211/70.6 |
| 4,652,820 | A | | 3/1987 | Maresca |

(56) References Cited

U.S. PATENT DOCUMENTS

| | | | |
|---|---|---|---|
| 4,654,028 A | 3/1987 | Suma | |
| 4,655,222 A | 4/1987 | Florez et al. | |
| 4,662,555 A | 5/1987 | Thornton | |
| 4,664,305 A | 5/1987 | Blake, III et al. | |
| 4,669,647 A | 6/1987 | Storace | |
| 4,671,445 A | 6/1987 | Barker et al. | |
| 4,684,051 A | 8/1987 | Akopov et al. | |
| 4,697,312 A * | 10/1987 | Freyer | B65D 33/1625 24/30.5 R |
| 4,700,703 A | 10/1987 | Resnick et al. | |
| 4,715,520 A | 12/1987 | Roehr, Jr. et al. | |
| 4,719,917 A | 1/1988 | Barrows et al. | |
| 4,727,308 A | 2/1988 | Huljak et al. | |
| 4,728,020 A | 3/1988 | Green et al. | |
| 4,744,363 A | 5/1988 | Hasson | |
| 4,747,820 A | 5/1988 | Hornlein et al. | |
| 4,750,902 A | 6/1988 | Wuchinich et al. | |
| 4,752,024 A | 6/1988 | Green et al. | |
| 4,754,909 A | 7/1988 | Barker et al. | |
| 4,767,044 A | 8/1988 | Green | |
| 4,773,420 A | 9/1988 | Green | |
| 4,805,823 A | 2/1989 | Rothfuss | |
| 4,809,695 A | 3/1989 | Gwathmey et al. | |
| 4,817,847 A | 4/1989 | Redtenbacher et al. | |
| 4,818,121 A * | 4/1989 | Volk | B65D 33/1633 294/137 |
| 4,819,853 A | 4/1989 | Green | |
| 4,821,939 A | 4/1989 | Green | |
| 4,827,911 A | 5/1989 | Broadwin et al. | |
| 4,844,068 A | 7/1989 | Arata et al. | |
| 4,848,637 A | 7/1989 | Pruitt | |
| 4,865,030 A | 9/1989 | Polyak | |
| 4,869,414 A | 9/1989 | Green et al. | |
| 4,869,415 A | 9/1989 | Fox | |
| 4,873,977 A | 10/1989 | Avant et al. | |
| 4,892,244 A | 1/1990 | Fox et al. | |
| 4,893,622 A | 1/1990 | Green et al. | |
| 4,896,678 A | 1/1990 | Ogawa | |
| 4,903,697 A | 2/1990 | Resnick et al. | |
| 4,909,789 A | 3/1990 | Taguchi et al. | |
| 4,914,789 A * | 4/1990 | Pedersen | B65D 33/1625 24/30.5 S |
| 4,921,479 A | 5/1990 | Grayzel | |
| 4,930,674 A | 6/1990 | Barak | |
| 4,931,047 A | 6/1990 | Broadwin et al. | |
| 4,938,408 A | 7/1990 | Bedi et al. | |
| 4,941,623 A | 7/1990 | Pruitt | |
| 4,944,443 A | 7/1990 | Oddsen et al. | |
| 4,973,302 A | 11/1990 | Armour et al. | |
| 4,978,333 A | 12/1990 | Broadwin et al. | |
| 4,984,564 A | 1/1991 | Yuen | |
| 4,986,808 A | 1/1991 | Broadwin et al. | |
| 5,002,553 A | 3/1991 | Shiber | |
| 5,014,899 A | 5/1991 | Presty et al. | |
| 5,015,227 A | 5/1991 | Broadwin et al. | |
| 5,016,575 A * | 5/1991 | Gordon | A01K 27/005 119/792 |
| 5,027,834 A | 7/1991 | Pruitt | |
| 5,038,109 A | 8/1991 | Goble et al. | |
| D319,903 S * | 9/1991 | Barner | D32/61 |
| 5,065,929 A | 11/1991 | Schulze et al. | |
| 5,071,430 A | 12/1991 | de Salis et al. | |
| 5,074,454 A | 12/1991 | Peters | |
| 5,080,088 A | 1/1992 | LeVahn | |
| 5,082,005 A | 1/1992 | Kaldany | |
| 5,084,057 A | 1/1992 | Green et al. | |
| 5,088,997 A | 2/1992 | Delahuerga et al. | |
| 5,098,360 A | 3/1992 | Hirota | |
| 5,104,025 A | 4/1992 | Main et al. | |
| 5,104,397 A | 4/1992 | Vasconcelos et al. | |
| 5,108,368 A | 4/1992 | Hammerslag et al. | |
| 5,116,349 A | 5/1992 | Aranyi | |
| 5,119,983 A | 6/1992 | Green et al. | |
| 5,122,156 A | 6/1992 | Granger et al. | |
| 5,129,570 A | 7/1992 | Schulze et al. | |
| 5,137,198 A | 8/1992 | Nobis et al. | |
| 5,139,513 A | 8/1992 | Segato | |
| 5,141,144 A | 8/1992 | Foslien et al. | |
| 5,156,315 A | 10/1992 | Green et al. | |
| 5,156,609 A | 10/1992 | Nakao et al. | |
| 5,158,567 A | 10/1992 | Green | |
| 5,170,925 A | 12/1992 | Madden et al. | |
| 5,171,247 A | 12/1992 | Hughett et al. | |
| 5,171,249 A | 12/1992 | Stefanchik et al. | |
| 5,190,517 A | 3/1993 | Zieve et al. | |
| 5,195,505 A | 3/1993 | Josefsen | |
| 5,197,649 A | 3/1993 | Bessler et al. | |
| 5,205,459 A | 4/1993 | Brinkerhoff et al. | |
| 5,211,649 A | 5/1993 | Kohler et al. | |
| 5,211,655 A | 5/1993 | Hasson | |
| 5,221,036 A | 6/1993 | Takase | |
| 5,221,281 A | 6/1993 | Klicek | |
| 5,222,945 A | 6/1993 | Basnight | |
| 5,222,963 A | 6/1993 | Brinkerhoff et al. | |
| 5,222,975 A | 6/1993 | Crainich | |
| 5,234,447 A | 8/1993 | Kaster et al. | |
| 5,236,440 A | 8/1993 | Hlavacek | |
| 5,239,981 A | 8/1993 | Anapliotis | |
| 5,240,163 A | 8/1993 | Stein et al. | |
| 5,258,009 A | 11/1993 | Conners | |
| 5,258,012 A | 11/1993 | Luscombe et al. | |
| 5,263,629 A | 11/1993 | Trumbull et al. | |
| 5,263,937 A | 11/1993 | Shipp | |
| 5,271,543 A | 12/1993 | Grant et al. | |
| 5,275,322 A | 1/1994 | Brinkerhoff et al. | |
| 5,281,216 A | 1/1994 | Klicek | |
| 5,282,806 A | 2/1994 | Haber et al. | |
| 5,282,829 A | 2/1994 | Hermes | |
| 5,284,128 A | 2/1994 | Hart | |
| 5,285,945 A | 2/1994 | Brinkerhoff et al. | |
| 5,304,204 A | 4/1994 | Bregen | |
| 5,309,896 A * | 5/1994 | Moll | A61B 17/00234 128/898 |
| 5,309,927 A | 5/1994 | Welch | |
| 5,312,023 A | 5/1994 | Green et al. | |
| 5,312,329 A | 5/1994 | Beaty et al. | |
| 5,314,445 A | 5/1994 | Heidmueller et al. | |
| 5,330,502 A | 7/1994 | Hassler et al. | |
| 5,333,772 A | 8/1994 | Rothfuss et al. | |
| 5,333,773 A | 8/1994 | Main et al. | |
| 5,336,232 A | 8/1994 | Green et al. | |
| 5,342,385 A | 8/1994 | Norelli et al. | |
| 5,342,395 A | 8/1994 | Jarrett et al. | |
| 5,342,396 A | 8/1994 | Cook | |
| 5,346,115 A | 9/1994 | Perouse et al. | |
| 5,346,504 A | 9/1994 | Ortiz et al. | |
| 5,350,104 A | 9/1994 | Main et al. | |
| 5,350,400 A | 9/1994 | Esposito et al. | |
| 5,354,250 A | 10/1994 | Christensen | |
| 5,354,303 A | 10/1994 | Spaeth et al. | |
| 5,358,506 A | 10/1994 | Green et al. | |
| 5,364,001 A | 11/1994 | Bryan | |
| 5,366,134 A | 11/1994 | Green et al. | |
| 5,366,479 A | 11/1994 | McGarry et al. | |
| 5,370,645 A | 12/1994 | Klicek et al. | |
| 5,372,596 A | 12/1994 | Klicek et al. | |
| 5,374,277 A | 12/1994 | Hassler | |
| 5,375,588 A | 12/1994 | Yoon | |
| 5,381,588 A * | 1/1995 | Nelson | B65D 73/0064 24/30.5 S |
| 5,382,247 A | 1/1995 | Cimino et al. | |
| 5,383,880 A | 1/1995 | Hooven | |
| 5,383,888 A | 1/1995 | Zvenyatsky et al. | |
| 5,383,895 A | 1/1995 | Holmes et al. | |
| 5,389,102 A | 2/1995 | Green et al. | |
| 5,389,104 A | 2/1995 | Hahnen et al. | |
| 5,391,180 A | 2/1995 | Tovey et al. | |
| 5,395,030 A | 3/1995 | Kuramoto et al. | |
| 5,395,033 A | 3/1995 | Byrne et al. | |
| 5,395,384 A | 3/1995 | Duthoit et al. | |
| 5,397,324 A | 3/1995 | Carroll et al. | |
| 5,403,312 A | 4/1995 | Yates et al. | |
| 5,404,870 A | 4/1995 | Brinkerhoff et al. | |
| 5,405,072 A | 4/1995 | Zlock et al. | |

(56) References Cited

U.S. PATENT DOCUMENTS

| | | | |
|---|---|---|---|
| 5,405,073 | A | 4/1995 | Porter |
| 5,405,344 | A | 4/1995 | Williamson et al. |
| 5,405,360 | A | 4/1995 | Tovey |
| 5,411,508 | A | 5/1995 | Bessler et al. |
| 5,413,267 | A | 5/1995 | Solyntjes et al. |
| 5,413,272 | A | 5/1995 | Green et al. |
| 5,413,573 | A | 5/1995 | Koivukangas |
| 5,415,334 | A | 5/1995 | Williamson et al. |
| 5,417,361 | A | 5/1995 | Williamson, IV |
| 5,419,766 | A | 5/1995 | Chang et al. |
| 5,421,829 | A | 6/1995 | Olichney et al. |
| 5,422,567 | A | 6/1995 | Matsunaga |
| 5,423,471 | A | 6/1995 | Mastri et al. |
| 5,423,809 | A | 6/1995 | Klicek |
| 5,425,745 | A | 6/1995 | Green et al. |
| 5,431,668 | A | 7/1995 | Burbank, III et al. |
| 5,433,721 | A | 7/1995 | Hooven et al. |
| 5,438,302 | A | 8/1995 | Goble |
| 5,441,483 | A | 8/1995 | Avitall |
| 5,441,494 | A | 8/1995 | Ortiz |
| 5,445,644 | A | 8/1995 | Pietrafitta et al. |
| 5,447,265 | A | 9/1995 | Vidal et al. |
| 5,447,417 | A | 9/1995 | Kuhl et al. |
| 5,449,355 | A | 9/1995 | Rhum et al. |
| 5,449,365 | A | 9/1995 | Green et al. |
| 5,452,836 | A | 9/1995 | Huitema et al. |
| 5,452,837 | A | 9/1995 | Williamson, IV et al. |
| 5,458,279 | A | 10/1995 | Plyley |
| 5,462,215 | A | 10/1995 | Viola et al. |
| 5,465,819 | A | 11/1995 | Weilant et al. |
| 5,465,894 | A | 11/1995 | Clark et al. |
| 5,465,896 | A | 11/1995 | Allen et al. |
| 5,466,020 | A | 11/1995 | Page et al. |
| 5,470,006 | A | 11/1995 | Rodak |
| 5,470,009 | A | 11/1995 | Rodak |
| 5,472,442 | A | 12/1995 | Klicek |
| 5,474,057 | A | 12/1995 | Makower et al. |
| 5,474,566 | A | 12/1995 | Alesi et al. |
| 5,476,479 | A | 12/1995 | Green et al. |
| 5,478,354 | A | 12/1995 | Tovey et al. |
| 5,480,089 | A | 1/1996 | Blewett |
| 5,480,409 | A | 1/1996 | Riza |
| 5,482,197 | A | 1/1996 | Green et al. |
| 5,483,952 | A | 1/1996 | Aranyi |
| 5,484,095 | A | 1/1996 | Green et al. |
| 5,484,398 | A | 1/1996 | Stoddard |
| 5,484,451 | A | 1/1996 | Akopov et al. |
| 5,485,947 | A | 1/1996 | Olson et al. |
| 5,485,952 | A | 1/1996 | Fontayne |
| 5,487,499 | A | 1/1996 | Sorrentino et al. |
| 5,487,500 | A | 1/1996 | Knodel et al. |
| 5,489,058 | A | 2/1996 | Plyley et al. |
| 5,490,819 | A | 2/1996 | Nicholas et al. |
| 5,496,312 | A | 3/1996 | Klicek |
| 5,496,317 | A | 3/1996 | Goble et al. |
| 5,497,933 | A | 3/1996 | DeFonzo et al. |
| 5,498,201 | A * | 3/1996 | Volk .................. A22C 21/0038 383/71 |
| 5,503,320 | A | 4/1996 | Webster et al. |
| 5,503,635 | A | 4/1996 | Sauer et al. |
| 5,505,363 | A | 4/1996 | Green et al. |
| 5,507,426 | A | 4/1996 | Young et al. |
| 5,509,596 | A | 4/1996 | Green et al. |
| 5,509,916 | A | 4/1996 | Taylor |
| 5,511,564 | A | 4/1996 | Wilk |
| 5,513,885 | A * | 5/1996 | Joffe .................. A61J 9/0623 215/396 |
| 5,514,157 | A | 5/1996 | Nicholas et al. |
| 5,518,163 | A | 5/1996 | Hooven |
| 5,518,164 | A | 5/1996 | Hooven |
| 5,520,609 | A | 5/1996 | Moll et al. |
| 5,520,678 | A | 5/1996 | Heckele et al. |
| 5,520,700 | A | 5/1996 | Beyar et al. |
| 5,527,264 | A | 6/1996 | Moll et al. |
| 5,529,235 | A | 6/1996 | Boiarski et al. |
| 5,531,856 | A | 7/1996 | Moll et al. |
| 5,533,661 | A | 7/1996 | Main et al. |
| 5,535,934 | A | 7/1996 | Boiarski et al. |
| 5,535,935 | A | 7/1996 | Vidal et al. |
| 5,535,937 | A | 7/1996 | Boiarski et al. |
| 5,540,375 | A | 7/1996 | Bolanos et al. |
| 5,541,376 | A | 7/1996 | Ladtkow et al. |
| 5,542,594 | A | 8/1996 | McKean et al. |
| 5,547,117 | A | 8/1996 | Hamblin et al. |
| 5,549,621 | A | 8/1996 | Bessler et al. |
| 5,549,637 | A | 8/1996 | Crainich |
| 5,551,622 | A | 9/1996 | Yoon |
| 5,553,765 | A | 9/1996 | Knodel et al. |
| 5,554,169 | A | 9/1996 | Green et al. |
| 5,556,416 | A | 9/1996 | Clark et al. |
| 5,556,918 | A | 9/1996 | Brodt et al. |
| 5,558,665 | A | 9/1996 | Kieturakis |
| D374,758 | S * | 10/1996 | Armenta .................. D2/891 |
| 5,560,530 | A | 10/1996 | Bolanos et al. |
| 5,560,532 | A | 10/1996 | DeFonzo et al. |
| 5,562,239 | A | 10/1996 | Boiarski et al. |
| 5,562,241 | A | 10/1996 | Knodel et al. |
| 5,562,682 | A | 10/1996 | Oberlin et al. |
| 5,562,690 | A | 10/1996 | Green et al. |
| 5,562,701 | A | 10/1996 | Huitema et al. |
| 5,562,702 | A | 10/1996 | Huitema et al. |
| 5,564,615 | A | 10/1996 | Bishop et al. |
| 5,571,116 | A | 11/1996 | Bolanos et al. |
| 5,571,285 | A | 11/1996 | Chow et al. |
| 5,575,799 | A | 11/1996 | Bolanos et al. |
| 5,575,803 | A | 11/1996 | Cooper et al. |
| 5,575,805 | A | 11/1996 | Li |
| 5,577,654 | A | 11/1996 | Bishop |
| 5,579,978 | A | 12/1996 | Green et al. |
| 5,580,067 | A | 12/1996 | Hamblin et al. |
| 5,584,425 | A | 12/1996 | Savage et al. |
| 5,586,711 | A | 12/1996 | Plyley et al. |
| 5,588,579 | A | 12/1996 | Schnut et al. |
| 5,588,580 | A | 12/1996 | Paul et al. |
| 5,588,581 | A | 12/1996 | Conlon et al. |
| 5,597,107 | A | 1/1997 | Knodel et al. |
| 5,599,344 | A | 2/1997 | Paterson |
| 5,601,224 | A | 2/1997 | Bishop et al. |
| 5,603,443 | A | 2/1997 | Clark et al. |
| 5,605,272 | A | 2/1997 | Witt et al. |
| 5,605,273 | A | 2/1997 | Hamblin et al. |
| 5,607,094 | A | 3/1997 | Clark et al. |
| 5,607,095 | A | 3/1997 | Smith et al. |
| 5,607,450 | A | 3/1997 | Zvenyatsky et al. |
| 5,609,285 | A | 3/1997 | Grant et al. |
| 5,609,601 | A | 3/1997 | Kolesa et al. |
| 5,611,709 | A | 3/1997 | McAnulty |
| 5,613,937 | A | 3/1997 | Garrison et al. |
| 5,613,966 | A | 3/1997 | Makower et al. |
| 5,615,820 | A | 4/1997 | Viola |
| 5,618,303 | A | 4/1997 | Marlow et al. |
| 5,618,307 | A | 4/1997 | Donlon et al. |
| 5,619,992 | A | 4/1997 | Guthrie et al. |
| 5,620,452 | A | 4/1997 | Yoon |
| 5,624,452 | A | 4/1997 | Yates |
| 5,628,446 | A | 5/1997 | Geiste et al. |
| 5,628,743 | A | 5/1997 | Cimino |
| 5,628,745 | A | 5/1997 | Bek |
| 5,630,259 | A * | 5/1997 | Ricketts .................. A44B 6/00 24/300 |
| 5,630,539 | A | 5/1997 | Plyley et al. |
| 5,630,540 | A | 5/1997 | Blewett |
| 5,632,432 | A | 5/1997 | Schulze et al. |
| 5,632,433 | A | 5/1997 | Grant et al. |
| 5,634,584 | A | 6/1997 | Okorocha et al. |
| 5,636,779 | A | 6/1997 | Palmer |
| 5,636,780 | A | 6/1997 | Green et al. |
| 5,639,008 | A | 6/1997 | Gallagher et al. |
| 5,644,799 | A * | 7/1997 | Armenta .................. A42B 1/225 132/273 |
| 5,645,209 | A | 7/1997 | Green et al. |
| 5,647,526 | A | 7/1997 | Green et al. |
| 5,647,869 | A | 7/1997 | Goble et al. |
| 5,649,937 | A | 7/1997 | Bito et al. |

(56) References Cited

U.S. PATENT DOCUMENTS

| | | |
|---|---|---|
| 5,651,491 A | 7/1997 | Heaton et al. |
| 5,651,762 A | 7/1997 | Bridges |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,680,983 A | 10/1997 | Plyley et al. |
| 5,681,341 A | 10/1997 | Lunsford et al. |
| 5,683,349 A | 11/1997 | Makower et al. |
| 5,685,474 A | 11/1997 | Seeber |
| 5,685,826 A | 11/1997 | Bonutti |
| 5,688,270 A | 11/1997 | Yates et al. |
| 5,690,269 A | 11/1997 | Bolanos et al. |
| 5,692,668 A | 12/1997 | Schulze et al. |
| 5,693,020 A | 12/1997 | Rauh |
| 5,693,042 A | 12/1997 | Boiarski et al. |
| 5,695,494 A | 12/1997 | Becker |
| 5,695,504 A | 12/1997 | Gifford, III et al. |
| 5,695,524 A | 12/1997 | Kelley et al. |
| 5,697,543 A | 12/1997 | Burdorff |
| 5,697,943 A | 12/1997 | Sauer et al. |
| 5,700,270 A | 12/1997 | Peyser et al. |
| 5,702,387 A | 12/1997 | Arts et al. |
| 5,702,408 A | 12/1997 | Wales et al. |
| 5,702,409 A | 12/1997 | Rayburn et al. |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,680 A | 1/1998 | Yates et al. |
| 5,709,706 A | 1/1998 | Kienzle et al. |
| 5,711,472 A | 1/1998 | Bryan |
| 5,713,505 A | 2/1998 | Huitema |
| 5,713,895 A | 2/1998 | Lontine et al. |
| 5,715,604 A | 2/1998 | Lanzoni |
| 5,715,987 A | 2/1998 | Kelley et al. |
| 5,716,366 A | 2/1998 | Yates |
| 5,718,359 A | 2/1998 | Palmer et al. |
| 5,718,360 A | 2/1998 | Green et al. |
| 5,718,624 A * | 2/1998 | Volk .................. A22C 21/0038 206/340 |
| 5,720,744 A | 2/1998 | Eggleston et al. |
| 5,725,536 A | 3/1998 | Oberlin et al. |
| 5,725,554 A | 3/1998 | Simon et al. |
| 5,728,121 A | 3/1998 | Bimbo et al. |
| 5,730,758 A | 3/1998 | Allgeyer |
| 5,732,871 A | 3/1998 | Clark et al. |
| 5,732,872 A | 3/1998 | Bolduc et al. |
| 5,735,874 A | 4/1998 | Measamer et al. |
| 5,738,228 A * | 4/1998 | Bittinger ............... A47F 7/0021 211/60.1 |
| 5,738,629 A | 4/1998 | Moll et al. |
| 5,741,271 A | 4/1998 | Nakao et al. |
| 5,743,456 A | 4/1998 | Jones et al. |
| 5,749,778 A * | 5/1998 | Volk .................. A22C 21/0038 452/174 |
| 5,749,889 A | 5/1998 | Bacich et al. |
| 5,749,893 A | 5/1998 | Vidal et al. |
| 5,752,644 A | 5/1998 | Bolanos et al. |
| 5,752,965 A | 5/1998 | Francis et al. |
| 5,752,970 A | 5/1998 | Yoon |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,892 A | 6/1998 | Kingwell |
| 5,772,659 A | 6/1998 | Becker et al. |
| 5,776,130 A | 7/1998 | Buysse et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,748 A | 7/1998 | Palmer et al. |
| 5,782,859 A | 7/1998 | Nicholas et al. |
| 5,785,232 A | 7/1998 | Vidal et al. |
| 5,785,647 A | 7/1998 | Tompkins et al. |
| 5,787,897 A | 8/1998 | Kieturakis |
| 5,792,135 A | 8/1998 | Madhani et al. |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,797,959 A | 8/1998 | Castro et al. |
| 5,799,857 A | 9/1998 | Robertson et al. |
| 5,800,379 A | 9/1998 | Edwards |
| 5,807,376 A | 9/1998 | Viola et al. |
| 5,807,378 A | 9/1998 | Jensen et al. |
| 5,810,721 A | 9/1998 | Mueller et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,817,084 A | 10/1998 | Jensen |
| 5,817,093 A | 10/1998 | Williamson, IV et al. |
| 5,820,009 A | 10/1998 | Melling et al. |
| 5,826,776 A | 10/1998 | Schulze et al. |
| 5,827,271 A | 10/1998 | Buysse et al. |
| 5,827,298 A | 10/1998 | Hart et al. |
| 5,829,662 A | 11/1998 | Allen et al. |
| 5,830,598 A | 11/1998 | Patterson |
| 5,833,695 A | 11/1998 | Yoon |
| 5,836,503 A | 11/1998 | Ehrenfels et al. |
| 5,839,369 A | 11/1998 | Chatterjee et al. |
| 5,839,639 A | 11/1998 | Sauer et al. |
| 5,843,021 A | 12/1998 | Edwards et al. |
| 5,843,096 A | 12/1998 | Igaki et al. |
| D404,525 S * | 1/1999 | Knudsen .................... D28/42 |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,868,760 A | 2/1999 | McGuckin, Jr. |
| 5,868,790 A | 2/1999 | Vincent et al. |
| 5,871,135 A | 2/1999 | Williamson, IV et al. |
| 5,876,401 A | 3/1999 | Schulze et al. |
| 5,878,937 A | 3/1999 | Green et al. |
| 5,891,558 A | 4/1999 | Bell et al. |
| 5,893,506 A | 4/1999 | Powell |
| 5,894,979 A | 4/1999 | Powell |
| 5,897,552 A | 4/1999 | Edwards et al. |
| 5,897,562 A | 4/1999 | Bolanos et al. |
| 5,901,895 A | 5/1999 | Heaton et al. |
| 5,902,312 A | 5/1999 | Frater et al. |
| 5,906,577 A | 5/1999 | Beane et al. |
| 5,906,625 A | 5/1999 | Bito et al. |
| 5,908,402 A | 6/1999 | Blythe |
| 5,908,427 A | 6/1999 | McKean et al. |
| 5,911,353 A | 6/1999 | Bolanos et al. |
| 5,915,616 A | 6/1999 | Viola et al. |
| 5,918,791 A | 7/1999 | Sorrentino et al. |
| 5,919,198 A | 7/1999 | Graves, Jr. et al. |
| 5,931,853 A | 8/1999 | McEwen et al. |
| 5,937,867 A * | 8/1999 | Williams ............... A41G 5/0073 132/133 |
| 5,937,951 A | 8/1999 | Izuchukwu et al. |
| 5,938,667 A | 8/1999 | Peyser et al. |

(56) References Cited

U.S. PATENT DOCUMENTS

| | | | |
|---|---|---|---|
| 5,941,442 A | 8/1999 | Geiste et al. | |
| 5,944,715 A | 8/1999 | Goble et al. | |
| 5,947,984 A | 9/1999 | Whipple | |
| 5,947,996 A | 9/1999 | Logeman | |
| 5,951,552 A | 9/1999 | Long et al. | |
| 5,951,576 A | 9/1999 | Wakabayashi | |
| 5,954,259 A | 9/1999 | Viola et al. | |
| 5,960,973 A * | 10/1999 | Markson | G09F 3/04 215/386 |
| 5,964,774 A | 10/1999 | McKean et al. | |
| 5,997,528 A | 12/1999 | Bisch et al. | |
| 5,997,552 A | 12/1999 | Person et al. | |
| 6,003,517 A | 12/1999 | Sheffield et al. | |
| 6,004,319 A | 12/1999 | Goble et al. | |
| 6,010,054 A | 1/2000 | Johnson et al. | |
| 6,012,494 A | 1/2000 | Balazs | |
| 6,015,406 A | 1/2000 | Goble et al. | |
| 6,017,356 A | 1/2000 | Frederick et al. | |
| 6,024,741 A | 2/2000 | Williamson, IV et al. | |
| 6,024,748 A | 2/2000 | Manzo et al. | |
| 6,027,501 A | 2/2000 | Goble et al. | |
| 6,032,849 A | 3/2000 | Mastri et al. | |
| 6,033,399 A | 3/2000 | Gines | |
| 6,039,734 A | 3/2000 | Goble | |
| 6,045,560 A | 4/2000 | McKean et al. | |
| 6,050,172 A | 4/2000 | Corves et al. | |
| 6,050,472 A | 4/2000 | Shibata | |
| 6,050,996 A | 4/2000 | Schmaltz et al. | |
| 6,053,390 A | 4/2000 | Green et al. | |
| RE36,720 E | 5/2000 | Green et al. | |
| 6,056,735 A | 5/2000 | Okada et al. | |
| 6,063,025 A | 5/2000 | Bridges et al. | |
| 6,063,097 A | 5/2000 | Oi et al. | |
| 6,066,132 A | 5/2000 | Chen et al. | |
| 6,068,627 A | 5/2000 | Orszulak et al. | |
| 6,074,401 A | 6/2000 | Gardiner et al. | |
| 6,079,606 A | 6/2000 | Milliman et al. | |
| 6,083,191 A | 7/2000 | Rose | |
| 6,083,234 A | 7/2000 | Nicholas et al. | |
| 6,083,241 A | 7/2000 | Longo et al. | |
| 6,083,242 A | 7/2000 | Cook | |
| 6,086,600 A | 7/2000 | Kortenbach | |
| 6,093,186 A | 7/2000 | Goble | |
| 6,099,551 A | 8/2000 | Gabbay | |
| 6,102,271 A | 8/2000 | Longo et al. | |
| 6,109,500 A | 8/2000 | Alli et al. | |
| 6,117,148 A | 9/2000 | Ravo et al. | |
| 6,117,158 A | 9/2000 | Measamer et al. | |
| 6,119,913 A | 9/2000 | Adams et al. | |
| H1904 H | 10/2000 | Yates et al. | |
| 6,126,058 A | 10/2000 | Adams et al. | |
| 6,131,790 A | 10/2000 | Piraka | |
| 6,142,933 A | 11/2000 | Longo et al. | |
| 6,149,660 A | 11/2000 | Laufer et al. | |
| 6,155,473 A | 12/2000 | Tompkins et al. | |
| 6,156,056 A | 12/2000 | Kearns et al. | |
| 6,159,146 A | 12/2000 | El Gazayerli | |
| 6,159,200 A | 12/2000 | Verdura et al. | |
| 6,161,263 A * | 12/2000 | Anderson | A41B 11/002 24/30.5 S |
| 6,162,208 A | 12/2000 | Hipps | |
| 6,165,188 A | 12/2000 | Saadat et al. | |
| 6,171,330 B1 | 1/2001 | Benchetrit | |
| 6,174,318 B1 | 1/2001 | Bates et al. | |
| 6,179,195 B1 | 1/2001 | Adams et al. | |
| 6,187,003 B1 | 2/2001 | Buysse et al. | |
| 6,193,129 B1 | 2/2001 | Bittner et al. | |
| 6,202,914 B1 | 3/2001 | Geiste et al. | |
| 6,210,403 B1 | 4/2001 | Klicek | |
| 6,213,999 B1 | 4/2001 | Platt, Jr. et al. | |
| 6,214,020 B1 | 4/2001 | Mulhauser et al. | |
| 6,214,028 B1 | 4/2001 | Yoon et al. | |
| 6,216,698 B1 | 4/2001 | Regula | |
| 6,221,007 B1 | 4/2001 | Green | |
| 6,228,081 B1 | 5/2001 | Goble | |
| 6,228,083 B1 | 5/2001 | Lands et al. | |
| 6,231,565 B1 | 5/2001 | Tovey et al. | |
| 6,234,178 B1 | 5/2001 | Goble et al. | |
| 6,241,139 B1 | 6/2001 | Milliman et al. | |
| 6,241,140 B1 | 6/2001 | Adams et al. | |
| 6,241,723 B1 | 6/2001 | Heim et al. | |
| 6,248,117 B1 | 6/2001 | Blatter | |
| 6,250,532 B1 | 6/2001 | Green et al. | |
| D445,980 S * | 7/2001 | Tjugum | D32/61 |
| 6,254,534 B1 | 7/2001 | Butler et al. | |
| 6,258,107 B1 | 7/2001 | Balazs et al. | |
| 6,261,286 B1 | 7/2001 | Goble et al. | |
| 6,264,086 B1 | 7/2001 | McGuckin, Jr. | |
| 6,264,087 B1 | 7/2001 | Whitman | |
| 6,267,772 B1 | 7/2001 | Mulhauser et al. | |
| 6,273,897 B1 | 8/2001 | Dalessandro et al. | |
| 6,277,114 B1 | 8/2001 | Bullivant et al. | |
| 6,293,927 B1 | 9/2001 | McGuckin, Jr. | |
| 6,302,311 B1 | 10/2001 | Adams et al. | |
| 6,309,403 B1 | 10/2001 | Minor et al. | |
| 6,315,184 B1 | 11/2001 | Whitman | |
| 6,322,494 B1 | 11/2001 | Bullivant et al. | |
| 6,325,799 B1 | 12/2001 | Goble | |
| 6,325,805 B1 | 12/2001 | Ogilvie et al. | |
| 6,325,810 B1 | 12/2001 | Hamilton et al. | |
| 6,330,965 B1 | 12/2001 | Milliman et al. | |
| 6,331,181 B1 | 12/2001 | Tierney et al. | |
| 6,334,861 B1 | 1/2002 | Chandler et al. | |
| 6,336,926 B1 | 1/2002 | Goble | |
| 6,338,737 B1 | 1/2002 | Toledano | |
| 6,343,731 B1 | 2/2002 | Adams et al. | |
| 6,346,077 B1 | 2/2002 | Taylor et al. | |
| 6,352,503 B1 | 3/2002 | Matsui et al. | |
| 6,354,325 B1 * | 3/2002 | Warnes | E03B 9/10 137/367 |
| 6,358,224 B1 | 3/2002 | Tims et al. | |
| 6,364,888 B1 | 4/2002 | Niemeyer et al. | |
| 6,387,113 B1 | 5/2002 | Hawkins et al. | |
| 6,391,038 B2 | 5/2002 | Vargas et al. | |
| 6,398,797 B2 | 6/2002 | Bombard et al. | |
| 6,402,766 B2 | 6/2002 | Bowman et al. | |
| 6,402,780 B2 | 6/2002 | Williamson, IV et al. | |
| H2037 H | 7/2002 | Yates et al. | |
| RE37,814 E | 8/2002 | Allgeyer | |
| 6,436,107 B1 | 8/2002 | Wang et al. | |
| 6,436,110 B2 | 8/2002 | Bowman et al. | |
| 6,436,122 B1 | 8/2002 | Frank et al. | |
| 6,439,446 B1 | 8/2002 | Perry et al. | |
| 6,440,146 B2 | 8/2002 | Nicholas et al. | |
| 6,443,973 B1 | 9/2002 | Whitman | |
| 6,447,523 B1 | 9/2002 | Middleman et al. | |
| 6,450,391 B1 | 9/2002 | Kayan et al. | |
| 6,458,077 B1 | 10/2002 | Boebel et al. | |
| 6,478,210 B2 | 11/2002 | Adams et al. | |
| 6,488,196 B1 | 12/2002 | Fenton, Jr. | |
| 6,488,197 B1 | 12/2002 | Whitman | |
| 6,488,659 B1 | 12/2002 | Rosenman | |
| 6,491,201 B1 | 12/2002 | Whitman | |
| 6,491,267 B1 * | 12/2002 | Feldman | A45D 20/12 248/176.1 |
| 6,491,690 B1 | 12/2002 | Goble et al. | |
| 6,491,701 B2 | 12/2002 | Tierney et al. | |
| 6,494,885 B1 | 12/2002 | Dhindsa | |
| 6,502,711 B1 * | 1/2003 | McRae | B65D 21/0204 211/71.01 |
| 6,503,257 B2 | 1/2003 | Grant et al. | |
| 6,503,259 B2 | 1/2003 | Huxel et al. | |
| 6,505,768 B2 | 1/2003 | Whitman | |
| 6,510,854 B2 | 1/2003 | Goble | |
| 6,517,528 B1 | 2/2003 | Pantages et al. | |
| 6,517,565 B1 | 2/2003 | Whitman et al. | |
| 6,517,566 B1 | 2/2003 | Hovland et al. | |
| 6,533,157 B1 | 3/2003 | Whitman | |
| 6,540,737 B2 | 4/2003 | Bacher et al. | |
| 6,543,456 B1 | 4/2003 | Freeman | |
| 6,551,333 B2 | 4/2003 | Kuhns et al. | |
| 6,558,379 B1 | 5/2003 | Batchelor et al. | |
| 6,569,085 B2 | 5/2003 | Kortenbach et al. | |
| 6,569,171 B2 | 5/2003 | DeGuillebon et al. | |

(56) References Cited

U.S. PATENT DOCUMENTS

| | | |
|---|---|---|
| 6,578,751 B2 | 6/2003 | Hartwick |
| 6,582,364 B2 | 6/2003 | Butler et al. |
| 6,585,144 B2 | 7/2003 | Adams et al. |
| 6,588,643 B2 | 7/2003 | Bolduc et al. |
| 6,589,118 B1 | 7/2003 | Soma et al. |
| 6,592,597 B2 | 7/2003 | Grant et al. |
| 6,601,749 B2 | 8/2003 | Sullivan et al. |
| 6,605,078 B2 | 8/2003 | Adams |
| 6,607,475 B2 | 8/2003 | Doyle et al. |
| 6,616,686 B2 | 9/2003 | Coleman et al. |
| 6,619,529 B2 | 9/2003 | Green et al. |
| 6,629,630 B2 | 10/2003 | Adams |
| 6,629,988 B2 | 10/2003 | Weadock |
| 6,638,285 B2 | 10/2003 | Gabbay |
| 6,638,297 B1 | 10/2003 | Huitema |
| 6,644,532 B2 | 11/2003 | Green et al. |
| 6,645,201 B1 | 11/2003 | Utley et al. |
| 6,648,901 B2 | 11/2003 | Fleischman et al. |
| 6,655,390 B2 * | 12/2003 | Gueret ............... A45D 40/267 132/138 |
| 6,656,193 B2 | 12/2003 | Grant et al. |
| 6,656,514 B1 * | 12/2003 | Tubbs ................. A47J 47/08 220/229 |
| 6,666,854 B1 | 12/2003 | Lange |
| 6,669,073 B2 | 12/2003 | Milliman et al. |
| 6,670,806 B2 | 12/2003 | Wendt et al. |
| 6,676,660 B2 | 1/2004 | Wampler et al. |
| 6,681,978 B2 | 1/2004 | Geiste et al. |
| 6,681,979 B2 | 1/2004 | Whitman |
| 6,682,528 B2 | 1/2004 | Frazier et al. |
| 6,692,507 B2 | 2/2004 | Pugsley et al. |
| 6,695,198 B2 | 2/2004 | Adams et al. |
| 6,695,199 B2 | 2/2004 | Whitman |
| 6,698,643 B2 | 3/2004 | Whitman |
| 6,699,235 B2 | 3/2004 | Wallace et al. |
| 6,716,232 B1 | 4/2004 | Vidal et al. |
| 6,716,233 B1 | 4/2004 | Whitman |
| 6,722,552 B2 | 4/2004 | Fenton, Jr. |
| 6,723,087 B2 | 4/2004 | O'Neill et al. |
| 6,723,109 B2 | 4/2004 | Solingen |
| 6,726,697 B2 | 4/2004 | Nicholas et al. |
| 6,736,825 B2 | 5/2004 | Blatter et al. |
| 6,749,560 B1 | 6/2004 | Konstorum et al. |
| 6,749,600 B1 | 6/2004 | Levy |
| 6,752,816 B2 | 6/2004 | Culp et al. |
| 6,755,338 B2 | 6/2004 | Hahnen et al. |
| 6,761,685 B2 | 7/2004 | Adams et al. |
| 6,763,955 B2 * | 7/2004 | Keis .................. A47J 47/16 211/60.1 |
| 6,769,590 B2 | 8/2004 | Vresh et al. |
| 6,769,594 B2 | 8/2004 | Orban, III |
| 6,773,438 B1 | 8/2004 | Knodel et al. |
| 6,780,151 B2 | 8/2004 | Grabover et al. |
| 6,786,382 B1 | 9/2004 | Hoffman |
| 6,786,896 B1 | 9/2004 | Madhani et al. |
| 6,793,652 B1 | 9/2004 | Whitman et al. |
| 6,793,661 B2 | 9/2004 | Hamilton et al. |
| 6,805,273 B2 | 10/2004 | Bilotti et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,820,791 B2 | 11/2004 | Adams |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,830,174 B2 | 12/2004 | Hillstead et al. |
| 6,835,199 B2 | 12/2004 | McGuckin, Jr. et al. |
| 6,835,336 B2 | 12/2004 | Watt |
| 6,840,423 B2 | 1/2005 | Adams et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,858,005 B2 | 2/2005 | Ohline et al. |
| RE38,708 E | 3/2005 | Bolanos et al. |
| 6,866,178 B2 | 3/2005 | Adams et al. |
| 6,866,671 B2 | 3/2005 | Tierney et al. |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,905,057 B2 | 6/2005 | Swayze et al. |
| 6,908,472 B2 | 6/2005 | Wiener et al. |
| 6,913,608 B2 | 7/2005 | Liddicoat et al. |
| 6,913,613 B2 | 7/2005 | Schwarz et al. |
| 6,932,810 B2 | 8/2005 | Ryan |
| 6,936,042 B2 | 8/2005 | Wallace et al. |
| 6,939,358 B2 | 9/2005 | Palacios et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,958,035 B2 | 10/2005 | Friedman et al. |
| 6,959,851 B2 | 11/2005 | Heinrich |
| 6,959,852 B2 | 11/2005 | Shelton, IV et al. |
| 6,960,220 B2 | 11/2005 | Marino et al. |
| 6,964,363 B2 | 11/2005 | Wales et al. |
| 6,969,395 B2 | 11/2005 | Eskuri |
| 6,971,988 B2 | 12/2005 | Orban, III |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,978 B2 | 1/2006 | Gannoe |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,995,729 B2 | 2/2006 | Govari et al. |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,001,408 B2 | 2/2006 | Knodel et al. |
| 7,004,179 B1 * | 2/2006 | Lunde ................. A45D 8/12 132/273 |
| 7,008,435 B2 | 3/2006 | Cummins |
| 7,018,357 B2 | 3/2006 | Emmons |
| 7,032,798 B2 | 4/2006 | Whitman et al. |
| 7,032,799 B2 | 4/2006 | Viola et al. |
| 7,037,314 B2 | 5/2006 | Armstrong |
| 7,044,352 B2 | 5/2006 | Shelton, IV et al. |
| 7,044,353 B2 | 5/2006 | Mastri et al. |
| 7,052,454 B2 | 5/2006 | Taylor |
| 7,052,494 B2 | 5/2006 | Goble et al. |
| 7,055,731 B2 | 6/2006 | Shelton, IV et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,712 B2 | 6/2006 | Vargas et al. |
| 7,066,944 B2 | 6/2006 | Laufer et al. |
| 7,070,083 B2 | 7/2006 | Jankowski |
| 7,077,856 B2 | 7/2006 | Whitman |
| 7,080,769 B2 | 7/2006 | Vresh et al. |
| 7,083,075 B2 | 8/2006 | Swayze et al. |
| 7,083,626 B2 | 8/2006 | Hart et al. |
| 7,087,071 B2 | 8/2006 | Nicholas et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,094,247 B2 | 8/2006 | Monassevitch et al. |
| 7,097,089 B2 | 8/2006 | Marczyk |
| 7,097,644 B2 | 8/2006 | Long |
| 7,100,808 B2 * | 9/2006 | Hancock .............. F16L 3/10 224/547 |
| 7,108,701 B2 | 9/2006 | Evens et al. |
| 7,108,709 B2 | 9/2006 | Cummins |
| 7,111,769 B2 | 9/2006 | Wales et al. |
| 7,114,642 B2 | 10/2006 | Whitman |
| 7,118,582 B1 | 10/2006 | Wang et al. |
| 7,119,534 B2 | 10/2006 | Butzmann |
| 7,121,446 B2 | 10/2006 | Arad et al. |
| 7,122,028 B2 | 10/2006 | Looper et al. |
| 7,128,253 B2 | 10/2006 | Mastri et al. |
| 7,128,254 B2 | 10/2006 | Shelton, IV et al. |
| 7,128,748 B2 | 10/2006 | Mooradian et al. |

(56) References Cited

U.S. PATENT DOCUMENTS

| | | |
|---|---|---|
| 7,131,445 B2 | 11/2006 | Amoah |
| 7,133,601 B2 | 11/2006 | Phillips et al. |
| 7,134,587 B2 | 11/2006 | Schwemberger et al. |
| 7,137,981 B2 | 11/2006 | Long |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,147,637 B2 | 12/2006 | Goble |
| 7,147,650 B2 | 12/2006 | Lee |
| 7,150,748 B2 | 12/2006 | Ebbutt et al. |
| 7,156,863 B2 | 1/2007 | Sonnenschein et al. |
| 7,159,750 B2 | 1/2007 | Racenet et al. |
| 7,160,299 B2 | 1/2007 | Baily |
| 7,168,604 B2 | 1/2007 | Milliman et al. |
| 7,172,104 B2 | 2/2007 | Scirica et al. |
| 7,179,267 B2 | 2/2007 | Nolan et al. |
| 7,182,239 B1 | 2/2007 | Myers |
| 7,188,758 B2 | 3/2007 | Viola et al. |
| 7,199,537 B2 | 4/2007 | Okamura et al. |
| 7,204,404 B2 | 4/2007 | Nguyen et al. |
| 7,204,835 B2 | 4/2007 | Latterell et al. |
| 7,207,471 B2 | 4/2007 | Heinrich et al. |
| 7,207,472 B2 | 4/2007 | Wukusick et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,213,736 B2 | 5/2007 | Wales et al. |
| 7,220,272 B2 | 5/2007 | Weadock |
| 7,225,963 B2 | 6/2007 | Scirica |
| 7,225,964 B2 | 6/2007 | Mastri et al. |
| 7,229,408 B2 | 6/2007 | Douglas et al. |
| 7,234,624 B2 | 6/2007 | Gresham et al. |
| 7,235,089 B1 | 6/2007 | McGuckin, Jr. |
| 7,237,708 B1 | 7/2007 | Guy et al. |
| 7,238,195 B2 | 7/2007 | Viola |
| 7,241,288 B2 | 7/2007 | Braun |
| 7,241,289 B2 | 7/2007 | Braun |
| 7,246,734 B2 | 7/2007 | Shelton, IV |
| 7,247,161 B2 | 7/2007 | Johnston et al. |
| 7,252,660 B2 | 8/2007 | Kunz |
| 7,258,262 B2 | 8/2007 | Mastri et al. |
| 7,258,546 B2 | 8/2007 | Beier et al. |
| 7,267,679 B2 | 9/2007 | McGuckin, Jr. et al. |
| 7,278,562 B2 | 10/2007 | Mastri et al. |
| 7,278,563 B1 | 10/2007 | Green |
| 7,282,048 B2 | 10/2007 | Goble et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,203 B2 | 2/2008 | Papineau et al. |
| 7,328,828 B2 | 2/2008 | Ortiz et al. |
| 7,328,829 B2 | 2/2008 | Arad et al. |
| 7,331,340 B2 | 2/2008 | Barney |
| 7,331,969 B1 | 2/2008 | Inganas et al. |
| 7,334,717 B2 | 2/2008 | Rethy et al. |
| 7,334,718 B2 | 2/2008 | McAlister et al. |
| 7,336,048 B2 | 2/2008 | Lohr |
| 7,338,505 B2 | 3/2008 | Belson |
| 7,338,513 B2 | 3/2008 | Lee et al. |
| 7,343,920 B2 | 3/2008 | Toby et al. |
| RE40,237 E | 4/2008 | Bilotti et al. |
| 7,354,447 B2 | 4/2008 | Shelton, IV et al. |
| 7,357,287 B2 | 4/2008 | Shelton, IV et al. |
| 7,357,806 B2 | 4/2008 | Rivera et al. |
| 7,364,060 B2 | 4/2008 | Milliman |
| 7,364,061 B2 | 4/2008 | Swayze et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,398,908 B2 | 7/2008 | Holsten et al. |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,321 B2 | 9/2008 | Tereschouk |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,427,607 B2 | 9/2008 | Suzuki |
| 7,431,188 B1 | 10/2008 | Marczyk |
| 7,431,189 B2 | 10/2008 | Shelton, IV et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,438,718 B2 | 10/2008 | Milliman et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,221 B2 | 1/2009 | Ewers et al. |
| 7,473,253 B2 | 1/2009 | Dycus et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,124 B2 | 2/2009 | Kuhns et al. |
| 7,487,899 B2 | 2/2009 | Shelton, IV et al. |
| 7,490,749 B2 | 2/2009 | Schall et al. |
| 7,491,232 B2 | 2/2009 | Bolduc et al. |
| 7,494,039 B2 | 2/2009 | Racenet et al. |
| 7,494,499 B2 | 2/2009 | Nagase et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,527,632 B2 | 5/2009 | Houghton et al. |
| 7,530,984 B2 | 5/2009 | Sonnenschein et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |

(56) References Cited

U.S. PATENT DOCUMENTS

| | | | |
|---|---|---|---|
| 7,556,185 B2 | 7/2009 | Viola | |
| 7,556,186 B2 | 7/2009 | Milliman | |
| 7,556,647 B2 | 7/2009 | Drews et al. | |
| 7,559,449 B2 | 7/2009 | Viola | |
| 7,559,450 B2 | 7/2009 | Wales et al. | |
| 7,559,452 B2 | 7/2009 | Wales et al. | |
| 7,565,993 B2 | 7/2009 | Milliman et al. | |
| D599,074 S * | 8/2009 | Bizzell | B65F 1/06 D34/10 |
| 7,568,603 B2 | 8/2009 | Shelton, IV et al. | |
| 7,568,604 B2 | 8/2009 | Ehrenfels et al. | |
| 7,575,144 B2 | 8/2009 | Ortiz et al. | |
| 7,588,174 B2 | 9/2009 | Holsten et al. | |
| 7,588,175 B2 | 9/2009 | Timm et al. | |
| 7,588,176 B2 | 9/2009 | Timm et al. | |
| 7,588,177 B2 | 9/2009 | Racenet | |
| 7,597,229 B2 | 10/2009 | Boudreaux et al. | |
| 7,597,230 B2 | 10/2009 | Racenet et al. | |
| 7,600,663 B2 | 10/2009 | Green | |
| 7,601,903 B1 * | 10/2009 | Monk | G10D 13/12 84/422.4 |
| 7,604,150 B2 | 10/2009 | Boudreaux | |
| 7,604,151 B2 | 10/2009 | Hess et al. | |
| 7,607,557 B2 | 10/2009 | Shelton, IV et al. | |
| 7,611,038 B2 | 11/2009 | Racenet et al. | |
| 7,615,067 B2 | 11/2009 | Lee et al. | |
| 7,624,902 B2 | 12/2009 | Marczyk et al. | |
| 7,624,903 B2 | 12/2009 | Green et al. | |
| 7,625,370 B2 | 12/2009 | Hart et al. | |
| 7,631,793 B2 | 12/2009 | Rethy et al. | |
| 7,631,794 B2 | 12/2009 | Rethy et al. | |
| 7,635,074 B2 | 12/2009 | Olson et al. | |
| 7,637,409 B2 | 12/2009 | Marczyk | |
| 7,638,958 B2 | 12/2009 | Philipp et al. | |
| 7,641,091 B2 | 1/2010 | Olson et al. | |
| 7,641,092 B2 | 1/2010 | Kruszynski et al. | |
| 7,641,095 B2 | 1/2010 | Viola | |
| 7,641,835 B2 * | 1/2010 | Ramsey | B65F 1/06 220/495.08 |
| 7,644,848 B2 | 1/2010 | Swayze et al. | |
| 7,645,230 B2 | 1/2010 | Mikkaichi et al. | |
| 7,648,519 B2 | 1/2010 | Lee et al. | |
| 7,651,017 B2 | 1/2010 | Ortiz et al. | |
| 7,654,431 B2 | 2/2010 | Hueil et al. | |
| 7,658,311 B2 | 2/2010 | Boudreaux | |
| 7,658,312 B2 | 2/2010 | Vidal et al. | |
| 7,662,161 B2 | 2/2010 | Briganti et al. | |
| 7,665,646 B2 | 2/2010 | Prommersberger | |
| 7,665,647 B2 | 2/2010 | Shelton, IV et al. | |
| 7,669,746 B2 | 3/2010 | Shelton, IV | |
| 7,669,747 B2 | 3/2010 | Weisenburgh, II et al. | |
| 7,670,334 B2 | 3/2010 | Hueil et al. | |
| 7,673,780 B2 | 3/2010 | Shelton, IV et al. | |
| 7,673,781 B2 | 3/2010 | Swayze et al. | |
| 7,673,782 B2 | 3/2010 | Hess et al. | |
| 7,673,783 B2 | 3/2010 | Morgan et al. | |
| 7,674,255 B2 | 3/2010 | Braun | |
| 7,682,686 B2 | 3/2010 | Curro et al. | |
| 7,686,201 B2 | 3/2010 | Csiky | |
| 7,686,826 B2 | 3/2010 | Lee et al. | |
| 7,691,098 B2 | 4/2010 | Wallace et al. | |
| 7,694,864 B2 | 4/2010 | Okada et al. | |
| 7,694,865 B2 | 4/2010 | Scirica | |
| 7,695,485 B2 | 4/2010 | Whitman et al. | |
| 7,699,204 B2 | 4/2010 | Viola | |
| 7,699,844 B2 | 4/2010 | Utley et al. | |
| 7,699,846 B2 | 4/2010 | Ryan | |
| 7,699,856 B2 | 4/2010 | Van Wyk et al. | |
| 7,699,859 B2 | 4/2010 | Bombard et al. | |
| 7,703,653 B2 | 4/2010 | Shah et al. | |
| 7,708,180 B2 | 5/2010 | Murray et al. | |
| 7,708,181 B2 | 5/2010 | Cole et al. | |
| 7,708,182 B2 | 5/2010 | Viola | |
| 7,708,758 B2 | 5/2010 | Lee et al. | |
| 7,717,312 B2 | 5/2010 | Beetel | |
| 7,717,313 B2 | 5/2010 | Criscuolo et al. | |
| 7,717,846 B2 | 5/2010 | Zirps et al. | |
| 7,717,873 B2 | 5/2010 | Swick | |
| 7,721,885 B2 * | 5/2010 | Conklin | B25H 3/00 206/338 |
| 7,721,930 B2 | 5/2010 | McKenna et al. | |
| 7,721,931 B2 | 5/2010 | Shelton, IV et al. | |
| 7,721,933 B2 | 5/2010 | Ehrenfels et al. | |
| 7,721,934 B2 | 5/2010 | Shelton, IV et al. | |
| 7,721,936 B2 | 5/2010 | Shalton, IV et al. | |
| 7,726,537 B2 | 6/2010 | Olson et al. | |
| 7,726,538 B2 | 6/2010 | Holsten et al. | |
| 7,731,072 B2 | 6/2010 | Timm et al. | |
| 7,735,703 B2 | 6/2010 | Morgan et al. | |
| 7,736,306 B2 | 6/2010 | Brustad et al. | |
| 7,738,971 B2 | 6/2010 | Swayze et al. | |
| 7,740,159 B2 | 6/2010 | Shelton, IV et al. | |
| 7,743,960 B2 | 6/2010 | Whitman et al. | |
| 7,744,624 B2 | 6/2010 | Bettuchi | |
| 7,744,627 B2 | 6/2010 | Orban, III et al. | |
| 7,744,628 B2 | 6/2010 | Viola | |
| 7,751,870 B2 | 7/2010 | Whitman | |
| 7,753,245 B2 | 7/2010 | Boudreaux et al. | |
| 7,753,904 B2 | 7/2010 | Shelton, IV et al. | |
| 7,758,612 B2 | 7/2010 | Shipp | |
| 7,766,207 B2 | 8/2010 | Mather et al. | |
| 7,766,209 B2 | 8/2010 | Baxter, III et al. | |
| 7,766,210 B2 | 8/2010 | Shelton, IV et al. | |
| 7,766,821 B2 | 8/2010 | Brunnen et al. | |
| 7,770,773 B2 | 8/2010 | Whitman et al. | |
| 7,770,774 B2 | 8/2010 | Mastri et al. | |
| 7,770,775 B2 | 8/2010 | Shelton, IV et al. | |
| 7,770,776 B2 | 8/2010 | Chen et al. | |
| 7,776,060 B2 | 8/2010 | Mooradian et al. | |
| 7,780,054 B2 | 8/2010 | Wales | |
| 7,780,055 B2 | 8/2010 | Scirica et al. | |
| 7,780,685 B2 | 8/2010 | Hunt et al. | |
| 7,784,662 B2 | 8/2010 | Wales et al. | |
| 7,784,663 B2 | 8/2010 | Shelton, IV | |
| 7,789,889 B2 | 9/2010 | Zubik et al. | |
| 7,793,812 B2 | 9/2010 | Moore et al. | |
| 7,794,475 B2 | 9/2010 | Hess et al. | |
| 7,798,386 B2 | 9/2010 | Schall et al. | |
| 7,799,039 B2 | 9/2010 | Shelton, IV et al. | |
| 7,803,151 B2 | 9/2010 | Whitman | |
| 7,806,891 B2 | 10/2010 | Nowlin et al. | |
| 7,810,690 B2 | 10/2010 | Bilotti et al. | |
| 7,810,691 B2 | 10/2010 | Boyden et al. | |
| 7,810,692 B2 | 10/2010 | Hall et al. | |
| 7,810,693 B2 | 10/2010 | Broehl et al. | |
| 7,815,092 B2 | 10/2010 | Whitman et al. | |
| 7,819,296 B2 | 10/2010 | Hueil et al. | |
| 7,819,297 B2 | 10/2010 | Doll et al. | |
| 7,819,298 B2 | 10/2010 | Hall et al. | |
| 7,819,299 B2 | 10/2010 | Shelton, IV et al. | |
| 7,823,592 B2 | 11/2010 | Bettuchi et al. | |
| 7,823,760 B2 | 11/2010 | Zemlok et al. | |
| 7,824,426 B2 | 11/2010 | Racenet et al. | |
| 7,828,189 B2 | 11/2010 | Holsten et al. | |
| 7,828,808 B2 | 11/2010 | Hinman et al. | |
| 7,832,408 B2 | 11/2010 | Shelton, IV et al. | |
| 7,832,611 B2 | 11/2010 | Boyden et al. | |
| 7,832,612 B2 | 11/2010 | Baxter, III et al. | |
| 7,833,234 B2 | 11/2010 | Bailly et al. | |
| 7,837,079 B2 | 11/2010 | Holsten et al. | |
| 7,837,080 B2 | 11/2010 | Schwemberger | |
| 7,837,081 B2 | 11/2010 | Holsten et al. | |
| 7,837,694 B2 | 11/2010 | Tethrake et al. | |
| 7,842,028 B2 | 11/2010 | Lee | |
| 7,845,533 B2 | 12/2010 | Marczyk et al. | |
| 7,845,534 B2 | 12/2010 | Viola et al. | |
| 7,845,535 B2 | 12/2010 | Scircia | |
| 7,845,536 B2 | 12/2010 | Viola et al. | |
| 7,845,537 B2 | 12/2010 | Shelton, IV et al. | |
| 7,846,149 B2 | 12/2010 | Jankowski | |
| 7,854,736 B2 | 12/2010 | Ryan | |
| 7,857,183 B2 | 12/2010 | Shelton, IV | |
| 7,857,185 B2 | 12/2010 | Swayze et al. | |
| 7,857,186 B2 | 12/2010 | Baxter, III et al. | |

(56) References Cited

U.S. PATENT DOCUMENTS

| | | |
|---|---|---|
| 7,861,906 B2 | 1/2011 | Doll et al. |
| 7,862,502 B2 | 1/2011 | Pool et al. |
| 7,866,525 B2 | 1/2011 | Scirica |
| 7,866,527 B2 | 1/2011 | Hall et al. |
| 7,870,989 B2 | 1/2011 | Viola et al. |
| 7,871,418 B2 | 1/2011 | Thompson et al. |
| 7,879,070 B2 | 2/2011 | Ortiz et al. |
| 7,883,461 B2 | 2/2011 | Albrecht et al. |
| 7,886,951 B2 | 2/2011 | Hessler |
| 7,886,952 B2 | 2/2011 | Scirica et al. |
| 7,886,953 B2 | 2/2011 | Schwemberger et al. |
| 7,891,531 B1 | 2/2011 | Ward |
| 7,891,532 B2 | 2/2011 | Mastri et al. |
| 7,892,245 B2 | 2/2011 | Liddicoat et al. |
| 7,893,586 B2 | 2/2011 | West et al. |
| 7,896,214 B2 | 3/2011 | Farascioni |
| 7,896,215 B2 | 3/2011 | Adams et al. |
| 7,896,877 B2 | 3/2011 | Hall et al. |
| 7,896,897 B2 | 3/2011 | Gresham et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,905,889 B2 | 3/2011 | Catanese, III et al. |
| 7,905,902 B2 | 3/2011 | Huitema et al. |
| 7,909,039 B2 | 3/2011 | Hur |
| 7,909,220 B2 | 3/2011 | Viola |
| 7,909,221 B2 | 3/2011 | Viola et al. |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,845 B2 | 4/2011 | Saadat et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,926,691 B2 | 4/2011 | Viola et al. |
| 7,931,660 B2 | 4/2011 | Aranyi et al. |
| 7,931,877 B2 | 4/2011 | Steffens et al. |
| 7,934,630 B2 | 5/2011 | Shelton, IV et al. |
| 7,934,631 B2 | 5/2011 | Balbierz et al. |
| 7,935,773 B2 | 5/2011 | Hadba et al. |
| 7,938,307 B2 | 5/2011 | Bettuchi |
| 7,942,303 B2 | 5/2011 | Shah |
| 7,942,890 B2 | 5/2011 | D'Agostino et al. |
| 7,950,560 B2 | 5/2011 | Zemlok et al. |
| 7,950,561 B2 | 5/2011 | Aranyi |
| 7,951,071 B2 | 5/2011 | Whitman et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,954,687 B2 | 6/2011 | Zemlok et al. |
| 7,955,253 B2 | 6/2011 | Ewers et al. |
| 7,955,257 B2 | 6/2011 | Frasier et al. |
| 7,959,050 B2 | 6/2011 | Smith et al. |
| 7,959,051 B2 | 6/2011 | Smith et al. |
| 7,963,432 B2 | 6/2011 | Knodel et al. |
| 7,963,433 B2 | 6/2011 | Whitman et al. |
| 7,966,799 B2 | 6/2011 | Morgan et al. |
| 7,967,180 B2 | 6/2011 | Scirica |
| 7,967,181 B2 | 6/2011 | Viola et al. |
| 7,967,791 B2 | 6/2011 | Franer et al. |
| 7,967,839 B2 | 6/2011 | Flock et al. |
| 7,972,298 B2 | 7/2011 | Wallace et al. |
| 7,976,563 B2 | 7/2011 | Summerer |
| 7,980,443 B2 | 7/2011 | Scheib et al. |
| 7,981,132 B2 | 7/2011 | Dubrul et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,988,779 B2 | 8/2011 | Disalvo et al. |
| 7,992,757 B2 | 8/2011 | Wheeler et al. |
| 7,997,469 B2 | 8/2011 | Olson et al. |
| 8,002,696 B2 | 8/2011 | Suzuki |
| 8,002,795 B2 | 8/2011 | Beetel |
| 8,006,885 B2 | 8/2011 | Marczyk |
| 8,006,889 B2 | 8/2011 | Adams et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,849 B2 | 9/2011 | Wenchell |
| 8,016,855 B2 | 9/2011 | Whitman et al. |
| 8,016,858 B2 | 9/2011 | Whitman |
| 8,020,742 B2 | 9/2011 | Marczyk |
| 8,020,743 B2 | 9/2011 | Shelton, IV |
| 8,021,389 B2 | 9/2011 | Molz, IV |
| 8,025,199 B2 | 9/2011 | Whitman et al. |
| 8,028,883 B2 | 10/2011 | Stopek |
| 8,028,884 B2 | 10/2011 | Sniffin et al. |
| 8,028,885 B2 | 10/2011 | Smith et al. |
| 8,033,438 B2 | 10/2011 | Scirica |
| 8,033,440 B2 | 10/2011 | Wenchell et al. |
| 8,034,077 B2 | 10/2011 | Smith et al. |
| 8,035,487 B2 | 10/2011 | Malackowski |
| 8,038,045 B2 | 10/2011 | Bettuchi et al. |
| 8,038,046 B2 | 10/2011 | Smith et al. |
| 8,043,207 B2 | 10/2011 | Adams |
| 8,043,328 B2 | 10/2011 | Hahnen et al. |
| 8,047,236 B2 | 11/2011 | Perry |
| 8,056,787 B2 | 11/2011 | Boudreaux et al. |
| 8,056,788 B2 | 11/2011 | Mastri et al. |
| 8,061,558 B2 | 11/2011 | Jordan et al. |
| 8,062,330 B2 | 11/2011 | Prommersberger et al. |
| 8,066,167 B2 | 11/2011 | Measamer et al. |
| 8,066,168 B2 | 11/2011 | Vidal et al. |
| D650,074 S | 12/2011 | Hunt et al. |
| 8,074,858 B2 | 12/2011 | Marczyk |
| 8,075,476 B2 | 12/2011 | Vargas |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,091,756 B2 | 1/2012 | Viola |
| 8,092,932 B2 | 1/2012 | Phillips et al. |
| 8,096,457 B1 | 1/2012 | Manoux et al. |
| 8,097,017 B2 | 1/2012 | Viola |
| 8,100,310 B2 | 1/2012 | Zemlok |
| 8,105,350 B2 | 1/2012 | Lee et al. |
| 8,109,426 B2 | 2/2012 | Milliman et al. |
| 8,113,405 B2 | 2/2012 | Milliman |
| 8,113,410 B2 | 2/2012 | Hall et al. |
| 8,114,100 B2 | 2/2012 | Smith et al. |
| 8,123,103 B2 | 2/2012 | Milliman |
| 8,123,767 B2 | 2/2012 | Bauman et al. |
| 8,127,975 B2 | 3/2012 | Olson et al. |
| 8,127,976 B2 | 3/2012 | Scirica et al. |
| 8,128,559 B2 | 3/2012 | Minnelli |
| 8,128,645 B2 | 3/2012 | Sonnenschein et al. |
| 8,132,703 B2 | 3/2012 | Milliman et al. |
| 8,132,706 B2 | 3/2012 | Marczyk et al. |
| 8,136,712 B2 | 3/2012 | Zingman |
| 8,136,713 B2 | 3/2012 | Hathaway et al. |
| 8,140,417 B2 | 3/2012 | Shibata |
| 8,141,762 B2 | 3/2012 | Bedi et al. |
| 8,141,763 B2 | 3/2012 | Milliman |
| 8,146,790 B2 | 4/2012 | Milliman |
| 8,147,456 B2 | 4/2012 | Fisher et al. |
| 8,152,041 B2 | 4/2012 | Kostrzewski |
| 8,152,756 B2 | 4/2012 | Webster et al. |
| 8,157,145 B2 | 4/2012 | Shelton, IV et al. |
| 8,157,148 B2 | 4/2012 | Scirica |
| 8,157,152 B2 | 4/2012 | Holsten et al. |
| 8,157,153 B2 | 4/2012 | Shelton, IV et al. |
| 8,161,977 B2 | 4/2012 | Shelton, IV et al. |
| 8,162,197 B2 | 4/2012 | Mastri et al. |
| 8,162,933 B2 | 4/2012 | Francischelli et al. |
| 8,167,185 B2 | 5/2012 | Shelton, IV et al. |
| 8,167,895 B2 | 5/2012 | D'Agostino et al. |
| 8,172,120 B2 | 5/2012 | Boyden et al. |
| 8,172,122 B2 | 5/2012 | Kasvikis et al. |

(56) References Cited

U.S. PATENT DOCUMENTS

| | | | |
|---|---|---|---|
| 8,172,124 B2 | 5/2012 | Shelton, IV et al. |
| 8,177,797 B2 | 5/2012 | Shimoji et al. |
| 8,186,555 B2 | 5/2012 | Shelton, IV et al. |
| 8,186,560 B2 | 5/2012 | Hess et al. |
| 8,191,752 B2 | 6/2012 | Scirica |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,533 B2 | 7/2012 | Viola et al. |
| 8,220,688 B2 | 7/2012 | Laurent et al. |
| 8,220,690 B2 | 7/2012 | Hess et al. |
| 8,225,799 B2 | 7/2012 | Bettuchi |
| 8,226,553 B2 | 7/2012 | Shelton, IV et al. |
| 8,231,040 B2 | 7/2012 | Zemlok et al. |
| 8,231,042 B2 | 7/2012 | Hessler et al. |
| 8,231,043 B2 | 7/2012 | Tarinelli et al. |
| 8,236,010 B2 | 8/2012 | Ortiz et al. |
| 8,241,271 B2 | 8/2012 | Millman et al. |
| 8,241,308 B2 | 8/2012 | Kortenbach et al. |
| 8,241,322 B2 | 8/2012 | Whitman et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,637 B2 | 8/2012 | Viola et al. |
| 8,256,654 B2 | 9/2012 | Bettuchi et al. |
| 8,256,655 B2 | 9/2012 | Sniffin et al. |
| 8,257,251 B2 | 9/2012 | Shelton, IV et al. |
| 8,267,300 B2 | 9/2012 | Boudreaux |
| 8,272,553 B2 | 9/2012 | Mastri et al. |
| 8,276,801 B2 | 10/2012 | Zemlok et al. |
| 8,276,802 B2 | 10/2012 | Kostrzewski |
| 8,281,973 B2 | 10/2012 | Wenchell et al. |
| 8,286,845 B2 | 10/2012 | Perry et al. |
| 8,286,846 B2 | 10/2012 | Smith et al. |
| 8,287,561 B2 | 10/2012 | Nunez et al. |
| 8,292,151 B2 | 10/2012 | Viola |
| 8,292,155 B2 | 10/2012 | Shelton, IV et al. |
| 8,292,157 B2 | 10/2012 | Smith et al. |
| 8,292,888 B2 | 10/2012 | Whitman |
| 8,298,189 B2 | 10/2012 | Fisher et al. |
| 8,308,040 B2 | 11/2012 | Huang et al. |
| 8,308,042 B2 | 11/2012 | Aranyi |
| 8,308,043 B2 | 11/2012 | Bindra et al. |
| 8,308,046 B2 | 11/2012 | Prommersberger |
| 8,308,638 B2 | 11/2012 | Hart |
| 8,313,496 B2 | 11/2012 | Sauer et al. |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,744 B2 | 11/2012 | Kirschenman |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,328,062 B2 | 12/2012 | Viola |
| 8,328,063 B2 | 12/2012 | Milliman et al. |
| 8,328,064 B2 | 12/2012 | Racenet et al. |
| 8,333,313 B2 | 12/2012 | Boudreaux et al. |
| 8,333,691 B2 | 12/2012 | Schaaf |
| 8,333,764 B2 | 12/2012 | Francischelli et al. |
| 8,336,753 B2 | 12/2012 | Olson et al. |
| 8,337,517 B2 | 12/2012 | Van Dalen |
| 8,348,123 B2 | 1/2013 | Scirica et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,837 B2 | 1/2013 | Wenchell |
| 8,348,972 B2 | 1/2013 | Soltz et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,357,142 B2 * | 1/2013 | Romero ............ A61B 90/50 604/533 |
| 8,357,144 B2 | 1/2013 | Whitman et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,973 B1 | 2/2013 | White et al. |
| 8,365,975 B1 | 2/2013 | Manoux et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,377,029 B2 | 2/2013 | Nagao et al. |
| 8,393,513 B2 | 3/2013 | Jankowski |
| 8,393,514 B2 | 3/2013 | Shelton, IV et al. |
| 8,397,971 B2 | 3/2013 | Yates et al. |
| 8,398,633 B2 | 3/2013 | Mueller |
| 8,398,669 B2 | 3/2013 | Kim |
| 8,403,198 B2 | 3/2013 | Sorrentino et al. |
| 8,403,945 B2 | 3/2013 | Whitfield et al. |
| 8,408,439 B2 | 4/2013 | Huang et al. |
| 8,408,442 B2 | 4/2013 | Racenet et al. |
| 8,409,079 B2 | 4/2013 | Okamoto et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,439,246 B1 | 5/2013 | Knodel |
| 8,444,036 B2 | 5/2013 | Shelton, IV |
| 8,453,904 B2 | 6/2013 | Eskaros et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,459,520 B2 | 6/2013 | Giordano et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,465,515 B2 | 6/2013 | Drew et al. |
| 8,469,973 B2 | 6/2013 | Meade et al. |
| 8,470,355 B2 | 6/2013 | Skalla et al. |
| 8,474,677 B2 | 7/2013 | Woodard, Jr. et al. |
| 8,475,454 B1 | 7/2013 | Alshemari |
| 8,475,457 B2 | 7/2013 | Shano |
| 8,479,967 B2 | 7/2013 | Marczyk |
| 8,479,969 B2 | 7/2013 | Shelton, IV |
| 8,480,703 B2 | 7/2013 | Nicholas et al. |
| 8,485,412 B2 | 7/2013 | Shelton, IV et al. |
| 8,485,413 B2 | 7/2013 | Scheib et al. |
| 8,485,414 B2 | 7/2013 | Criscuolo et al. |
| 8,485,970 B2 | 7/2013 | Widenhouse et al. |
| 8,490,853 B2 | 7/2013 | Criscuolo et al. |
| 8,491,603 B2 | 7/2013 | Yeung et al. |
| 8,496,156 B2 | 7/2013 | Sniffin et al. |
| 8,499,993 B2 | 8/2013 | Shelton, IV et al. |
| 8,506,555 B2 | 8/2013 | Ruiz Morales |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,517,931 B2 | 8/2013 | Minnelli et al. |
| 8,523,043 B2 | 9/2013 | Ullrich et al. |
| 8,523,881 B2 | 9/2013 | Cabiri et al. |
| 8,529,600 B2 | 9/2013 | Woodard, Jr. et al. |
| 8,534,528 B2 | 9/2013 | Shelton, IV |

(56) References Cited

U.S. PATENT DOCUMENTS

| | | |
|---|---|---|
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,733 B2 | 9/2013 | Whitman et al. |
| 8,550,984 B2 | 10/2013 | Takemoto |
| 8,556,151 B2 | 10/2013 | Viola |
| 8,556,918 B2 | 10/2013 | Bauman et al. |
| 8,561,870 B2 | 10/2013 | Baxter, III et al. |
| 8,561,873 B2 | 10/2013 | Ingmanson et al. |
| 8,567,655 B2 | 10/2013 | Nalagatla et al. |
| 8,567,656 B2 | 10/2013 | Shelton, IV et al. |
| 8,568,425 B2 | 10/2013 | Ross et al. |
| 8,573,459 B2 | 11/2013 | Smith et al. |
| 8,573,461 B2 | 11/2013 | Shelton, IV et al. |
| 8,573,462 B2 | 11/2013 | Smith et al. |
| 8,573,464 B2 | 11/2013 | Nalagatla et al. |
| 8,573,465 B2 | 11/2013 | Shelton, IV |
| 8,579,176 B2 | 11/2013 | Smith et al. |
| 8,579,178 B2 | 11/2013 | Holsten et al. |
| 8,579,937 B2 | 11/2013 | Gresham |
| 8,584,919 B2 | 11/2013 | Hueil et al. |
| 8,590,760 B2 | 11/2013 | Cummins et al. |
| 8,590,762 B2 | 11/2013 | Hess et al. |
| 8,590,764 B2 | 11/2013 | Hartwick et al. |
| 8,602,287 B2 | 12/2013 | Yates et al. |
| 8,602,288 B2 | 12/2013 | Shelton, IV et al. |
| 8,603,089 B2 | 12/2013 | Viola |
| 8,608,043 B2 | 12/2013 | Scirica |
| 8,608,044 B2 | 12/2013 | Hueil et al. |
| 8,608,045 B2 | 12/2013 | Smith et al. |
| 8,608,046 B2 | 12/2013 | Laurent et al. |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,627,993 B2 | 1/2014 | Smith et al. |
| 8,627,995 B2 | 1/2014 | Smith et al. |
| 8,631,987 B2 | 1/2014 | Shelton, IV et al. |
| 8,631,993 B2 | 1/2014 | Kostrzewski |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 8,636,187 B2 | 1/2014 | Hueil et al. |
| 8,636,191 B2 | 1/2014 | Meagher |
| 8,636,736 B2 | 1/2014 | Yates et al. |
| 8,640,788 B2 | 2/2014 | Dachs, II et al. |
| 8,640,940 B2 | 2/2014 | Ohdaira |
| 8,652,120 B2 | 2/2014 | Giordano et al. |
| 8,657,174 B2 | 2/2014 | Yates et al. |
| 8,657,176 B2 | 2/2014 | Shelton, IV et al. |
| 8,657,178 B2 | 2/2014 | Hueil et al. |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,672,839 B2 | 3/2014 | Ewers et al. |
| 8,672,951 B2 | 3/2014 | Smith et al. |
| 8,678,263 B2 | 3/2014 | Viola |
| 8,679,154 B2 | 3/2014 | Smith et al. |
| 8,679,156 B2 | 3/2014 | Smith et al. |
| 8,684,253 B2 | 4/2014 | Giordano et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,708,210 B2 | 4/2014 | Zemlok et al. |
| 8,708,213 B2 | 4/2014 | Shelton, IV et al. |
| 8,714,429 B2 | 5/2014 | Demmy |
| 8,714,430 B2 | 5/2014 | Natarajan et al. |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,199 B2 | 5/2014 | Wenchell |
| 8,727,961 B2 | 5/2014 | Ziv |
| 8,733,612 B2 | 5/2014 | Ma |
| 8,733,613 B2 | 5/2014 | Huitema et al. |
| 8,734,336 B2 | 5/2014 | Bonadio et al. |
| 8,734,478 B2 | 5/2014 | Widenhouse et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,746,529 B2 | 6/2014 | Shelton, IV et al. |
| 8,746,530 B2 | 6/2014 | Giordano et al. |
| 8,746,533 B2 | 6/2014 | Whitman et al. |
| 8,746,535 B2 | 6/2014 | Shelton, IV et al. |
| 8,747,238 B2 | 6/2014 | Shelton, IV et al. |
| 8,752,699 B2 | 6/2014 | Morgan et al. |
| 8,752,747 B2 | 6/2014 | Shelton, IV et al. |
| 8,752,749 B2 | 6/2014 | Moore et al. |
| 8,757,465 B2 | 6/2014 | Woodard, Jr. et al. |
| 8,758,235 B2 | 6/2014 | Jaworek |
| 8,758,391 B2 | 6/2014 | Swayze et al. |
| 8,763,875 B2 | 7/2014 | Morgan et al. |
| 8,763,877 B2 | 7/2014 | Schall et al. |
| 8,763,879 B2 | 7/2014 | Shelton, IV et al. |
| 8,764,773 B2 | 7/2014 | Harari et al. |
| 8,770,458 B2 | 7/2014 | Scirica |
| 8,770,459 B2 | 7/2014 | Racenet et al. |
| 8,770,460 B2 | 7/2014 | Belzer |
| 8,777,004 B2 | 7/2014 | Shelton, IV et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,304 B2 | 7/2014 | Mikkaichi et al. |
| 8,789,537 B2 * | 7/2014 | Loredo .............. A45D 8/28 132/133 |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,794,497 B2 | 8/2014 | Zingman |
| 8,795,308 B2 | 8/2014 | Valin |
| 8,800,837 B2 | 8/2014 | Zemlok |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,806,973 B2 | 8/2014 | Ross et al. |
| 8,808,311 B2 | 8/2014 | Heinrich et al. |
| 8,808,325 B2 | 8/2014 | Hess et al. |
| 8,814,024 B2 | 8/2014 | Woodard, Jr. et al. |
| 8,814,788 B2 | 8/2014 | Gan |
| 8,820,603 B2 | 9/2014 | Shelton, IV et al. |
| 8,820,605 B2 | 9/2014 | Shelton, IV |
| 8,827,133 B2 | 9/2014 | Shelton, IV et al. |
| 8,827,134 B2 | 9/2014 | Viola et al. |
| 8,827,903 B2 | 9/2014 | Shelton, IV et al. |
| 8,833,632 B2 | 9/2014 | Swensgard |
| 8,834,464 B2 | 9/2014 | Stewart et al. |
| 8,840,003 B2 | 9/2014 | Morgan et al. |
| 8,840,603 B2 | 9/2014 | Shelton, IV et al. |
| 8,844,789 B2 | 9/2014 | Shelton, IV et al. |
| 8,851,354 B2 | 10/2014 | Swensgard et al. |
| 8,857,693 B2 | 10/2014 | Schuckmann et al. |
| 8,857,694 B2 | 10/2014 | Shelton, IV et al. |
| 8,858,538 B2 | 10/2014 | Belson et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,870,911 B2 | 10/2014 | Williams et al. |
| 8,875,971 B2 | 11/2014 | Hall et al. |
| 8,875,972 B2 | 11/2014 | Weisenburgh, II et al. |
| 8,876,857 B2 | 11/2014 | Burbank |
| 8,888,695 B2 | 11/2014 | Piskun et al. |
| 8,893,946 B2 | 11/2014 | Boudreaux et al. |
| 8,893,949 B2 | 11/2014 | Shelton, IV et al. |
| 8,894,647 B2 | 11/2014 | Beardsley et al. |
| 8,899,462 B2 | 12/2014 | Kostrzewski et al. |
| 8,899,463 B2 | 12/2014 | Schall et al. |

(56) References Cited

U.S. PATENT DOCUMENTS

| | | |
|---|---|---|
| 8,899,465 B2 | 12/2014 | Shelton, IV et al. |
| 8,899,466 B2 | 12/2014 | Baxter, III et al. |
| 8,905,977 B2 | 12/2014 | Shelton et al. |
| 8,910,847 B2 | 12/2014 | Nalagatla et al. |
| 8,911,471 B2 | 12/2014 | Spivey et al. |
| 8,920,433 B2 | 12/2014 | Barrier et al. |
| 8,920,435 B2 | 12/2014 | Smith et al. |
| 8,920,443 B2 | 12/2014 | Hiles et al. |
| 8,925,782 B2 | 1/2015 | Shelton, IV |
| 8,925,788 B2 | 1/2015 | Hess et al. |
| 8,926,506 B2 | 1/2015 | Widenhouse et al. |
| 8,926,598 B2 | 1/2015 | Mollere et al. |
| 8,931,242 B1 * | 1/2015 | Sardo .................... B65B 51/04 383/121 |
| 8,931,682 B2 | 1/2015 | Timm et al. |
| 8,945,163 B2 | 2/2015 | Voegele et al. |
| 8,955,732 B2 | 2/2015 | Zemlok et al. |
| 8,956,390 B2 | 2/2015 | Shah et al. |
| 8,960,519 B2 | 2/2015 | Whitman et al. |
| 8,967,443 B2 | 3/2015 | McCuen |
| 8,967,446 B2 | 3/2015 | Beardsley et al. |
| 8,967,448 B2 | 3/2015 | Carter et al. |
| 8,973,803 B2 | 3/2015 | Hall et al. |
| 8,973,804 B2 | 3/2015 | Hess et al. |
| 8,974,440 B2 | 3/2015 | Farritor et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,991,676 B2 | 3/2015 | Hess et al. |
| 8,991,677 B2 | 3/2015 | Moore et al. |
| 8,992,422 B2 | 3/2015 | Spivey et al. |
| 8,998,058 B2 | 4/2015 | Moore et al. |
| 9,005,230 B2 | 4/2015 | Yates et al. |
| 9,005,238 B2 | 4/2015 | DeSantis et al. |
| 9,005,243 B2 | 4/2015 | Stopek et al. |
| 9,016,541 B2 | 4/2015 | Viola et al. |
| 9,016,542 B2 | 4/2015 | Shelton, IV et al. |
| 9,028,494 B2 | 5/2015 | Shelton, IV et al. |
| 9,028,495 B2 | 5/2015 | Mueller et al. |
| 9,028,519 B2 | 5/2015 | Yates et al. |
| 9,033,203 B2 | 5/2015 | Woodard, Jr. et al. |
| 9,033,204 B2 | 5/2015 | Shelton, IV et al. |
| 9,044,227 B2 | 6/2015 | Shelton, IV et al. |
| 9,044,228 B2 | 6/2015 | Woodard, Jr. et al. |
| 9,044,229 B2 | 6/2015 | Scheib et al. |
| 9,044,230 B2 | 6/2015 | Morgan et al. |
| 9,050,083 B2 | 6/2015 | Yates et al. |
| 9,050,084 B2 | 6/2015 | Schmid et al. |
| 9,050,120 B2 | 6/2015 | Swarup et al. |
| 9,055,941 B2 | 6/2015 | Schmid et al. |
| 9,055,942 B2 | 6/2015 | Balbierz et al. |
| 9,055,944 B2 | 6/2015 | Hodgkinson et al. |
| 9,055,945 B2 | 6/2015 | Miksza et al. |
| 9,060,770 B2 | 6/2015 | Shelton, IV et al. |
| 9,060,894 B2 | 6/2015 | Wubbeling |
| 9,072,515 B2 | 7/2015 | Hall et al. |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,084,601 B2 | 7/2015 | Moore et al. |
| 9,084,602 B2 | 7/2015 | Gleiman |
| 9,089,326 B2 | 7/2015 | Krumanaker et al. |
| 9,089,330 B2 | 7/2015 | Widenhouse et al. |
| 9,089,352 B2 | 7/2015 | Jeong |
| 9,095,339 B2 | 8/2015 | Moore et al. |
| 9,095,340 B2 | 8/2015 | Felder et al. |
| 9,095,362 B2 | 8/2015 | Dachs, II et al. |
| 9,101,358 B2 | 8/2015 | Kerr et al. |
| 9,101,385 B2 | 8/2015 | Shelton, IV et al. |
| 9,107,663 B2 | 8/2015 | Swensgard |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,874 B2 | 8/2015 | Shelton, IV et al. |
| 9,113,880 B2 | 8/2015 | Zemlok et al. |
| 9,113,883 B2 | 8/2015 | Aronhalt et al. |
| 9,113,884 B2 | 8/2015 | Shelton, IV et al. |
| 9,119,657 B2 | 9/2015 | Shelton, IV et al. |
| 9,119,957 B2 | 9/2015 | Gantz et al. |
| 9,125,654 B2 | 9/2015 | Aronhalt et al. |
| 9,125,662 B2 | 9/2015 | Shelton, IV |
| 9,131,835 B2 | 9/2015 | Widenhouse et al. |
| 9,131,940 B2 | 9/2015 | Huitema et al. |
| 9,138,225 B2 | 9/2015 | Huang et al. |
| 9,149,274 B2 | 10/2015 | Spivey et al. |
| 9,149,276 B2 * | 10/2015 | Voss .................. A61B 17/0057 |
| 9,155,536 B1 | 10/2015 | Hausen et al. |
| 9,168,038 B2 | 10/2015 | Shelton, IV et al. |
| 9,173,978 B2 | 11/2015 | Kelly et al. |
| 9,179,911 B2 | 11/2015 | Morgan et al. |
| 9,179,912 B2 | 11/2015 | Yates et al. |
| 9,186,143 B2 | 11/2015 | Timm et al. |
| 9,186,148 B2 | 11/2015 | Felder et al. |
| 9,198,661 B2 | 12/2015 | Swensgard |
| 9,198,662 B2 | 12/2015 | Barton et al. |
| 9,204,830 B2 | 12/2015 | Zand et al. |
| 9,204,879 B2 | 12/2015 | Shelton, IV |
| 9,204,880 B2 | 12/2015 | Baxter, III et al. |
| 9,211,120 B2 | 12/2015 | Scheib et al. |
| 9,211,122 B2 | 12/2015 | Hagerty et al. |
| 9,216,019 B2 | 12/2015 | Schmid et al. |
| 9,220,500 B2 | 12/2015 | Swayze et al. |
| 9,220,501 B2 | 12/2015 | Baxter, III et al. |
| 9,220,559 B2 | 12/2015 | Worrell et al. |
| 9,226,751 B2 | 1/2016 | Shelton, IV et al. |
| 9,232,941 B2 | 1/2016 | Mandakolathur Vasudevan et al. |
| 9,232,945 B2 | 1/2016 | Zingman |
| 9,237,891 B2 | 1/2016 | Shelton, IV |
| 9,241,714 B2 | 1/2016 | Timm et al. |
| 9,265,581 B2 | 2/2016 | Navve et al. |
| 9,271,753 B2 | 3/2016 | Butler et al. |
| 9,271,799 B2 | 3/2016 | Shelton, IV et al. |
| 9,272,406 B2 | 3/2016 | Aronhalt et al. |
| 9,277,919 B2 | 3/2016 | Timmer et al. |
| 9,282,962 B2 | 3/2016 | Schmid et al. |
| 9,282,963 B2 | 3/2016 | Bryant |
| 9,282,966 B2 | 3/2016 | Shelton, IV et al. |
| 9,282,974 B2 | 3/2016 | Shelton, IV |
| 9,289,210 B2 | 3/2016 | Baxter, III et al. |
| 9,289,211 B2 | 3/2016 | Williams et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,295,463 B2 | 3/2016 | Viola et al. |
| 9,295,464 B2 | 3/2016 | Shelton, IV et al. |
| 9,295,784 B2 | 3/2016 | Eggert et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,301,763 B2 | 4/2016 | Qiao et al. |
| 9,307,965 B2 | 4/2016 | Ming et al. |
| 9,307,986 B2 | 4/2016 | Hall et al. |
| 9,307,988 B2 | 4/2016 | Shelton, IV |
| 9,307,989 B2 | 4/2016 | Shelton, IV et al. |
| 9,307,994 B2 | 4/2016 | Gresham et al. |
| 9,314,246 B2 | 4/2016 | Shelton, IV et al. |
| 9,314,247 B2 | 4/2016 | Shelton, IV et al. |
| 9,320,518 B2 | 4/2016 | Henderson et al. |
| 9,320,521 B2 | 4/2016 | Shelton, IV et al. |
| 9,320,522 B2 * | 4/2016 | Carley .................. A61B 17/0057 |
| 9,320,523 B2 | 4/2016 | Shelton, IV et al. |
| 9,326,767 B2 | 5/2016 | Koch et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,326,812 B2 | 5/2016 | Waaler et al. |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,333,082 B2 | 5/2016 | Wei et al. |
| 9,345,477 B2 | 5/2016 | Anim et al. |

(56) References Cited

U.S. PATENT DOCUMENTS

| | | |
|---|---|---|
| 9,345,481 B2 | 5/2016 | Hall et al. |
| 9,351,724 B2 | 5/2016 | Penna |
| 9,351,726 B2 | 5/2016 | Leimbach et al. |
| 9,351,727 B2 | 5/2016 | Leimbach et al. |
| 9,351,730 B2 | 5/2016 | Schmid et al. |
| 9,351,734 B2 | 5/2016 | Prior |
| 9,358,003 B2 | 6/2016 | Hall et al. |
| 9,358,005 B2 | 6/2016 | Shelton, IV et al. |
| 9,364,200 B2 | 6/2016 | Whitman et al. |
| 9,364,217 B2 | 6/2016 | Kostrzewski et al. |
| 9,364,219 B2 | 6/2016 | Olson et al. |
| 9,364,230 B2 | 6/2016 | Shelton, IV et al. |
| 9,364,233 B2 | 6/2016 | Alexander, III et al. |
| 9,370,358 B2 | 6/2016 | Shelton, IV et al. |
| 9,370,364 B2 | 6/2016 | Smith et al. |
| 9,371,226 B2 | 6/2016 | Fox et al. |
| 9,386,983 B2 | 7/2016 | Swensgard et al. |
| 9,386,984 B2 | 7/2016 | Aronhalt et al. |
| 9,386,985 B2 | 7/2016 | Koch, Jr. et al. |
| 9,386,988 B2 | 7/2016 | Baxter, III et al. |
| 9,393,015 B2 | 7/2016 | Laurent et al. |
| 9,398,911 B2 | 7/2016 | Auld |
| 9,402,626 B2 | 8/2016 | Ortiz et al. |
| 9,408,604 B2 | 8/2016 | Shelton, IV et al. |
| 9,408,606 B2 | 8/2016 | Shelton, IV |
| 9,414,838 B2 | 8/2016 | Shelton, IV et al. |
| 9,421,060 B2 | 8/2016 | Monson et al. |
| 9,427,223 B2 | 8/2016 | Park et al. |
| 9,433,419 B2 | 9/2016 | Gonzalez et al. |
| 9,433,420 B2 | 9/2016 | Hodgkinson |
| 9,439,649 B2 | 9/2016 | Shelton, IV et al. |
| 9,439,651 B2 | 9/2016 | Smith et al. |
| 9,451,958 B2 | 9/2016 | Shelton, IV et al. |
| 9,451,980 B2 | 9/2016 | Alfieri |
| 9,463,260 B2 | 10/2016 | Stopek |
| 9,468,438 B2 | 10/2016 | Baber et al. |
| 9,474,519 B2 | 10/2016 | Brustad et al. |
| 9,480,476 B2 | 11/2016 | Aldridge et al. |
| 9,486,213 B2 | 11/2016 | Altman et al. |
| 9,486,214 B2 | 11/2016 | Shelton, IV |
| 9,486,302 B2 | 11/2016 | Boey et al. |
| 9,492,154 B2 | 11/2016 | Melsheimer et al. |
| 9,492,167 B2 | 11/2016 | Shelton, IV et al. |
| 9,492,170 B2 | 11/2016 | Bear et al. |
| 9,498,219 B2 | 11/2016 | Moore et al. |
| 9,510,925 B2 | 12/2016 | Hotter et al. |
| 9,517,063 B2 | 12/2016 | Swayze et al. |
| 9,517,068 B2 | 12/2016 | Shelton, IV et al. |
| 9,517,070 B2 | 12/2016 | Mulreed |
| 9,521,996 B2 | 12/2016 | Armstrong |
| 9,522,029 B2 | 12/2016 | Yates et al. |
| 9,549,732 B2 | 1/2017 | Yates et al. |
| 9,549,738 B2 | 1/2017 | Mandakolathur Vasudevan et al. |
| 9,554,794 B2 | 1/2017 | Baber et al. |
| 9,554,796 B2 | 1/2017 | Kostrzewski |
| 9,561,032 B2 | 2/2017 | Shelton, IV et al. |
| 9,561,038 B2 | 2/2017 | Shelton, IV et al. |
| 9,561,045 B2 | 2/2017 | Hinman et al. |
| 9,566,061 B2 | 2/2017 | Aronhalt et al. |
| 9,572,573 B2 | 2/2017 | Scheib et al. |
| 9,572,574 B2 | 2/2017 | Shelton, IV et al. |
| 9,572,577 B2 | 2/2017 | Lloyd et al. |
| 9,585,550 B2 | 3/2017 | Abel et al. |
| 9,585,657 B2 | 3/2017 | Shelton, IV et al. |
| 9,585,660 B2 | 3/2017 | Laurent et al. |
| 9,592,050 B2 | 3/2017 | Schmid et al. |
| 9,592,052 B2 | 3/2017 | Shelton, IV |
| 9,592,053 B2 | 3/2017 | Shelton, IV et al. |
| 9,592,054 B2 | 3/2017 | Schmid et al. |
| 9,597,075 B2 | 3/2017 | Shelton, IV et al. |
| 9,597,080 B2 | 3/2017 | Milliman et al. |
| 9,597,081 B2 | 3/2017 | Swayze et al. |
| 9,603,595 B2 | 3/2017 | Shelton, IV et al. |
| 9,603,598 B2 | 3/2017 | Shelton, IV et al. |
| 9,603,599 B2 | 3/2017 | Miller et al. |
| 9,603,991 B2 | 3/2017 | Shelton, IV et al. |
| 9,615,826 B2 | 4/2017 | Shelton, IV et al. |
| 9,615,892 B2 | 4/2017 | Piferi et al. |
| 9,629,623 B2 | 4/2017 | Lytle, IV et al. |
| 9,629,626 B2 | 4/2017 | Soltz et al. |
| 9,629,628 B2 | 4/2017 | Aranyi |
| 9,629,629 B2 | 4/2017 | Leimbach et al. |
| 9,629,631 B2 | 4/2017 | Nicholas et al. |
| 9,629,814 B2 | 4/2017 | Widenhouse et al. |
| 9,636,112 B2 | 5/2017 | Penna et al. |
| 9,649,096 B2 | 5/2017 | Sholev |
| 9,649,110 B2 | 5/2017 | Parihar et al. |
| 9,649,111 B2 | 5/2017 | Shelton, IV et al. |
| 9,655,614 B2 | 5/2017 | Swensgard et al. |
| 9,655,624 B2 | 5/2017 | Shelton, IV et al. |
| 9,662,131 B2 | 5/2017 | Omori et al. |
| 9,675,355 B2 | 6/2017 | Shelton, IV et al. |
| 9,675,372 B2 | 6/2017 | Laurent et al. |
| 9,675,375 B2 | 6/2017 | Houser et al. |
| 9,681,870 B2 | 6/2017 | Baxter, III et al. |
| 9,681,873 B2 | 6/2017 | Smith et al. |
| 9,687,230 B2 | 6/2017 | Leimbach et al. |
| 9,687,231 B2 | 6/2017 | Baxter, III et al. |
| 9,687,236 B2 | 6/2017 | Leimbach et al. |
| 9,690,362 B2 | 6/2017 | Leimbach et al. |
| 9,693,777 B2 | 7/2017 | Schellin et al. |
| 9,700,309 B2 | 7/2017 | Jaworek et al. |
| 9,700,317 B2 | 7/2017 | Aronhalt et al. |
| 9,700,321 B2 | 7/2017 | Shelton, IV et al. |
| 9,700,326 B2 | 7/2017 | Morriss et al. |
| 9,706,991 B2 | 7/2017 | Hess et al. |
| 9,724,091 B2 | 8/2017 | Shelton, IV et al. |
| 9,724,094 B2 | 8/2017 | Baber et al. |
| 9,724,100 B2 | 8/2017 | Scheib et al. |
| 9,730,692 B2 | 8/2017 | Shelton, IV et al. |
| 9,733,663 B2 | 8/2017 | Leimbach et al. |
| 9,737,301 B2 | 8/2017 | Baber et al. |
| 9,737,335 B2 | 8/2017 | Butler et al. |
| 9,743,928 B2 | 8/2017 | Shelton, IV et al. |
| 9,743,929 B2 | 8/2017 | Leimbach et al. |
| 9,750,499 B2 | 9/2017 | Leimbach et al. |
| 9,750,502 B2 | 9/2017 | Scirica et al. |
| 9,750,503 B2 | 9/2017 | Milliman |
| 9,757,123 B2 | 9/2017 | Giordano et al. |
| 9,757,124 B2 | 9/2017 | Schellin et al. |
| 9,757,128 B2 | 9/2017 | Baber et al. |
| 9,757,130 B2 | 9/2017 | Shelton, IV |
| 9,757,133 B2 | 9/2017 | Latimer et al. |
| 9,770,245 B2 | 9/2017 | Swayze et al. |
| 9,775,608 B2 | 10/2017 | Aronhalt et al. |
| 9,775,613 B2 | 10/2017 | Shelton, IV et al. |
| 9,782,169 B2 | 10/2017 | Kimsey et al. |
| 9,788,834 B2 | 10/2017 | Schmid et al. |
| 9,788,836 B2 | 10/2017 | Overmyer et al. |
| 9,795,382 B2 | 10/2017 | Shelton, IV |
| 9,795,384 B2 | 10/2017 | Weaner et al. |
| 9,801,626 B2 | 10/2017 | Parihar et al. |
| 9,804,618 B2 | 10/2017 | Leimbach et al. |
| 9,808,244 B2 | 11/2017 | Leimbach et al. |
| 9,808,246 B2 | 11/2017 | Shelton, IV et al. |
| 9,808,247 B2 | 11/2017 | Shelton, IV et al. |
| 9,814,460 B2 | 11/2017 | Kimsey et al. |
| 9,815,213 B2 | 11/2017 | Duey |
| 9,820,738 B2 | 11/2017 | Lytle, IV et al. |
| 9,826,976 B2 | 11/2017 | Parihar et al. |
| 9,826,977 B2 | 11/2017 | Leimbach et al. |
| 9,833,236 B2 | 12/2017 | Shelton, IV et al. |
| 9,833,241 B2 | 12/2017 | Huitema et al. |
| 9,839,420 B2 | 12/2017 | Shelton, IV et al. |
| 9,839,421 B2 | 12/2017 | Zerkle et al. |
| 9,839,422 B2 | 12/2017 | Schellin et al. |
| 9,839,423 B2 | 12/2017 | Vendely et al. |
| 9,839,427 B2 | 12/2017 | Swayze et al. |
| 9,839,428 B2 | 12/2017 | Baxter, III et al. |
| 9,844,368 B2 | 12/2017 | Boudreaux et al. |
| 9,844,369 B2 | 12/2017 | Huitema et al. |
| 9,844,372 B2 | 12/2017 | Shelton, IV et al. |
| 9,844,373 B2 | 12/2017 | Swayze et al. |
| 9,844,374 B2 | 12/2017 | Lytle, IV et al. |

(56) References Cited

U.S. PATENT DOCUMENTS

| | | |
|---|---|---|
| 9,844,375 B2 | 12/2017 | Overmyer et al. |
| 9,848,873 B2 | 12/2017 | Shelton, IV |
| 9,848,875 B2 | 12/2017 | Aronhalt et al. |
| 9,861,359 B2 | 1/2018 | Shelton, IV et al. |
| 9,861,361 B2 | 1/2018 | Aronhalt et al. |
| 9,861,382 B2 | 1/2018 | Smith et al. |
| 9,867,612 B2 | 1/2018 | Parihar et al. |
| 9,867,618 B2 | 1/2018 | Hall et al. |
| 9,872,684 B2 | 1/2018 | Hall et al. |
| 9,877,721 B2 | 1/2018 | Schellin et al. |
| 9,877,722 B2 | 1/2018 | Schellin et al. |
| 9,883,860 B2 | 2/2018 | Leimbach |
| 9,883,861 B2 | 2/2018 | Shelton, IV et al. |
| 9,884,456 B2 | 2/2018 | Schellin et al. |
| 9,888,919 B2 | 2/2018 | Leimbach et al. |
| 9,888,924 B2 | 2/2018 | Ebersole et al. |
| 9,895,148 B2 | 2/2018 | Shelton, IV et al. |
| 9,901,342 B2 | 2/2018 | Shelton, IV et al. |
| 9,907,600 B2 | 3/2018 | Stulen et al. |
| 9,913,642 B2 | 3/2018 | Leimbach et al. |
| 9,913,646 B2 | 3/2018 | Shelton, IV |
| 9,918,704 B2 | 3/2018 | Shelton, IV et al. |
| 9,924,941 B2 | 3/2018 | Burbank |
| 9,924,944 B2 | 3/2018 | Shelton, IV et al. |
| 9,924,961 B2 | 3/2018 | Shelton, IV et al. |
| 9,931,118 B2 | 4/2018 | Shelton, IV et al. |
| 9,943,309 B2 | 4/2018 | Shelton, IV et al. |
| 9,968,355 B2 | 5/2018 | Shelton, IV et al. |
| 9,974,529 B2 | 5/2018 | Shelton, IV et al. |
| 9,980,630 B2 | 5/2018 | Larkin et al. |
| 9,980,713 B2 | 5/2018 | Aronhalt et al. |
| 9,987,000 B2 | 6/2018 | Shelton, IV et al. |
| 9,987,001 B2 | 6/2018 | Williams |
| 9,993,248 B2 | 6/2018 | Shelton, IV et al. |
| 9,993,258 B2 | 6/2018 | Shelton, IV et al. |
| 9,999,408 B2 | 6/2018 | Boudreaux et al. |
| 10,004,497 B2 | 6/2018 | Overmyer et al. |
| 10,004,498 B2 | 6/2018 | Morgan et al. |
| 10,004,501 B2 | 6/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,028,761 B2 | 7/2018 | Leimbach et al. |
| 10,039,529 B2 | 8/2018 | Kerr et al. |
| 10,045,769 B2 | 8/2018 | Aronhalt et al. |
| 10,045,776 B2 | 8/2018 | Shelton, IV et al. |
| 10,045,779 B2 | 8/2018 | Savage et al. |
| 10,052,044 B2 | 8/2018 | Shelton, IV et al. |
| 10,052,099 B2 | 8/2018 | Morgan et al. |
| 10,052,100 B2 | 8/2018 | Morgan et al. |
| 10,052,102 B2 | 8/2018 | Baxter, III et al. |
| 10,058,963 B2 | 8/2018 | Shelton, IV et al. |
| 10,064,621 B2 | 9/2018 | Kerr et al. |
| 10,071,452 B2 | 9/2018 | Shelton, IV et al. |
| 10,085,748 B2 | 10/2018 | Morgan et al. |
| 10,085,806 B2 | 10/2018 | Hagn et al. |
| 10,092,292 B2 | 10/2018 | Boudreaux et al. |
| 10,111,679 B2 | 10/2018 | Baber et al. |
| 10,117,649 B2 | 11/2018 | Baxter, III et al. |
| 10,123,798 B2 | 11/2018 | Baxter, III et al. |
| 10,130,352 B2 | 11/2018 | Widenhouse et al. |
| 10,130,359 B2 | 11/2018 | Hess et al. |
| 10,130,363 B2 | 11/2018 | Huitema et al. |
| 10,130,366 B2 | 11/2018 | Shelton, IV et al. |
| 10,135,242 B2 | 11/2018 | Baber et al. |
| 10,136,887 B2 | 11/2018 | Shelton, IV et al. |
| 10,136,890 B2 | 11/2018 | Shelton, IV et al. |
| 10,136,891 B2 | 11/2018 | Shelton, IV et al. |
| 10,149,680 B2 | 12/2018 | Parihar et al. |
| 10,149,682 B2 | 12/2018 | Shelton, IV et al. |
| 10,159,482 B2 | 12/2018 | Swayze et al. |
| 10,159,483 B2 | 12/2018 | Beckman et al. |
| 10,166,025 B2 | 1/2019 | Leimbach et al. |
| 10,172,611 B2 | 1/2019 | Shelton, IV et al. |
| 10,172,617 B2 | 1/2019 | Shelton, IV et al. |
| 10,178,992 B2 | 1/2019 | Wise et al. |
| 10,180,463 B2 | 1/2019 | Beckman et al. |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,188,393 B2 | 1/2019 | Smith et al. |
| 10,188,394 B2 | 1/2019 | Shelton, IV et al. |
| 10,194,913 B2 | 2/2019 | Nalagatla et al. |
| 10,201,364 B2 | 2/2019 | Leimbach et al. |
| 10,206,678 B2 | 2/2019 | Shelton, IV et al. |
| 10,213,198 B2 | 2/2019 | Aronhalt et al. |
| 10,226,250 B2 | 3/2019 | Beckman et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,058 B2 | 4/2019 | Omori et al. |
| 10,258,330 B2 | 4/2019 | Shelton, IV et al. |
| 10,258,331 B2 | 4/2019 | Shelton, IV et al. |
| 10,265,065 B2 | 4/2019 | Shelton, IV et al. |
| 10,265,068 B2 | 4/2019 | Harris et al. |
| 10,265,090 B2 | 4/2019 | Ingmanson et al. |
| 10,271,851 B2 | 4/2019 | Shelton, IV et al. |
| 10,285,705 B2 | 5/2019 | Shelton, IV et al. |
| 10,292,704 B2 | 5/2019 | Harris et al. |
| 10,292,743 B2 | 5/2019 | Taylor et al. |
| 10,299,792 B2 | 5/2019 | Huitema et al. |
| 10,307,157 B2 | 6/2019 | Miller et al. |
| 10,307,159 B2 | 6/2019 | Harris et al. |
| 10,307,160 B2 | 6/2019 | Vendely et al. |
| 10,314,582 B2 | 6/2019 | Shelton, IV et al. |
| 10,314,588 B2 | 6/2019 | Turner et al. |
| 10,321,907 B2 | 6/2019 | Shelton, IV et al. |
| 10,327,776 B2 | 6/2019 | Harris et al. |
| 10,335,143 B2 | 7/2019 | Whitman et al. |
| 10,335,144 B2 | 7/2019 | Shelton, IV et al. |
| 10,335,149 B2 | 7/2019 | Baxter, III et al. |
| 10,342,533 B2 | 7/2019 | Shelton, IV et al. |
| 10,342,543 B2 | 7/2019 | Shelton, IV et al. |
| 10,357,246 B2 | 7/2019 | Shelton, IV et al. |
| 10,357,248 B2 | 7/2019 | Dalessandro et al. |
| 10,357,251 B2 | 7/2019 | Shelton, IV et al. |
| 10,368,860 B2 | 8/2019 | Nering et al. |
| 10,368,861 B2 | 8/2019 | Baxter, III et al. |
| 10,368,865 B2 | 8/2019 | Harris et al. |
| 10,376,263 B2 | 8/2019 | Morgan et al. |
| 10,383,629 B2 | 8/2019 | Ross et al. |
| 10,390,823 B2 | 8/2019 | Shelton, IV et al. |
| 10,390,829 B2 | 8/2019 | Eckert et al. |
| 10,405,854 B2 | 9/2019 | Schmid et al. |
| 10,405,857 B2 | 9/2019 | Shelton, IV et al. |
| 10,405,863 B2 | 9/2019 | Wise et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,420,552 B2 | 9/2019 | Shelton, IV et al. |
| 10,420,558 B2 | 9/2019 | Nalagatla et al. |
| 10,426,476 B2 | 10/2019 | Harris et al. |
| 10,426,477 B2 | 10/2019 | Harris et al. |
| 10,433,837 B2 | 10/2019 | Worthington et al. |
| 10,433,839 B2 | 10/2019 | Scheib et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,286 B2 | 10/2019 | Shelton, IV et al. |
| 10,441,369 B2 | 10/2019 | Shelton, IV et al. |
| 10,448,948 B2 | 10/2019 | Shelton, IV et al. |
| 10,456,123 B2 | 10/2019 | Hundertmark et al. |
| 10,456,140 B2 | 10/2019 | Shelton, IV et al. |
| 10,463,365 B2 | 11/2019 | Williams |
| 10,470,762 B2 | 11/2019 | Leimbach et al. |
| 10,470,764 B2 | 11/2019 | Baxter, III et al. |
| 10,470,768 B2 | 11/2019 | Harris et al. |
| 10,470,769 B2 | 11/2019 | Shelton, IV et al. |
| 10,478,189 B2 | 11/2019 | Bear et al. |
| 10,478,190 B2 | 11/2019 | Miller et al. |
| 10,485,542 B2 | 11/2019 | Shelton, IV et al. |

(56) References Cited

U.S. PATENT DOCUMENTS

| | | |
|---|---|---|
| 10,492,787 B2 | 12/2019 | Smith et al. |
| 10,499,918 B2 | 12/2019 | Schellin et al. |
| 10,507,039 B2 | 12/2019 | Williams |
| 10,517,594 B2 | 12/2019 | Shelton, IV et al. |
| 10,524,795 B2 | 1/2020 | Nalagatla et al. |
| 10,524,797 B2 | 1/2020 | Sgroi |
| 10,531,874 B2 | 1/2020 | Morgan et al. |
| 10,542,978 B2 | 1/2020 | Chowaniec et al. |
| 10,542,988 B2 | 1/2020 | Schellin et al. |
| 10,542,991 B2 | 1/2020 | Shelton, IV et al. |
| 10,548,504 B2 | 2/2020 | Shelton, IV et al. |
| 10,561,422 B2 | 2/2020 | Schellin et al. |
| 10,568,632 B2 | 2/2020 | Miller et al. |
| 10,569,071 B2 | 2/2020 | Harris et al. |
| 2001/0025183 A1 | 9/2001 | Shahidi |
| 2002/0095175 A1 | 7/2002 | Brock et al. |
| 2002/0103494 A1 | 8/2002 | Pacey |
| 2002/0117534 A1 | 8/2002 | Green et al. |
| 2003/0009193 A1 | 1/2003 | Corsaro |
| 2003/0039689 A1 | 2/2003 | Chen et al. |
| 2003/0096158 A1 | 5/2003 | Takano et al. |
| 2003/0150158 A1* | 8/2003 | Wright ............ A01G 5/04 47/41.12 |
| 2003/0181900 A1 | 9/2003 | Long |
| 2003/0190584 A1 | 10/2003 | Heasley |
| 2003/0236505 A1 | 12/2003 | Bonadio et al. |
| 2004/0054353 A1 | 3/2004 | Taylor |
| 2004/0068161 A1 | 4/2004 | Couvillon |
| 2004/0068224 A1 | 4/2004 | Couvillon et al. |
| 2004/0098040 A1 | 5/2004 | Taniguchi et al. |
| 2004/0102783 A1 | 5/2004 | Sutterlin et al. |
| 2004/0108357 A1 | 6/2004 | Milliman et al. |
| 2004/0113041 A1* | 6/2004 | Hancock ............ B60R 11/00 248/688 |
| 2004/0147909 A1 | 7/2004 | Johnston et al. |
| 2004/0158230 A1 | 8/2004 | Hunn et al. |
| 2004/0158261 A1 | 8/2004 | Vu |
| 2004/0164123 A1 | 8/2004 | Racenet et al. |
| 2004/0167572 A1 | 8/2004 | Roth et al. |
| 2004/0193189 A1 | 9/2004 | Kortenbach et al. |
| 2004/0199181 A1 | 10/2004 | Knodel et al. |
| 2004/0222268 A1 | 11/2004 | Bilotti et al. |
| 2004/0225186 A1 | 11/2004 | Horne et al. |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |
| 2004/0254566 A1 | 12/2004 | Plicchi et al. |
| 2004/0260315 A1 | 12/2004 | Dell et al. |
| 2004/0267310 A1 | 12/2004 | Racenet et al. |
| 2005/0033226 A1 | 2/2005 | Kim |
| 2005/0051163 A1 | 3/2005 | Deem et al. |
| 2005/0059997 A1 | 3/2005 | Bauman et al. |
| 2005/0070929 A1 | 3/2005 | Dalessandro et al. |
| 2005/0080342 A1 | 4/2005 | Gilreath et al. |
| 2005/0085693 A1 | 4/2005 | Belson et al. |
| 2005/0092622 A1* | 5/2005 | Whitley ............ F42B 4/20 206/3 |
| 2005/0125897 A1 | 6/2005 | Wyslucha et al. |
| 2005/0131390 A1 | 6/2005 | Heinrich et al. |
| 2005/0131457 A1 | 6/2005 | Douglas et al. |
| 2005/0139636 A1 | 6/2005 | Schwemberger et al. |
| 2005/0143756 A1 | 6/2005 | Jankowski |
| 2005/0143759 A1 | 6/2005 | Kelly |
| 2005/0154406 A1 | 7/2005 | Bombard et al. |
| 2005/0177181 A1 | 8/2005 | Kagan et al. |
| 2005/0182298 A1 | 8/2005 | Ikeda et al. |
| 2005/0184121 A1 | 8/2005 | Heinrich |
| 2005/0203550 A1 | 9/2005 | Laufer et al. |
| 2005/0216055 A1 | 9/2005 | Scirica et al. |
| 2005/0228224 A1 | 10/2005 | Okada et al. |
| 2005/0236459 A1 | 10/2005 | Gresham |
| 2005/0245965 A1 | 11/2005 | Orban, III et al. |
| 2005/0246881 A1 | 11/2005 | Kelly et al. |
| 2005/0252923 A1* | 11/2005 | Woolf ............ B65D 47/2031 220/731 |
| 2005/0256452 A1 | 11/2005 | DeMarchi et al. |
| 2005/0263523 A1* | 12/2005 | Moss ............ B65D 51/00 220/229 |
| 2005/0263563 A1 | 12/2005 | Racenet et al. |
| 2005/0283188 A1 | 12/2005 | Loshakove et al. |
| 2006/0020258 A1 | 1/2006 | Strauss et al. |
| 2006/0025812 A1 | 2/2006 | Shelton |
| 2006/0041188 A1 | 2/2006 | Dirusso et al. |
| 2006/0049229 A1 | 3/2006 | Milliman et al. |
| 2006/0052669 A1 | 3/2006 | Hart |
| 2006/0052825 A1 | 3/2006 | Ransick et al. |
| 2006/0089535 A1 | 4/2006 | Raz et al. |
| 2006/0100643 A1 | 5/2006 | Laufer et al. |
| 2006/0149306 A1 | 7/2006 | Hart et al. |
| 2006/0161050 A1 | 7/2006 | Butler et al. |
| 2006/0161185 A1 | 7/2006 | Saadat et al. |
| 2006/0173470 A1 | 8/2006 | Oray et al. |
| 2006/0180634 A1 | 8/2006 | Shelton et al. |
| 2006/0185682 A1 | 8/2006 | Marczyk |
| 2006/0201989 A1 | 9/2006 | Ojeda |
| 2006/0211919 A1 | 9/2006 | Wilk |
| 2006/0235368 A1 | 10/2006 | Oz |
| 2006/0241651 A1 | 10/2006 | Wilk |
| 2006/0252993 A1 | 11/2006 | Freed et al. |
| 2006/0258904 A1 | 11/2006 | Stefanchik et al. |
| 2006/0259073 A1 | 11/2006 | Miyamoto et al. |
| 2006/0271102 A1 | 11/2006 | Bosshard et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0027468 A1 | 2/2007 | Wales et al. |
| 2007/0043387 A1 | 2/2007 | Vargas et al. |
| 2007/0051375 A1 | 3/2007 | Milliman |
| 2007/0073341 A1 | 3/2007 | Smith et al. |
| 2007/0078484 A1 | 4/2007 | Talarico et al. |
| 2007/0080188 A1 | 4/2007 | Spence et al. |
| 2007/0080814 A1 | 4/2007 | Ellsworth et al. |
| 2007/0084897 A1 | 4/2007 | Shelton et al. |
| 2007/0093869 A1 | 4/2007 | Bloom et al. |
| 2007/0102472 A1 | 5/2007 | Shelton |
| 2007/0106317 A1 | 5/2007 | Shelton et al. |
| 2007/0118175 A1* | 5/2007 | Butler ............ A61B 17/0293 606/213 |
| 2007/0134251 A1 | 6/2007 | Ashkenazi et al. |
| 2007/0135803 A1 | 6/2007 | Belson |
| 2007/0170225 A1 | 7/2007 | Shelton et al. |
| 2007/0173687 A1 | 7/2007 | Shima et al. |
| 2007/0173813 A1 | 7/2007 | Odom |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0194079 A1 | 8/2007 | Hueil et al. |
| 2007/0194082 A1 | 8/2007 | Morgan et al. |
| 2007/0203510 A1 | 8/2007 | Bettuchi |
| 2007/0208359 A1 | 9/2007 | Hoffman |
| 2007/0213595 A1* | 9/2007 | Ravikumar ......... A61B 17/0218 600/217 |
| 2007/0225562 A1 | 9/2007 | Spivey et al. |
| 2007/0244471 A1 | 10/2007 | Malackowski |
| 2007/0246505 A1 | 10/2007 | Pace-Floridia et al. |
| 2007/0276409 A1 | 11/2007 | Ortiz et al. |
| 2007/0279011 A1 | 12/2007 | Jones et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0034649 A1* | 2/2008 | Sanchez ............ A01G 17/08 47/44 |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0086078 A1 | 4/2008 | Powell et al. |
| 2008/0091072 A1 | 4/2008 | Omori et al. |
| 2008/0108443 A1 | 5/2008 | Jinno et al. |
| 2008/0135600 A1 | 6/2008 | Hiranuma et al. |
| 2008/0140115 A1 | 6/2008 | Stopek |

(56) References Cited

U.S. PATENT DOCUMENTS

| | | |
|---|---|---|
| 2008/0154299 A1 | 6/2008 | Livneh |
| 2008/0154335 A1 | 6/2008 | Thrope et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0190989 A1 | 8/2008 | Crews et al. |
| 2008/0197167 A1 | 8/2008 | Viola et al. |
| 2008/0200762 A1 | 8/2008 | Stokes et al. |
| 2008/0200933 A1 | 8/2008 | Bakos et al. |
| 2008/0242939 A1 | 10/2008 | Johnston |
| 2008/0249536 A1 | 10/2008 | Stahler et al. |
| 2008/0255413 A1 | 10/2008 | Zemlok et al. |
| 2008/0257889 A1* | 10/2008 | Kovacevich ............ B65F 1/08 220/495.11 |
| 2008/0262654 A1 | 10/2008 | Omori et al. |
| 2008/0294179 A1 | 11/2008 | Balbierz et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2008/0315829 A1 | 12/2008 | Jones et al. |
| 2009/0001121 A1 | 1/2009 | Hess et al. |
| 2009/0001130 A1 | 1/2009 | Hess et al. |
| 2009/0005809 A1 | 1/2009 | Hess et al. |
| 2009/0012534 A1 | 1/2009 | Madhani et al. |
| 2009/0048589 A1 | 2/2009 | Takashino et al. |
| 2009/0078736 A1 | 3/2009 | Van Lue |
| 2009/0090763 A1 | 4/2009 | Zemlok et al. |
| 2009/0099876 A1 | 4/2009 | Whitman |
| 2009/0143789 A1* | 6/2009 | Houser ............ A61B 17/0057 606/142 |
| 2009/0149871 A9 | 6/2009 | Kagan et al. |
| 2009/0188964 A1 | 7/2009 | Orlov |
| 2009/0194547 A1* | 8/2009 | Krueger ................ A47G 19/30 220/694 |
| 2009/0198272 A1 | 8/2009 | Kerver et al. |
| 2009/0204108 A1 | 8/2009 | Steffen |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0234293 A1* | 9/2009 | Albrecht ............ A61B 17/3421 604/167.02 |
| 2009/0242610 A1 | 10/2009 | Shelton, IV et al. |
| 2009/0255550 A1* | 10/2009 | Shyu ................. A45D 8/00 132/275 |
| 2009/0255974 A1 | 10/2009 | Viola |
| 2009/0292283 A1 | 11/2009 | Odom |
| 2009/0308907 A1 | 12/2009 | Nalagatla et al. |
| 2010/0069942 A1 | 3/2010 | Shelton, IV |
| 2010/0087713 A1* | 4/2010 | Eliash .................. A61B 17/02 600/206 |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0193566 A1 | 8/2010 | Scheib et al. |
| 2010/0222901 A1 | 9/2010 | Swayze et al. |
| 2010/0237212 A1* | 9/2010 | Arcaro .................. D06F 55/00 248/316.7 |
| 2010/0292540 A1 | 11/2010 | Hess et al. |
| 2010/0312261 A1 | 12/2010 | Suzuki et al. |
| 2011/0006101 A1 | 1/2011 | Hall et al. |
| 2011/0011916 A1 | 1/2011 | Levine |
| 2011/0022032 A1 | 1/2011 | Zemlok et al. |
| 2011/0023904 A1* | 2/2011 | Hsu .................. A45D 8/34 132/276 |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0060363 A1 | 3/2011 | Hess et al. |
| 2011/0071356 A1 | 3/2011 | Edwards |
| 2011/0087276 A1 | 4/2011 | Bedi et al. |
| 2011/0091515 A1 | 4/2011 | Zilberman et al. |
| 2011/0114697 A1 | 5/2011 | Baxter, III et al. |
| 2011/0118706 A1 | 5/2011 | Gingras et al. |
| 2011/0125176 A1 | 5/2011 | Yates et al. |
| 2011/0130624 A1* | 6/2011 | Hamman ............ A61B 17/0293 600/36 |
| 2011/0147433 A1 | 6/2011 | Shelton, IV et al. |
| 2011/0163146 A1 | 7/2011 | Ortiz et al. |
| 2011/0172495 A1* | 7/2011 | Armstrong ......... A61B 17/0218 600/233 |
| 2011/0174861 A1 | 7/2011 | Shelton, IV et al. |
| 2011/0192882 A1 | 8/2011 | Hess et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0290856 A1 | 12/2011 | Shelton, IV et al. |
| 2011/0293690 A1 | 12/2011 | Griffin et al. |
| 2011/0295295 A1 | 12/2011 | Shelton, IV et al. |
| 2012/0029272 A1 | 2/2012 | Shelton, IV et al. |
| 2012/0074200 A1 | 3/2012 | Schmid et al. |
| 2012/0080336 A1 | 4/2012 | Shelton, IV et al. |
| 2012/0080344 A1 | 4/2012 | Shelton, IV |
| 2012/0080478 A1 | 4/2012 | Morgan et al. |
| 2012/0080498 A1 | 4/2012 | Shelton, IV et al. |
| 2012/0109186 A1 | 5/2012 | Parrott et al. |
| 2012/0125792 A1 | 5/2012 | Cassivi |
| 2012/0175398 A1 | 7/2012 | Sandborn et al. |
| 2012/0199602 A1 | 8/2012 | Jordan et al. |
| 2012/0234895 A1 | 9/2012 | O'Connor et al. |
| 2012/0234897 A1 | 9/2012 | Shelton, IV et al. |
| 2012/0248169 A1 | 10/2012 | Widenhouse et al. |
| 2012/0283707 A1 | 11/2012 | Giordano et al. |
| 2012/0289979 A1 | 11/2012 | Eskaros et al. |
| 2012/0292367 A1 | 11/2012 | Morgan et al. |
| 2012/0298722 A1 | 11/2012 | Hess et al. |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026209 A1 | 1/2013 | Mozdzierz et al. |
| 2013/0026210 A1 | 1/2013 | Shelton, IV et al. |
| 2013/0030253 A1 | 1/2013 | Titus |
| 2013/0085339 A1 | 4/2013 | Jaworek et al. |
| 2013/0087597 A1 | 4/2013 | Shelton, IV et al. |
| 2013/0098970 A1 | 4/2013 | Racenet et al. |
| 2013/0116669 A1 | 5/2013 | Shelton, IV et al. |
| 2013/0153641 A1 | 6/2013 | Shelton, IV et al. |
| 2013/0175317 A1 | 7/2013 | Yates et al. |
| 2013/0233906 A1 | 9/2013 | Hess et al. |
| 2013/0256373 A1 | 10/2013 | Schmid et al. |
| 2013/0256380 A1 | 10/2013 | Schmid et al. |
| 2013/0270322 A1 | 10/2013 | Scheib et al. |
| 2013/0331867 A1 | 12/2013 | Reeser et al. |
| 2013/0334283 A1 | 12/2013 | Swayze et al. |
| 2013/0334285 A1 | 12/2013 | Swayze et al. |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005718 A1 | 1/2014 | Shelton, IV et al. |
| 2014/0014704 A1 | 1/2014 | Onukuri et al. |
| 2014/0014705 A1 | 1/2014 | Baxter, III |
| 2014/0039549 A1 | 2/2014 | Belsky et al. |
| 2014/0048580 A1 | 2/2014 | Merchant et al. |
| 2014/0107640 A1 | 4/2014 | Yates et al. |
| 2014/0151433 A1 | 6/2014 | Shelton, IV et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175152 A1 | 6/2014 | Hess et al. |
| 2014/0188159 A1 | 7/2014 | Steege |
| 2014/0194698 A1* | 7/2014 | Melsheimer ........ A61B 17/0281 600/233 |
| 2014/0200409 A1* | 7/2014 | Green .................. A61B 17/083 600/208 |
| 2014/0224857 A1 | 8/2014 | Schmid |

(56) References Cited

U.S. PATENT DOCUMENTS

| | | |
|---|---|---|
| 2014/0243865 A1 | 8/2014 | Swayze et al. |
| 2014/0246475 A1 | 9/2014 | Hall et al. |
| 2014/0249557 A1 | 9/2014 | Koch et al. |
| 2014/0263541 A1 | 9/2014 | Leimbach et al. |
| 2014/0263552 A1 | 9/2014 | Hall et al. |
| 2014/0284371 A1 | 9/2014 | Morgan et al. |
| 2014/0291379 A1 | 10/2014 | Schellin et al. |
| 2014/0291383 A1 | 10/2014 | Spivey et al. |
| 2014/0299648 A1 | 10/2014 | Shelton, IV et al. |
| 2014/0303645 A1 | 10/2014 | Morgan et al. |
| 2015/0012006 A1 | 1/2015 | Hausen et al. |
| 2015/0053737 A1 | 2/2015 | Leimbach et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0297222 A1 | 10/2015 | Huitema et al. |
| 2015/0297223 A1 | 10/2015 | Huitema et al. |
| 2015/0297225 A1 | 10/2015 | Huitema et al. |
| 2015/0297228 A1 | 10/2015 | Huitema et al. |
| 2015/0297233 A1 | 10/2015 | Huitema et al. |
| 2015/0313594 A1 | 11/2015 | Shelton, IV et al. |
| 2016/0066913 A1 | 3/2016 | Swayze et al. |
| 2016/0095733 A1* | 4/2016 | Sharma .................. A61F 2/04 600/424 |
| 2016/0113653 A1 | 4/2016 | Zingman |
| 2016/0249910 A1 | 9/2016 | Shelton, IV et al. |
| 2016/0256154 A1 | 9/2016 | Shelton, IV et al. |
| 2016/0256160 A1 | 9/2016 | Shelton, IV et al. |
| 2017/0007229 A1 | 1/2017 | Widenhouse et al. |
| 2017/0027572 A1 | 2/2017 | Nalagatla et al. |
| 2017/0056000 A1 | 3/2017 | Nalagatla et al. |
| 2017/0056065 A1* | 3/2017 | Do .................. A61B 17/3423 |
| 2017/0119388 A1 | 5/2017 | Kostrzewski |
| 2017/0224331 A1 | 8/2017 | Worthington et al. |
| 2017/0224332 A1 | 8/2017 | Hunter et al. |
| 2017/0224334 A1 | 8/2017 | Worthington et al. |
| 2017/0224335 A1 | 8/2017 | Weaner et al. |
| 2017/0231627 A1 | 8/2017 | Shelton, IV et al. |
| 2017/0231628 A1 | 8/2017 | Shelton, IV et al. |
| 2017/0258540 A1 | 9/2017 | Blatt |
| 2017/0281164 A1 | 10/2017 | Harris et al. |
| 2017/0281167 A1 | 10/2017 | Shelton, IV et al. |
| 2017/0281169 A1 | 10/2017 | Harris et al. |
| 2017/0281171 A1 | 10/2017 | Shelton, IV et al. |
| 2017/0281173 A1 | 10/2017 | Shelton, IV et al. |
| 2017/0281174 A1 | 10/2017 | Harris et al. |
| 2017/0281186 A1 | 10/2017 | Shelton, IV et al. |
| 2017/0281187 A1 | 10/2017 | Shelton, IV et al. |
| 2017/0281189 A1 | 10/2017 | Nalagatla et al. |
| 2018/0325508 A1 | 11/2018 | Aronhalt et al. |
| 2018/0343997 A1* | 12/2018 | Grant .................. A45D 8/34 |
| 2019/0021718 A1 | 1/2019 | Aronhalt et al. |
| 2019/0183508 A1 | 6/2019 | Shelton, IV et al. |
| 2020/0077762 A1* | 3/2020 | Ahrens .................. A45D 8/34 |

FOREIGN PATENT DOCUMENTS

| | | | |
|---|---|---|---|
| CN | 1163558 | A | 10/1997 |
| CN | 2488482 | Y | 5/2002 |
| CN | 2686539 | Y | 3/2005 |
| CN | 1634601 | A | 7/2005 |
| CN | 2716900 | Y | 8/2005 |
| CN | 2738962 | Y | 11/2005 |
| CN | 2868212 | Y | 2/2007 |
| CN | 202313540 | U | 7/2012 |
| DE | 273689 | C | 5/1914 |
| DE | 1775926 | A | 1/1972 |
| DE | 3036217 | A1 | 4/1982 |
| DE | 3210466 | A1 | 9/1983 |
| DE | 3709067 | A1 | 9/1988 |
| DE | 19851291 | A1 | 1/2000 |
| DE | 19924311 | A1 | 11/2000 |
| DE | 20016423 | U1 | 2/2001 |
| DE | 20112837 | U1 | 10/2001 |
| DE | 20121753 | U1 | 4/2003 |
| DE | 10314072 | A1 | 10/2004 |
| DE | 202007003114 | U1 | 6/2007 |
| EP | 0000756 | A1 | 2/1979 |
| EP | 0122046 | A1 | 10/1984 |
| EP | 0129442 | B1 | 11/1987 |
| EP | 0169044 | B1 | 6/1991 |
| EP | 0548998 | A1 | 6/1993 |
| EP | 0594148 | A1 | 4/1994 |
| EP | 0646357 | A1 | 4/1995 |
| EP | 0505036 | B1 | 5/1995 |
| EP | 0669104 | A1 | 8/1995 |
| EP | 0705571 | A1 | 4/1996 |
| EP | 0528478 | B1 | 5/1996 |
| EP | 0770355 | A1 | 5/1997 |
| EP | 0625335 | B1 | 11/1997 |
| EP | 0879742 | A1 | 11/1998 |
| EP | 0650701 | B1 | 3/1999 |
| EP | 0923907 | A1 | 6/1999 |
| EP | 0484677 | B2 | 7/2000 |
| EP | 1034747 | A1 | 9/2000 |
| EP | 1034748 | A1 | 9/2000 |
| EP | 1053719 | A1 | 11/2000 |
| EP | 1055399 | A1 | 11/2000 |
| EP | 1055400 | A1 | 11/2000 |
| EP | 1080694 | A1 | 3/2001 |
| EP | 1090592 | A1 | 4/2001 |
| EP | 1095627 | A1 | 5/2001 |
| EP | 0806914 | B1 | 9/2001 |
| EP | 1284120 | A1 | 2/2003 |
| EP | 0869742 | B1 | 5/2003 |
| EP | 1374788 | A1 | 1/2004 |
| EP | 1407719 | A2 | 4/2004 |
| EP | 0996378 | B1 | 6/2004 |
| EP | 1486172 | A1 | 12/2004 |
| EP | 1157666 | B1 | 9/2005 |
| EP | 0880338 | B1 | 10/2005 |
| EP | 1158917 | B1 | 11/2005 |
| EP | 1344498 | B1 | 11/2005 |
| EP | 1330989 | B1 | 12/2005 |
| EP | 1632191 | A2 | 3/2006 |
| EP | 1082944 | B1 | 5/2006 |
| EP | 1253866 | B1 | 7/2006 |
| EP | 1285633 | B1 | 12/2006 |
| EP | 1011494 | B1 | 1/2007 |
| EP | 1767163 | A1 | 3/2007 |
| EP | 1837041 | A1 | 9/2007 |
| EP | 0922435 | B1 | 10/2007 |
| EP | 1599146 | B1 | 10/2007 |
| EP | 1330201 | B1 | 6/2008 |
| EP | 2039302 | A2 | 3/2009 |
| EP | 1719461 | B1 | 6/2009 |
| EP | 1769754 | B1 | 6/2010 |
| EP | 1627605 | B1 | 12/2010 |
| EP | 2316345 | A1 | 5/2011 |
| EP | 1962711 | B1 | 2/2012 |
| EP | 2486862 | A2 | 8/2012 |
| EP | 2517638 | A1 | 10/2012 |
| EP | 2649948 | A1 | 10/2013 |
| EP | 2649949 | A1 | 10/2013 |
| FR | 459743 | A | 11/1913 |
| FR | 999646 | A | 2/1952 |
| FR | 1112936 | A | 3/1956 |
| FR | 2598905 | A1 | 11/1987 |
| FR | 2765794 | A1 | 1/1999 |
| FR | 2815842 | A1 | 5/2002 |
| GB | 939929 | A | 10/1963 |
| GB | 1210522 | A | 10/1970 |
| GB | 1217159 | A | 12/1970 |
| GB | 1339394 | A | 12/1973 |
| GB | 2024012 | A | 1/1980 |
| GB | 2109241 | A | 6/1983 |
| GB | 2272159 | A | 5/1994 |
| GB | 2336214 | A | 10/1999 |
| GR | 930100110 | A | 11/1993 |
| JP | S4711908 | Y1 | 5/1972 |
| JP | S5033988 | U | 4/1975 |
| JP | S56112235 | A | 9/1981 |

(56) References Cited

FOREIGN PATENT DOCUMENTS

| | | |
|---|---|---|
| JP | S62170011 U | 10/1987 |
| JP | H04215747 A | 8/1992 |
| JP | H04131860 U | 12/1992 |
| JP | H0584252 A | 4/1993 |
| JP | H05123325 A | 5/1993 |
| JP | H0630945 A | 2/1994 |
| JP | H06237937 A | 8/1994 |
| JP | H06327684 A | 11/1994 |
| JP | H07124166 A | 5/1995 |
| JP | H07255735 A | 10/1995 |
| JP | H07285089 A | 10/1995 |
| JP | H0833642 A | 2/1996 |
| JP | H08164141 A | 6/1996 |
| JP | H08182684 A | 7/1996 |
| JP | H08507708 A | 8/1996 |
| JP | H08229050 A | 9/1996 |
| JP | H10118090 A | 5/1998 |
| JP | H10151137 A | 6/1998 |
| JP | 2000014632 A | 1/2000 |
| JP | 2000033071 A | 2/2000 |
| JP | 2000112002 A | 4/2000 |
| JP | 2000166932 A | 6/2000 |
| JP | 2000171730 A | 6/2000 |
| JP | 2000287987 A | 10/2000 |
| JP | 2000325303 A | 11/2000 |
| JP | 2001087272 A | 4/2001 |
| JP | 2001514541 A | 9/2001 |
| JP | 2001276091 A | 10/2001 |
| JP | 2002051974 A | 2/2002 |
| JP | 2002085415 A | 3/2002 |
| JP | 2002143078 A | 5/2002 |
| JP | 2002528161 A | 9/2002 |
| JP | 2002314298 A | 10/2002 |
| JP | 2003135473 A | 5/2003 |
| JP | 2003521301 A | 7/2003 |
| JP | 2004147701 A | 5/2004 |
| JP | 2004162035 A | 6/2004 |
| JP | 2004229976 A | 8/2004 |
| JP | 2005080702 A | 3/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005328882 A | 12/2005 |
| JP | 2005335432 A | 12/2005 |
| JP | 2005342267 A | 12/2005 |
| JP | 2006187649 A | 7/2006 |
| JP | 2006281405 A | 10/2006 |
| JP | 2006346445 A | 12/2006 |
| JP | 2009507526 A | 2/2009 |
| JP | 2009189838 A | 8/2009 |
| JP | 2009539420 A | 11/2009 |
| JP | 2010069310 A | 4/2010 |
| JP | 2010098844 A | 4/2010 |
| KR | 20110003229 A | 1/2011 |
| RU | 1814161 C | 5/1993 |
| RU | 2008830 C1 | 3/1994 |
| RU | 2052979 C1 | 1/1996 |
| RU | 2098025 C1 | 12/1997 |
| RU | 2141279 C1 | 11/1999 |
| RU | 2144791 C1 | 1/2000 |
| RU | 2181566 C2 | 4/2002 |
| RU | 2187249 C2 | 8/2002 |
| RU | 32984 U1 | 10/2003 |
| RU | 2225170 C2 | 3/2004 |
| RU | 42750 U1 | 12/2004 |
| RU | 61114 U1 | 2/2007 |
| SU | 189517 A | 1/1967 |
| SU | 328636 A | 9/1972 |
| SU | 674747 A1 | 7/1979 |
| SU | 1009439 A | 4/1983 |
| SU | 1333319 A2 | 8/1987 |
| SU | 1377053 A1 | 2/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| SU | 1814161 A1 | 5/1993 |
| WO | WO-9315648 A1 | 8/1993 |
| WO | WO-9420030 A1 | 9/1994 |
| WO | WO-9517855 A1 | 7/1995 |
| WO | WO-9520360 A1 | 8/1995 |
| WO | WO-9623448 A1 | 8/1996 |
| WO | WO-9635464 A1 | 11/1996 |
| WO | WO-9639086 A1 | 12/1996 |
| WO | WO-9639088 A1 | 12/1996 |
| WO | WO-9724073 A1 | 7/1997 |
| WO | WO-9734533 A1 | 9/1997 |
| WO | WO-9903407 A1 | 1/1999 |
| WO | WO-9903409 A1 | 1/1999 |
| WO | WO-9948430 A1 | 9/1999 |
| WO | WO-0024322 A1 | 5/2000 |
| WO | WO-0024330 A1 | 5/2000 |
| WO | WO-0053112 A2 | 9/2000 |
| WO | WO-0057796 A1 | 10/2000 |
| WO | WO-0105702 A1 | 1/2001 |
| WO | WO-0154594 A1 | 8/2001 |
| WO | WO-0158371 A1 | 8/2001 |
| WO | WO-0162164 A2 | 8/2001 |
| WO | WO-0162169 A2 | 8/2001 |
| WO | WO-0191646 A1 | 12/2001 |
| WO | WO-0219932 A1 | 3/2002 |
| WO | WO-0226143 A1 | 4/2002 |
| WO | WO-0236028 A1 | 5/2002 |
| WO | WO-02065933 A2 | 8/2002 |
| WO | WO-03055402 A1 | 7/2003 |
| WO | WO-03094747 A1 | 11/2003 |
| WO | WO-03079909 A3 | 3/2004 |
| WO | WO-2004019803 A1 | 3/2004 |
| WO | WO-2004032783 A1 | 4/2004 |
| WO | WO-2004047626 A1 | 6/2004 |
| WO | WO-2004047653 A2 | 6/2004 |
| WO | WO-2004056277 A1 | 7/2004 |
| WO | WO-2004078050 A2 | 9/2004 |
| WO | WO-2004078051 A2 | 9/2004 |
| WO | WO-2004096015 A2 | 11/2004 |
| WO | WO-2006044581 A2 | 4/2006 |
| WO | WO-2006051252 A1 | 5/2006 |
| WO | WO-2006059067 A1 | 6/2006 |
| WO | WO-2006085389 A1 | 8/2006 |
| WO | WO-2007074430 A1 | 7/2007 |
| WO | WO-2007137304 A2 | 11/2007 |
| WO | WO-2007142625 A2 | 12/2007 |
| WO | WO-2008021969 A2 | 2/2008 |
| WO | WO-2008089404 A2 | 7/2008 |
| WO | WO-2009067649 A2 | 5/2009 |
| WO | WO-2009091497 A2 | 7/2009 |
| WO | WO-2011008672 A2 | 1/2011 |
| WO | WO-2011044343 A2 | 4/2011 |
| WO | WO-2012006306 A2 | 1/2012 |
| WO | WO-2012044606 A2 | 4/2012 |
| WO | WO-2013087092 A1 | 6/2013 |

OTHER PUBLICATIONS

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

Biomedical Coatings, Fort Wayne Metals, Research Products Corporation, obtained online at www.fwmetals.com on Jun. 21, 2010 (1 page).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

(56) References Cited

OTHER PUBLICATIONS

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
Covidien Brochure, "Endo GIA™ Reloads with Tri-Staple™ Technology and Endo GIA™ Ultra Universal Staplers," (2010), 2 pages.
Covidien Brochure, "Endo GIA™ Reloads with Tri-Staple™ Technology," (2010), 1 page.
Covidien Brochure, "Endo GIA™ Black Reload with Tri-Staple™ Technology," (2012), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Covidien Brochure, "Endo GIA™ Ultra Universal Stapler," (2010), 2 pages.
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Byrne et al., "Molecular Imprinting Within Hydrogels," Advanced Drug Delivery Reviews, 54 (2002) pp. 149-161.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
Peppas, Editor "Hydrogels in Medicine and Pharmacy," vol. I, Fundamentals, CRC Press, 1986.
Matsuda, "Thermodynamics of Formation of Porous Polymeric Membrane from Solutions," Polymer Journal, vol. 23, No. 5, pp. 435-444 (1991).
Young, "Microcellular foams via phase separation," Journal of Vacuum Science & Technology A 4(3), (May/Jun. 1986).
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
The Sodem Aseptic Battery Transfer Kit, Sodem Systems, 2000, 3 pages.
Chen et al., "Elastomeric Biomaterials for Tissue Engineering," Progress in Polymer Science 38 (2013), pp. 584-671.
Pitt et al., "Attachment of Hyaluronan to Metallic Surfaces," J. Biomed. Mater. Res. 68A: pp. 95-106, 2004.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Solorio et al., "Gelatin Microspheres Crosslinked with Genipin for Local Delivery of Growth Factors," J. Tissue Eng. Regen. Med. (2010), 4(7): pp. 514-523.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Seils et al., Covidien Summary: Clinical Study "UCONN Biodynamics: Final Report on Results," (2 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien Brochure "iDrive™ Ultra Powered Stapling System," (6 pages).
Indian Standard: Automotive Vehicles—Brakes and Braking Systems (IS 11852-1:2001), Mar. 1, 2001.
Zhang et al.; "Viscoelastic Properties of Wood Materials Characterized by Nanoindentation Experiments"; Dec. 20, 2011 (Year: 2011).
Batista et al.; "Evaluation of Weather Influence on Mechanical and Viscoelastic Properties of Polyetherimide/Carbon Fiber Composites"; Apr. 30, 2013 (Year: 2013).
L. Edward Parkman, III; "Viscoelastic Effects on a Polyetherimide Cylinder with Constant Radial Deformation"; May 2015; (Year: 2015).

* cited by examiner

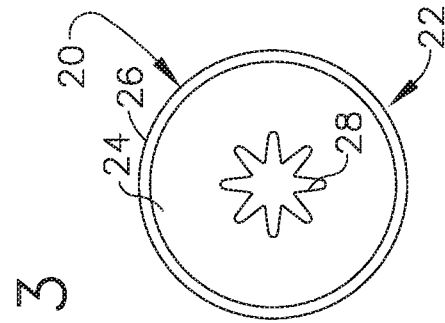
FIG. 3
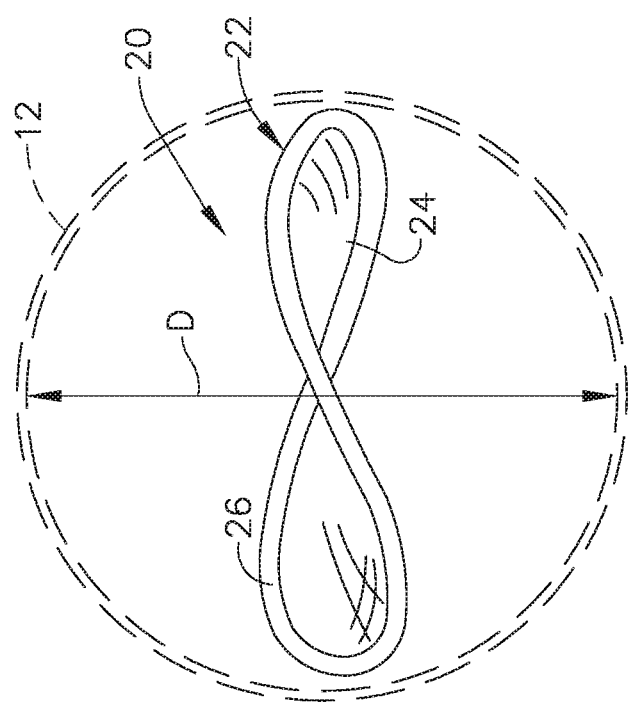
FIG. 4
FIG. 5
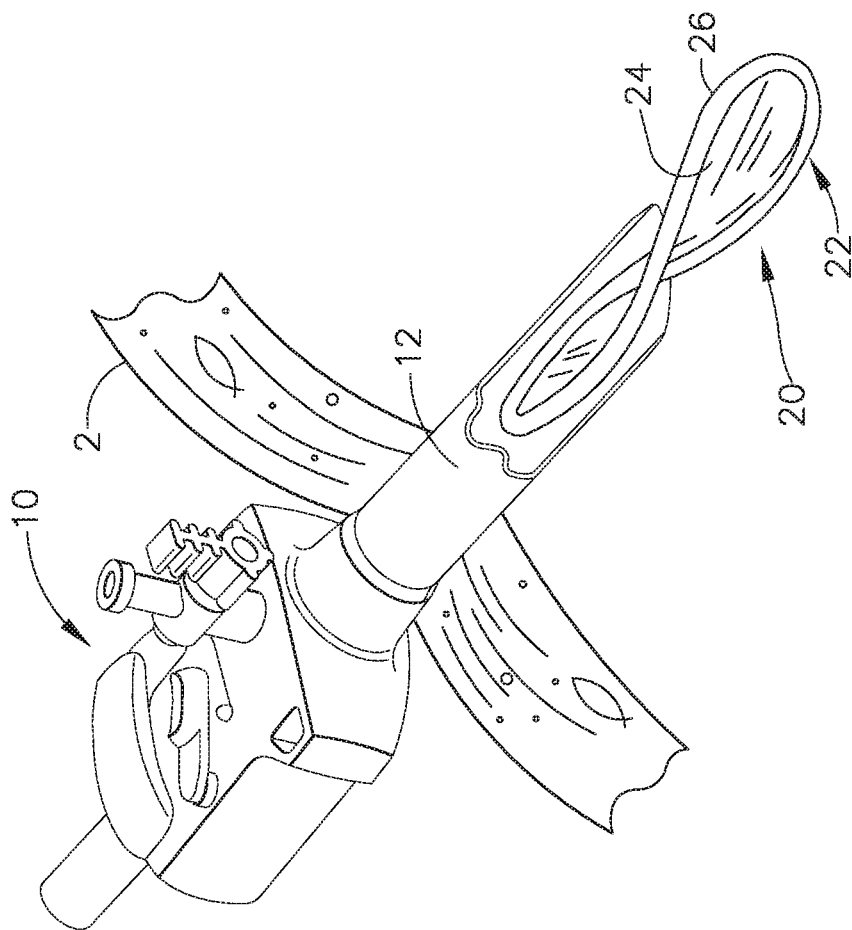
FIG. 2

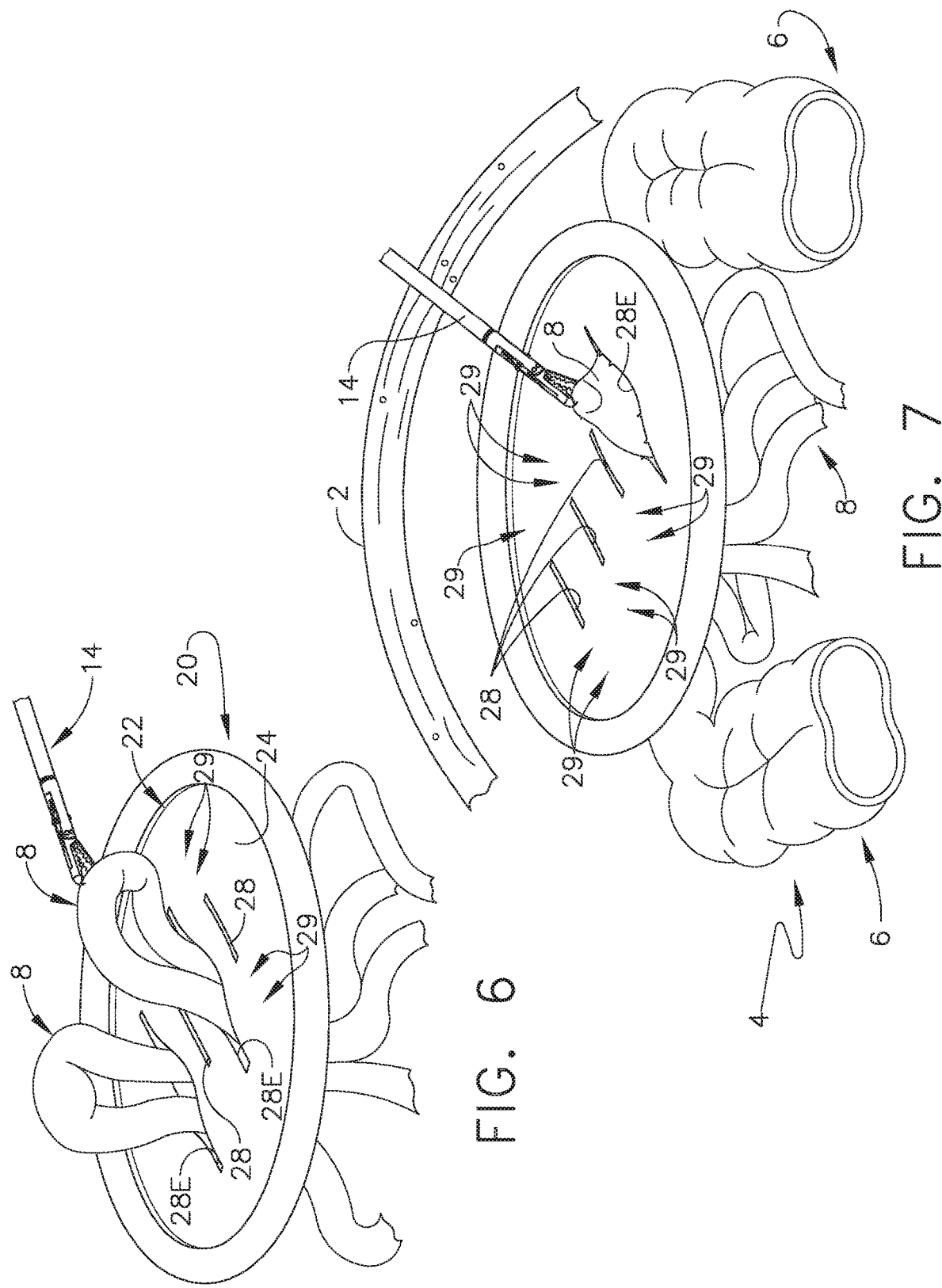

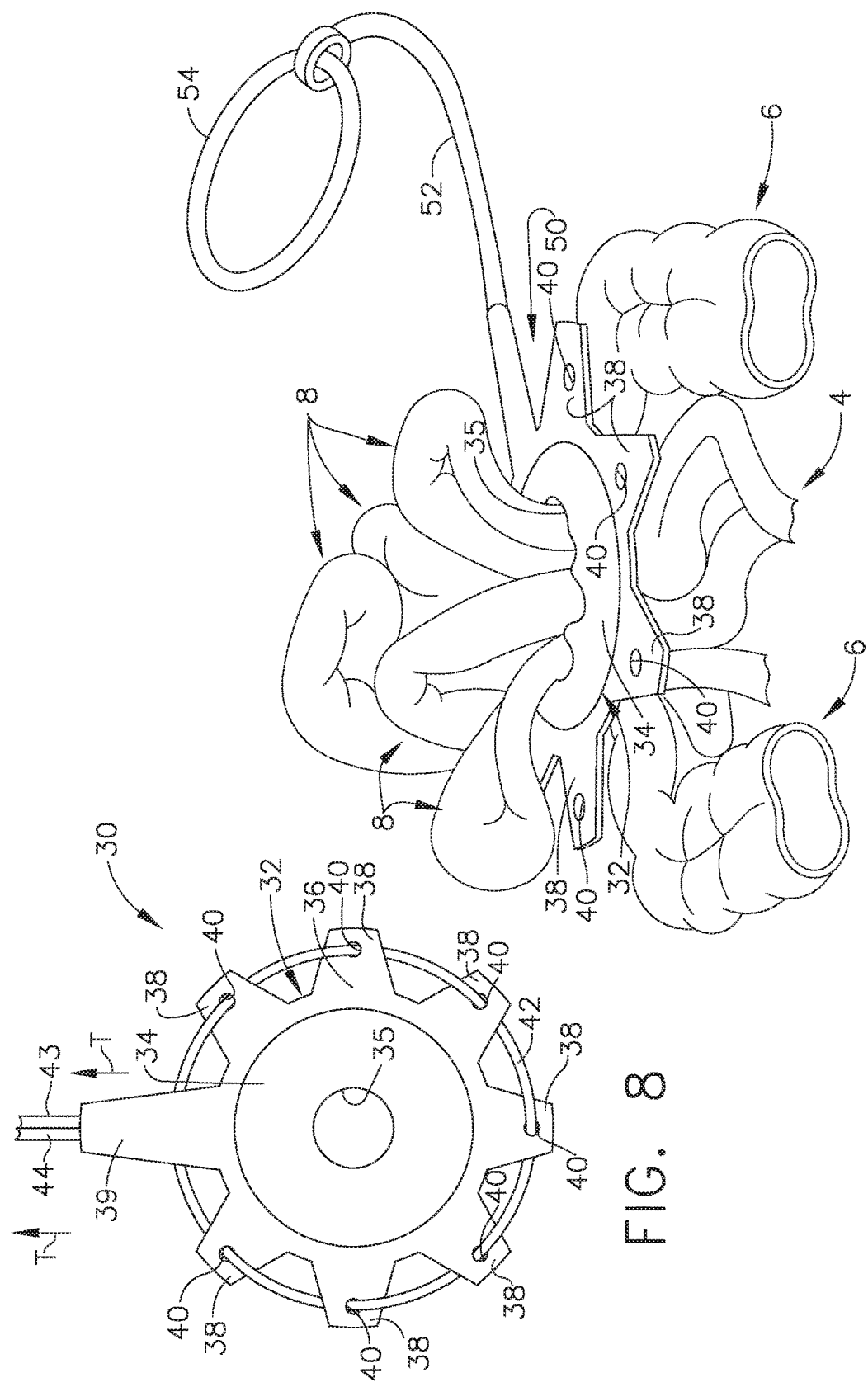

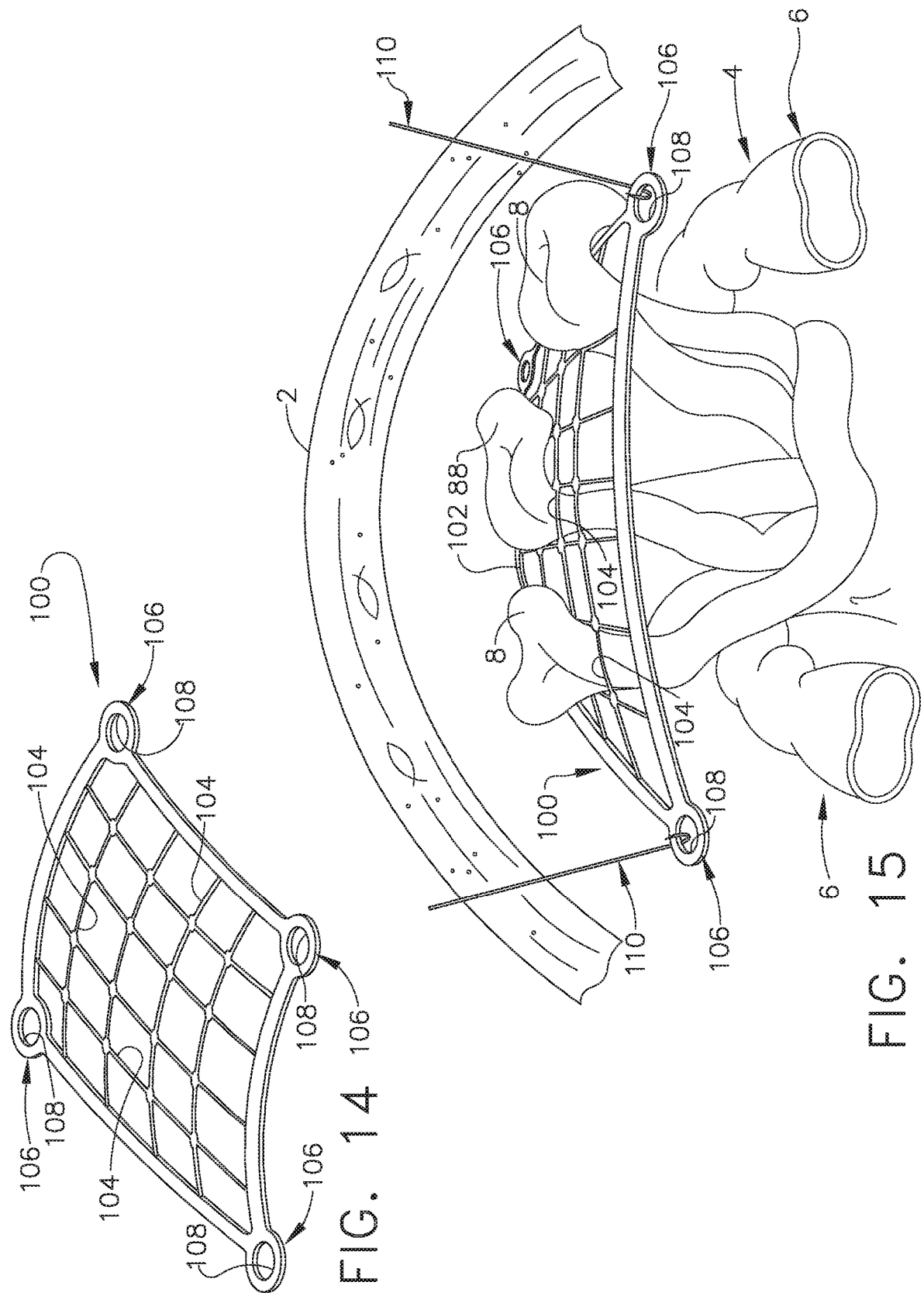

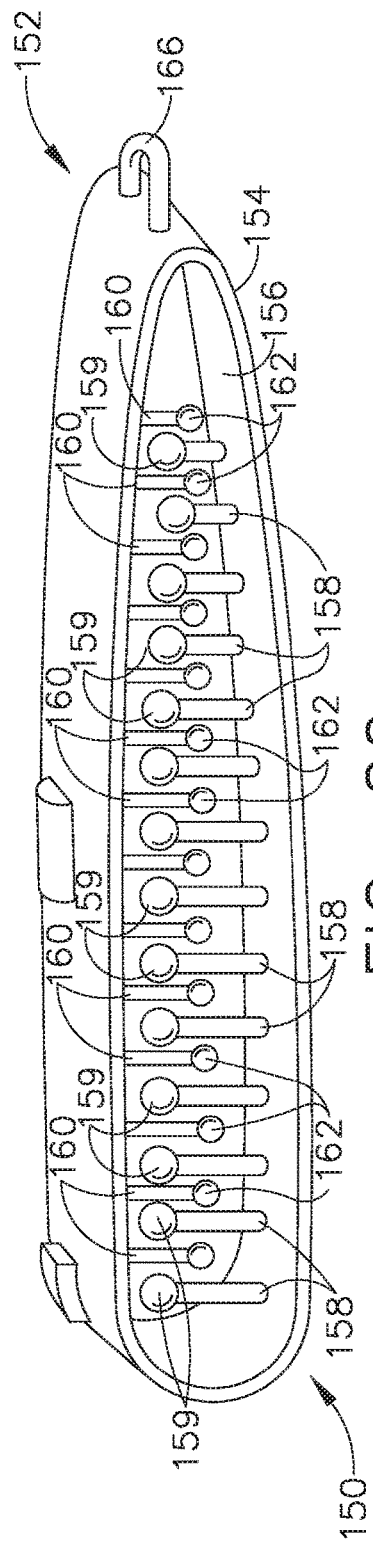
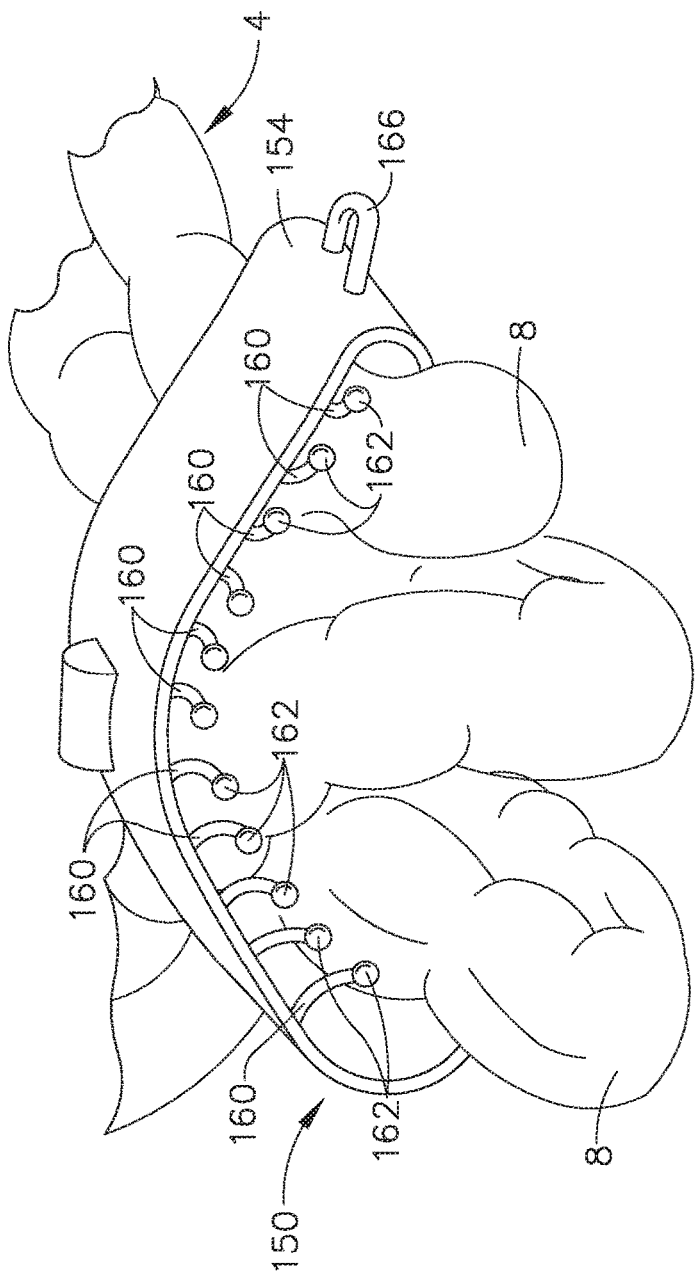

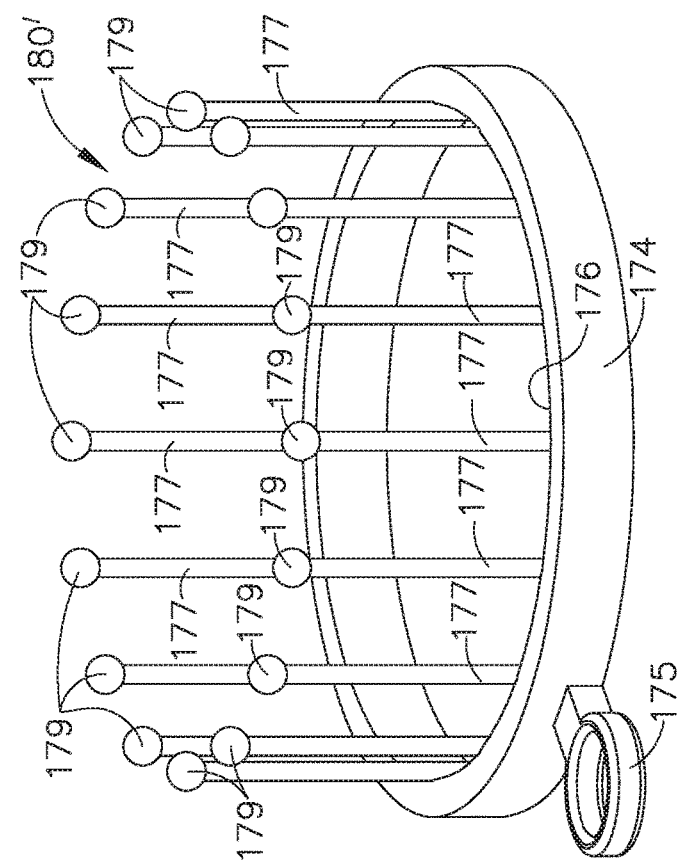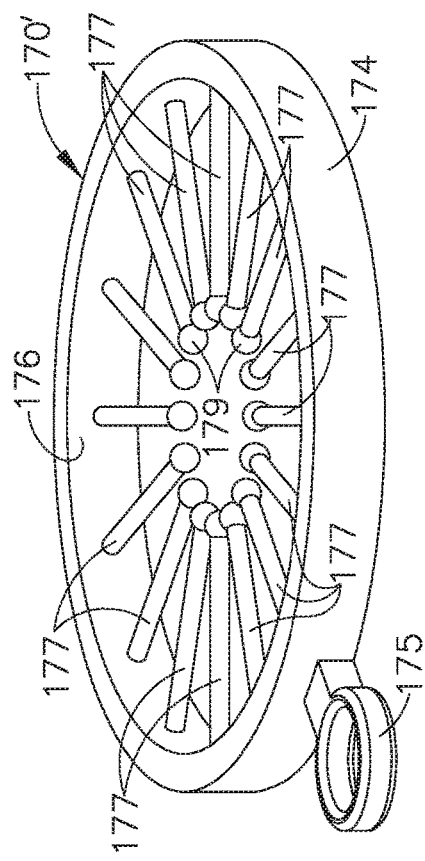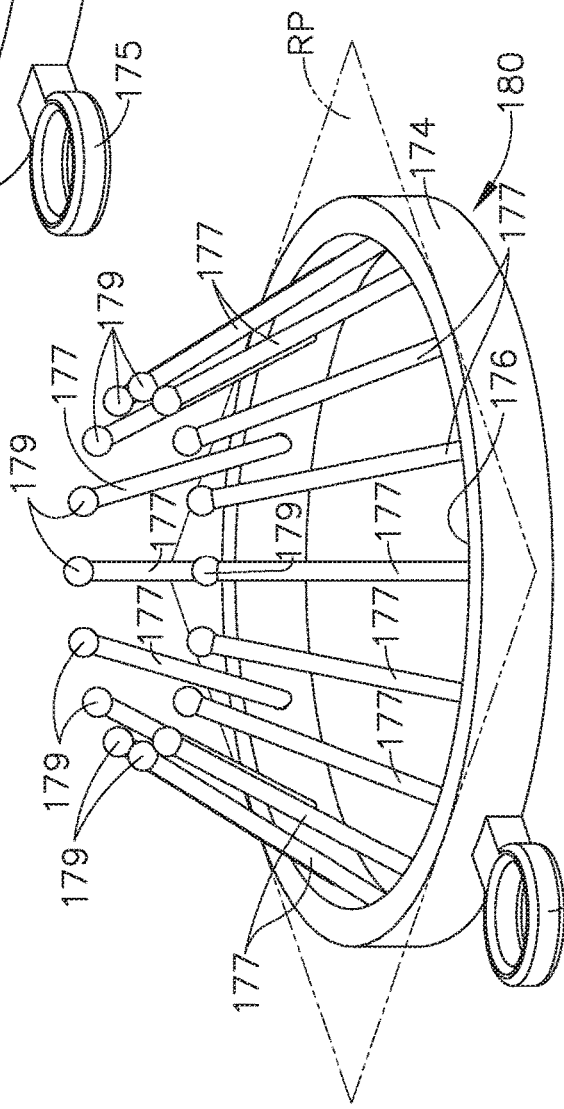

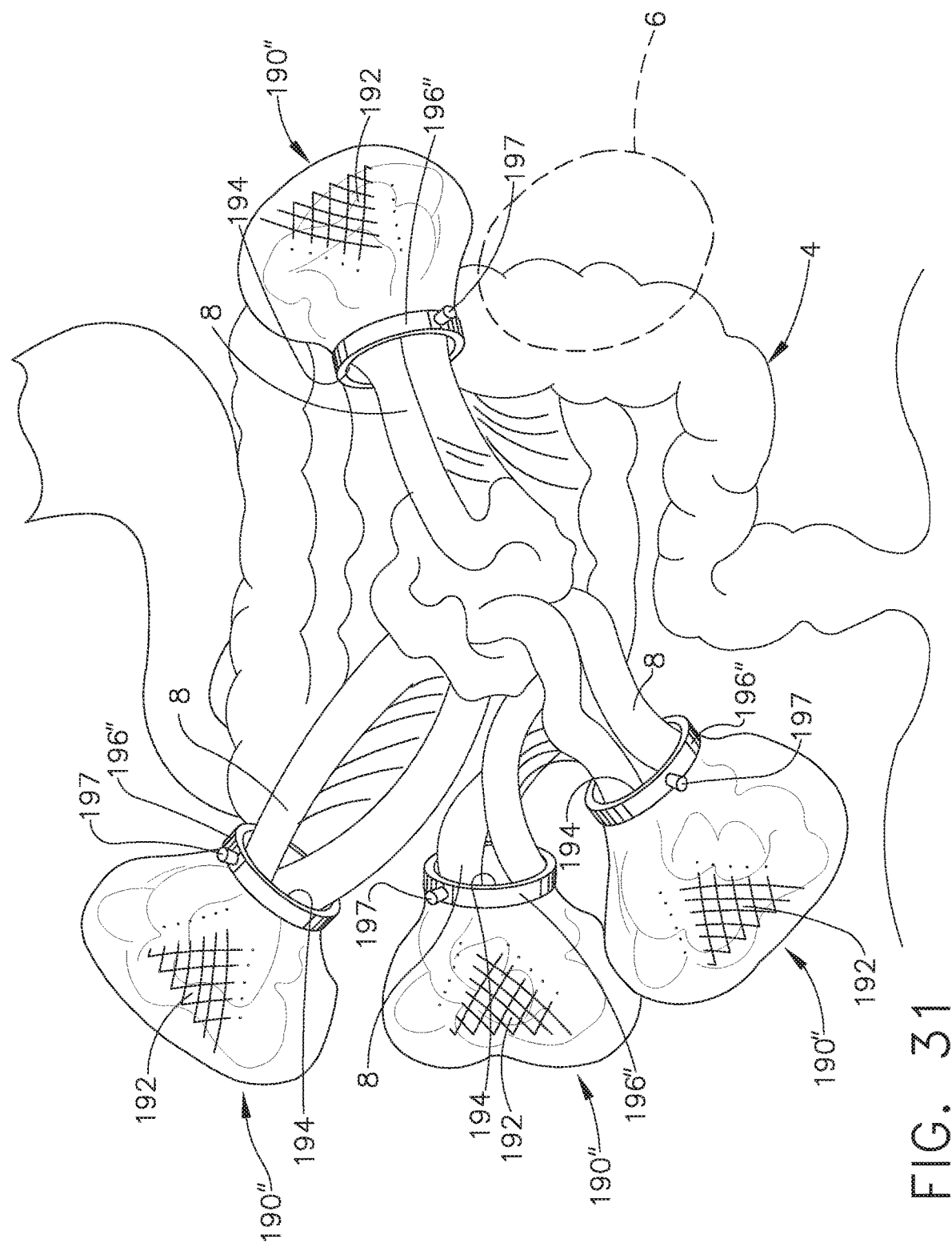

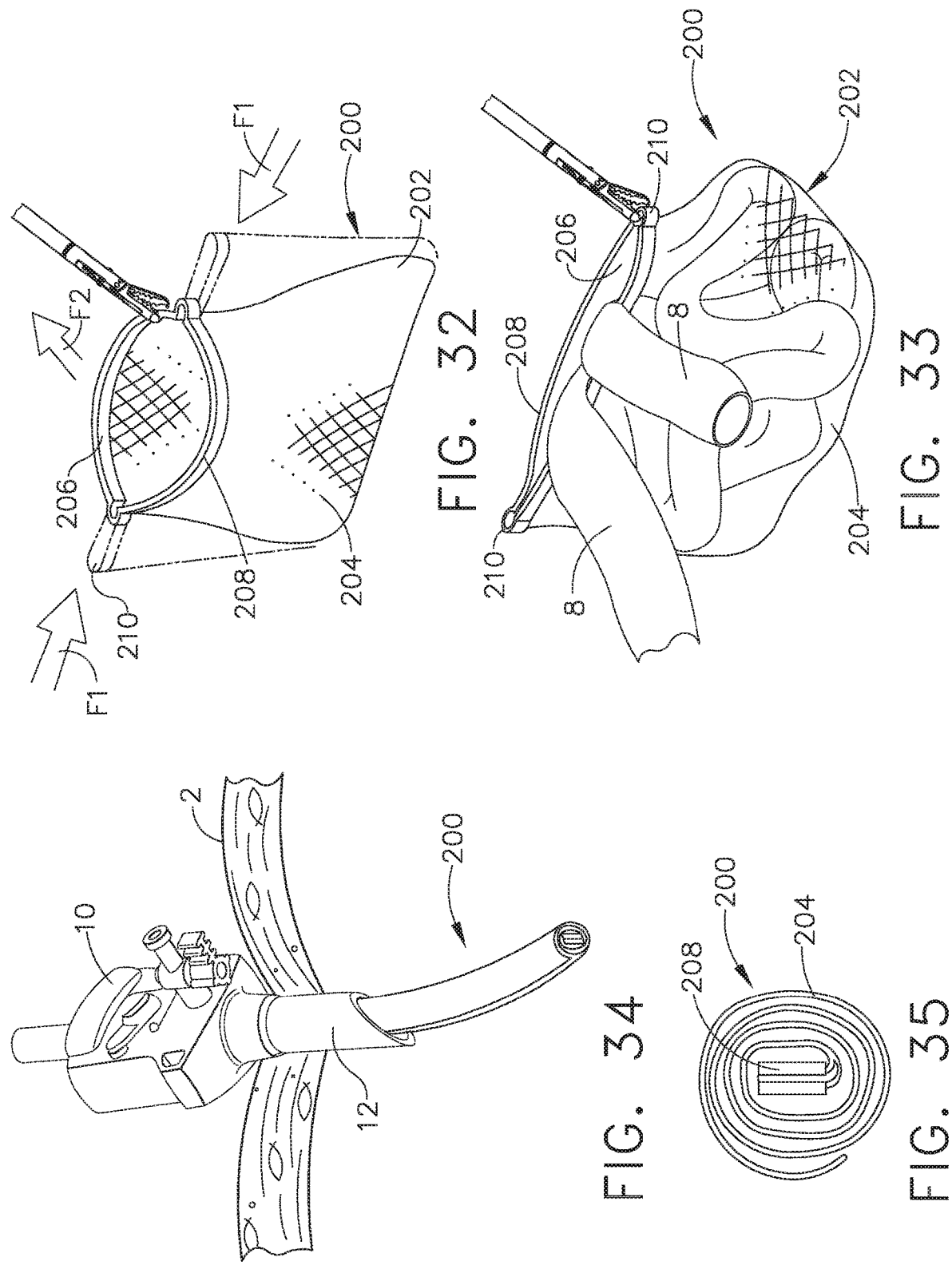

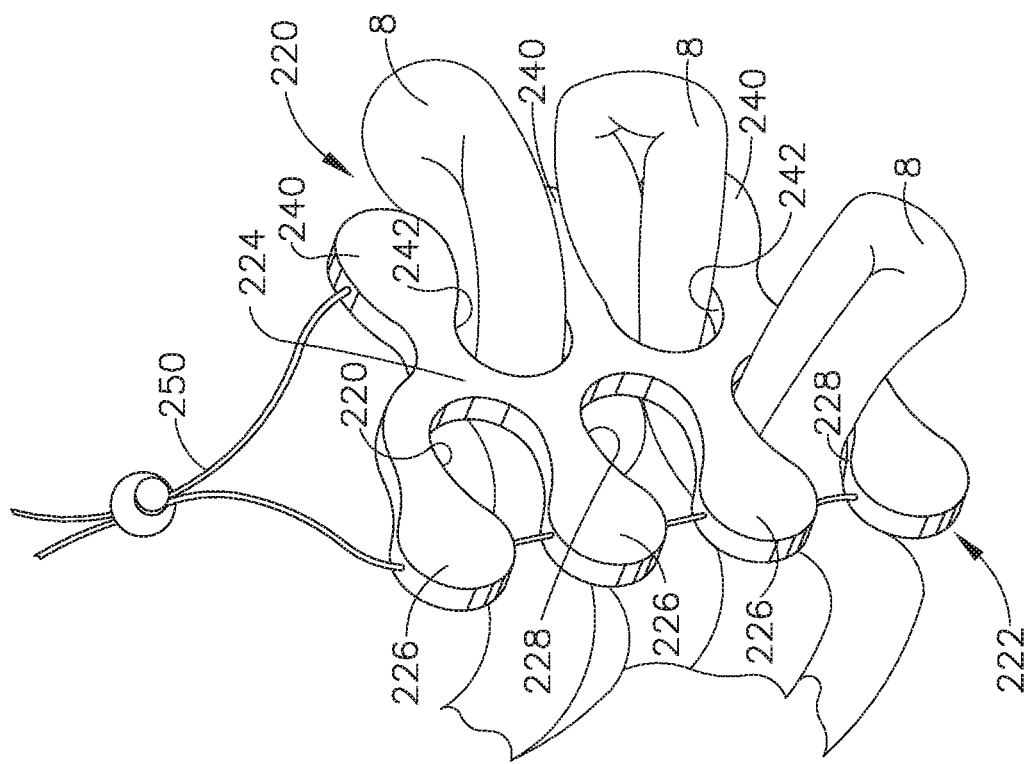
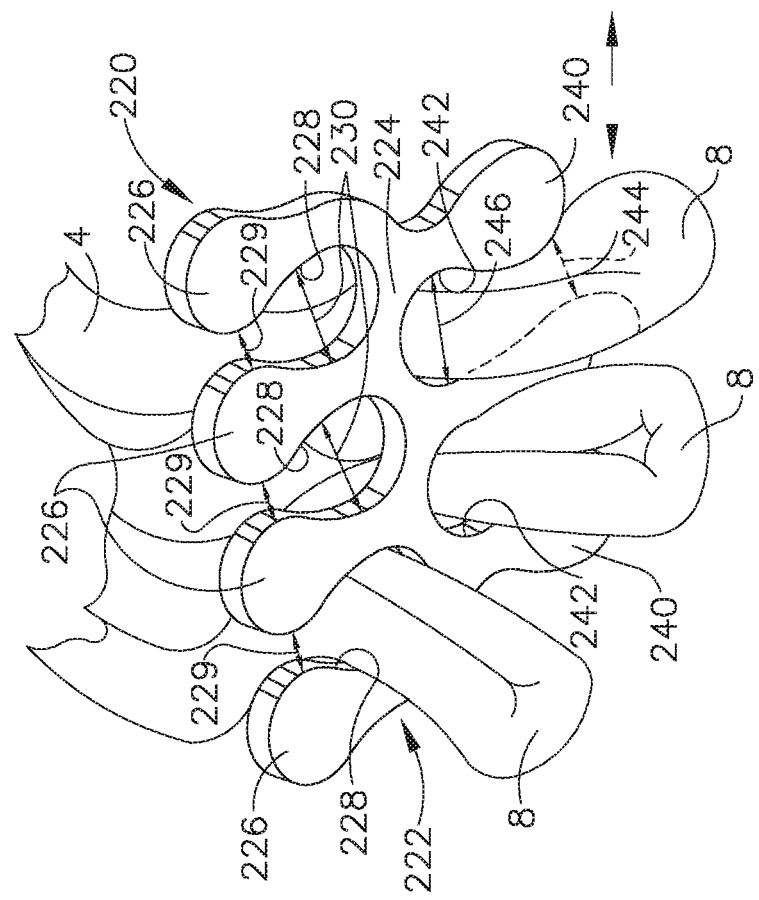
FIG. 42
FIG. 41

SURGICAL BOWEL RETRACTOR DEVICES

CROSS-REFERENCE TO RELATED APPLICATIONS

This application is a continuation application claiming priority under 35 U.S.C. § 120 to U.S. patent application Ser. No. 14/788,923, entitled SURGICAL BOWEL RETRACTOR DEVICES, filed on Jul. 1, 2015, which issued on Nov. 20, 2018 as U.S. Pat. No. 10,130,352, which is a continuation application claiming priority under 35 U.S.C. § 120 to U.S. patent application Ser. No. 13/181,827, entitled SURGICAL BOWEL RETRACTOR DEVICES, filed Jul. 13, 2011, which issued on Jul. 28, 2015 as U.S. Pat. No. 9,089,330, the entire disclosures of which are hereby incorporated by reference herein.

FIELD OF THE INVENTION

The present invention generally relates to surgical devices for temporarily retaining and supporting tissues and organs in a desired orientation during surgery, and more particularly, to devices for retracting portions of the bowel during surgery.

BACKGROUND

One major challenge to employing laparoscopic colorectal techniques is the ability to move all of the unrelated or non-involved tissue out of the surgical site to permit better physical and visual access to the target tissue or organ. In an open procedure, large metal retractors would be used to pull the masses of small intestines away and then pack them off with surgical sponges. When performing various colorectal surgical procedures, the surgeon often must manipulate the surgical instruments through a pile or collection of bowel to open up a window to operate in.

Thus, the need exists for devices that can be used to support portions of the bowel during laparoscopic colorectal operations in unobtrusive orientations to provide better physical and visual access to the portion of the bowel to be operated on.

The foregoing discussion is intended only to illustrate some of the shortcomings present in the field of the invention at the time, and should not be taken as a disavowal of claim scope.

BRIEF SUMMARY

In connection with general aspects of various embodiments of the present invention, there is provided a bowel retractor device that, in various forms, comprises an elastic body that is configurable from a first collapsed position wherein the elastic body is insertable through an opening in a patient's body to a second expanded position wherein a portion of the patient's bowel may be supported by a central portion of the elastic body in a desired orientation.

In connection with yet another general aspect of one form of the present invention, there is provided a bowel retractor device that includes a central portion that has a first plurality of flexible first arms protruding therefrom in a first direction. The plurality of first flexible arms defines a first opening between each adjacent flexible arm. A second plurality of flexible second arms protrude from the central portion in a second direction wherein each flexible second arm protrudes from the central portion at positions opposite from the first openings and wherein the flexible second arms are spaced from each other to form a second opening therebetween.

In accordance with still another general aspect of one form of the present invention, there is provided a bowel retractor device that includes a selectively inflatable ring that has a textured annular surface that defines an interior area. A supply conduit is coupled to the selectively inflatable ring and a source of pressurized medium.

In accordance with other general aspects of various forms of the present invention, there is provided a method for performing laparoscopic bowel surgery on a target portion of a patient's bowel. In one form of the present invention, the method includes inserting at least one bowel retractor device through an opening in the patient. Each of the bowel retractor devices comprises a body that is configurable from a first collapsed position wherein the body is insertable through the opening to a second expanded position. The method further includes engaging a corresponding non-target portion of the bowel with a central portion of each of the at least one bowel retractor devices when in the second expanded position and positioning the at least one bowel retractor device to locate the corresponding non-target bowel portion engaged thereby in non-obtrusive positions to thereby provide physical and visual access to the target portion of the bowel.

In various embodiments, a bowel retractor device comprising an elongated flexible endless collar member, a plurality of discrete second flexible fingers, and a plurality of discrete second flexible fingers is disclosed. The elongated flexible endless collar member comprises an inner wall that defines a central open area. The plurality of discrete first flexible fingers protrude inwardly from a first portion of the inner wall into the central open area. Each discrete first flexible finger comprises a first end. The first ends are spaced from each other to define a first space therebetween. Each first end comprises a first ball-shaped member formed thereon. The plurality of discrete second flexible fingers protrude from a second portion of the inner wall that faces the first portion of the inner wall. Each discrete second flexible finger comprises a second end. The second ends define a second space therebetween. Each second end extends into a corresponding first space. Each first end extends into a corresponding second space. Each second end comprises a second ball-shaped member formed thereon.

In various embodiments, a bowel retractor device comprising an elongated flexible endless collar member, a plurality of discrete first flexible fingers, and a plurality of discrete second flexible fingers is disclosed. The elongated flexible endless collar member comprises an inner wall that defines an elongated central open area. The elongated central open area comprises a first open area end portion and a second open area end portion. The first open area end portion comprises a first width and the second open area end portion comprises a second width that differs from the first width. The plurality of discrete first flexible fingers protrude inwardly from a first portion of the inner wall into the elongated central open area. Each discrete first flexible finger comprises a first end. The first ends are spaced from each other to define a first space therebetween. The plurality of discrete second flexible fingers protrude from a second portion of the inner wall that faces the first portion of the inner wall. Each discrete second flexible finger comprises a second end. The second ends define a second space therebetween. Each second end extends into a corresponding first space. Each first end extends into a corresponding second space.

In various embodiments, a bowel retractor device comprising a flexible endless collar member, a plurality of discrete first flexible fingers, and a plurality of discrete second flexible fingers is disclosed. The flexible endless collar member comprises an inner wall that defines a central open area. The plurality of discrete first flexible fingers protrude from a first portion of the inner wall. The discrete first flexible fingers are spaced from each other to define a first space therebetween. The plurality of discrete second flexible fingers protrude from a second portion of the inner wall that faces the first portion of the inner wall. Each discrete second flexible finger comprises a second end that extends into a corresponding first space. At least one of the discrete first flexible fingers and at least one of the discrete second flexible fingers each comprise a ball-shaped feature formed on an end thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 2 is a perspective view showing a conventional trocar installed through the abdominal wall of a patient and being used to pass a bowel retractor embodiment of the present invention into a surgical area within the abdomen;

FIG. 3 is a view of a bowel retractor embodiment of the present invention inserted in a twisted orientation into a cannula of a trocar;

FIG. 4 is a top view of a bowel retractor device embodiment of the present invention;

FIG. 5 is a top view of another bowel retractor device embodiment of one form of the present invention;

FIG. 6 is a perspective view of another bowel retractor device embodiment with non-target portions of a patient's bowel supported therein;

FIG. 7 is another perspective view of a bowel retractor device located inside a patient's abdomen and wherein the surgeon is using a grasping device to pull non-target portions of the patient's bowel through an opening in the bowel retractor device;

FIG. 8 is a top view of another bowel retractor device embodiment of the present invention;

FIG. 9 is a perspective view of the bowel retractor device of FIG. 8 supporting non-target portions of a patient's bowel therein;

FIG. 14 is a perspective view of another bowel retractor device embodiment of the present invention;

FIG. 15 is a perspective view of the bowel retractor device of FIG. 14 supporting non-target portions of a patient's bowel therein and wherein retractor manipulation needles have been inserted through the abdominal wall to engage portions of the bowel retractor device;

FIG. 20 is a side view of another bowel retractor device embodiment of the present invention;

FIG. 21 is a perspective view of the bowel retractor device embodiment of FIG. 20 with portions of a patient's bowel supported therein;

FIG. 24 is a perspective view of another bowel retractor device embodiment of the present invention;

FIG. 25 is a perspective view of another bowel retractor device embodiment of the present invention;

FIG. 26 is a perspective view of another bowel retractor device embodiment of the present invention;

FIG. 31 is a perspective view of a portion of a patient's colon with four other bowel retractor device embodiments of the present invention supporting non-target bowel portions;

FIG. 32 is a perspective view of another bowel retractor device embodiment of the present invention in an open position and supported by a grasping instrument;

FIG. 33 is another perspective view of the bowel retractor device embodiment of FIG. 32 and supporting a bowel portion therein;

FIG. 34 is a partial perspective view of a trocar device inserted through a portion of a patient's abdominal wall with the bowel retractor device of FIGS. 32 and 33 being inserted through the trocar cannula;

FIG. 35 is a top view of the bowel retractor device embodiment of FIGS. 32-34 in a collapsed or rolled-up position wherein the retractor device may be inserted through a trocar cannula or other opening in a patient's body;

FIG. 41 is a partial perspective view of another bowel retractor device embodiment of the present invention supporting a portion of a patient's bowel therein;

FIG. 42 is a partial perspective view of another bowel retractor device embodiment of the present invention supporting a portion of a patient's bowel therein;

DETAILED DESCRIPTION

Figure 1:
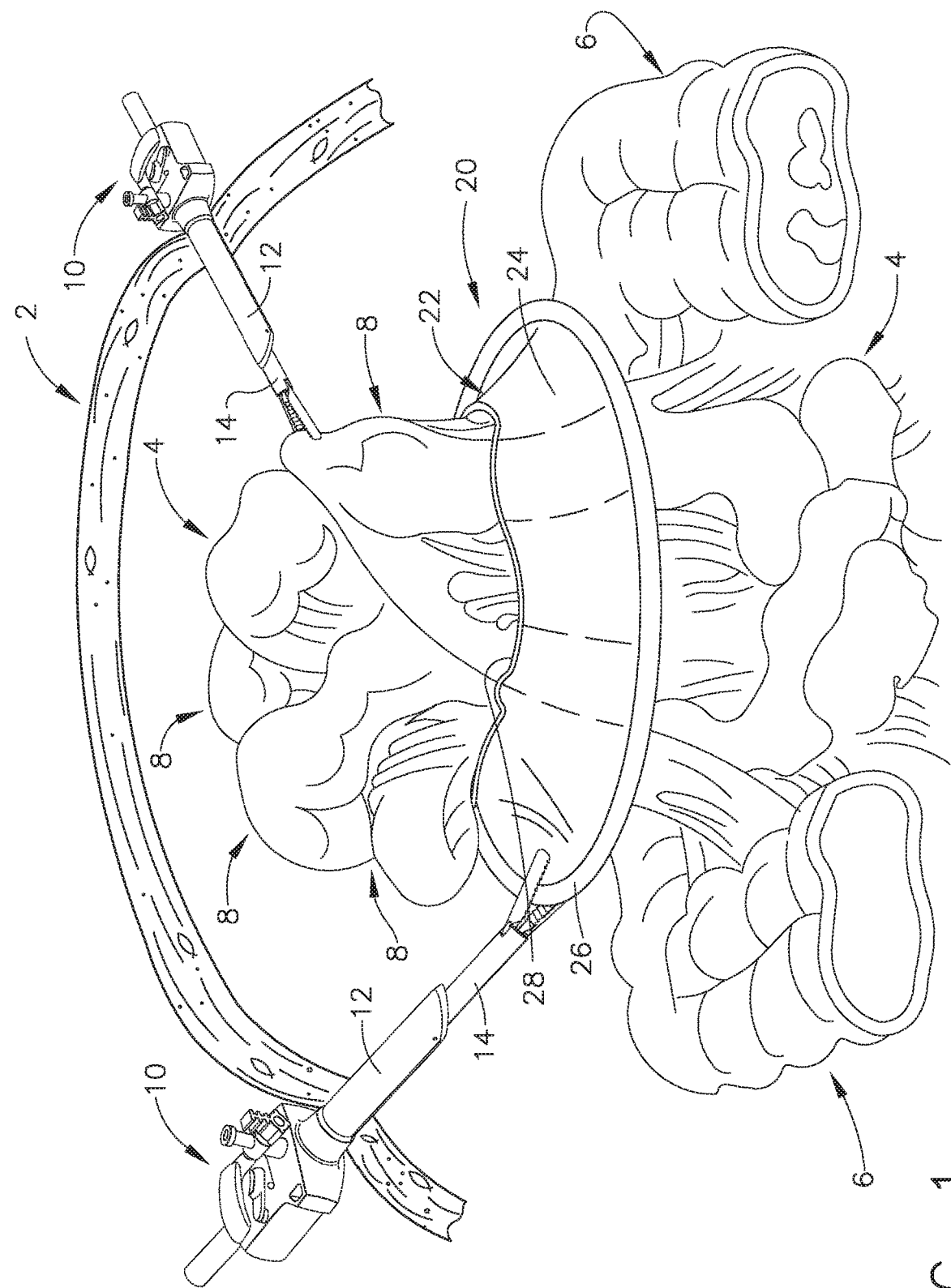
FIG. 1 is a view of a portion of a patient's abdomen and bowel segment with two trocars installed through the abdominal wall and one of the bowel retraction device embodiments of the present invention with non-target portions of the patient's bowel installed therein.

The assignee of the present application also owns the following applications which were contemporaneously filed herewith on Jul. 13, 2011 and which are each herein incorporated by reference in their respective entireties:

U.S. patent application Ser. No. 13/181,779, entitled MULTIPLE PART ANVIL ASSEMBLIES FOR CIRCULAR SURGICAL STAPLING DEVICES, now U.S. Pat. No. 9,125,654;

U.S. patent application Ser. No. 13/181,798, entitled MODULAR SURGICAL TOOL SYSTEMS, now U.S. Pat. No. 9,113,884;

U.S. patent application Ser. No. 13/181,801, entitled SPECIMEN RETRACTION DEVICES AND METHODS, now U.S. Pat. No. 8,632,462;

U.S. patent application Ser. No. 13/181,807, entitled MODULAR OCCLUSION AND TISSUE ACQUISITION MECHANISMS FOR CIRCULAR STAPLING DEVICES, now U.S. Pat. No. 8,827,903;

U.S. patent application Ser. No. 13/181,831, entitled TISSUE MANIPULATION DEVICES, now U.S. Pat. No. 8,858,590;

U.S. patent application Ser. No. 13/181,768, entitled COLLAPSIBLE ANVIL PLATE ASSEMBLIES FOR CIRCULAR SURGICAL STAPLING DEVICES, now U.S. Pat. No. 9,113,883;

U.S. patent application Ser. No. 13/181,786, entitled CIRCULAR STAPLING DEVICES WITH TISSUE-PUNCTURING ANVIL FEATURES, now U.S. Pat. No. 9,033,204;

U.S. patent application Ser. No. 13/181,774, entitled ANVIL ASSEMBLIES WITH COLLAPSIBLE FRAMES FOR CIRCULAR STAPLERS, now U.S. Pat. No. 8,978,955;

U.S. patent application Ser. No. 13/181,842, entitled RECTAL MANIPULATION DEVICES, now U.S. Pat. No. 8,734,478; and U.S. patent application Ser. No. 13/181,836, entitled SURGICAL ACCESS DEVICES WITH ANVIL INTRODUCTION AND SPECIMEN RETRIEVAL STRUCTURES, now U.S. Pat. No. 9,211,122.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

FIG. 1 illustrates a portion of a patient's abdominal wall 2 and portions of the patient's bowel or colon 4. More specifically, a bowel retractor device 20 embodiment of the present invention is employed to support/retract non-target bowel portions 8 from target bowel portions 6. As used herein, the term "target bowel portion(s)" refers to that portion or portions of the bowel on which the surgical procedure is to be performed. The term "non-target bowel portions" refers to those portions of the bowel that are not the subject of the surgical procedure and which often obscure physical and/or visual access to the target portions. In the depicted Figure, two conventional trocar devices 10 have been inserted through the abdominal wall 2. Such trocar devices 10 include a cannula 12 that is configured to form of a passage through the abdominal wall 2 through which surgical instruments 14 may be inserted. A variety of styles and sizes of trocars are known. In general, the trocars are sized based on the inner diameter of their respective cannula.

In various non-limiting embodiments, the bowel retractor device 20 comprises an elastic body portion 22 that is configurable from a first collapsed orientation that permits the elastic body portion 22 to be inserted through a trocar cannula 12 to a second expanded position wherein a non-target portion or portions 8 of a patient's bowel 4 are supported by a central portion 24 of the bowel retractor device 20. In various embodiments, the central portion 24 may comprise a substantially flexible film such as for example silicone or neoprene film having a thickness ranging from, for example, 0.020 inches to 0.120 inches that has a collar or flexible outer ring 26 formed therearound. The flexible outer ring 26 may comprise for example in at least one embodiment, an embedded stainless steel wire or titanium wire. In at least one embodiment, when the retractor device 20 is in the first or collapsed position, it is in a twisted configuration such as those shown in FIGS. 2 and 3. When the retractor device 20 is in the second or expanded position, the retractor device 20 may assume the positions shown in FIGS. 1, 4, and 5. The flexible central portion 24 has a first amount of elasticity and the flexible outer ring 26 has a second amount of elasticity. In some embodiments, the second amount of elasticity is less than the first amount of elasticity. That is the outer ring 26 may be more rigid that the flexible central portion 24.

As can be seen in FIGS. 4 and 5, the central portion 24 of the bowel retractor device 20 has at least one opening 28 therein. The size, shape, number, and orientation(s) of such opening(s) may vary. For example, in FIG. 4, the opening 28 comprises an elongated slot and the opening 28 in FIG. 5 has a multiple-pointed star shape.

The retractor devices 20 may be used as follows in connection with one exemplary method of the present invention. To commence the surgical process, at least two trocars 10 are installed through the patient's abdominal wall 2 in a known manner. One of the trocars 10 may be initially used to pass the retractor device or devices 20 therethrough. The other trocar 10 may be used to enable the surgeon to pass a conventional surgical instrument such as a grasper 14 to grab the retractor device 20 and position it over the non-target bowel portions 8. Once the retractor device 20 has exited the trocar cannula 12, the surgeon may also use that trocar 10 to pass a second grasper 14 therethrough to assist in drawing the non-target portions 8 of bowel through the opening(s) 28 in the retractor device 20. Such arrangement enables the non-target bowel portions 8 to be retained away from the target bowel portions 6. By introducing three or four of the retractor devices 20, for example, multiple quadrants of non-target bowel portions 8 could be tucked away and easily movable to clear the surgical site. The coupled group could be pulled en masse to one side or the other of the target bowel portion(s) 6 making it very easy to negotiate the multiple bowel quadrants to perform the surgical procedure on the target bowel portions 6. In various embodiments, the surgeon may pull one section 8 of bowel 4 multiple times through the opening 26 to bunch up and constrain that non-target portion 8 of the bowel 4.

In some embodiments, the outer ring or collar 26 may be bendable as opposed to being purely elastic. For example, in some embodiments, the collar 26 may comprise a bendable metal wire or cable that is encapsulated in a flexible material such as silicone, neoprene, etc. In such arrangement, the surgeon may bend or twist the collar or outer ring 26 into a desired configuration and the metal wire will retain it in that configuration. Once the retractor device 20 has been fully inserted into the patient, the surgeon may bend the retractor device 20 into whatever restraining form that would be most useful to keep the clump of non-target bowel 8 out of the working space. For example, the retractor device 20 may be folded or bent and then lodged up behind the trocar cannula 12 or held back with a grasping instrument 14, whichever is more convenient. The flexible fit holds the non-target bowel portion 8 together without strangulating it or interfering with the peristalsis which might cause swelling. The fit between the non-target portion(s) 8 pulled through the opening(s) is such that the non-target bowel portion(s) would not slip back out of the opening 28.

FIGS. 6 and 7 illustrate bowel retractor devices 20 with alternative opening arrangements. In particular, the openings 28 comprises a plurality of slots and perforations 29. The perforations 29 are aligned off of each end of the slots 28 as shown and enable the flexible center portion 24 to rupture to enable the slots 28 to enlarge or expand as needed as the bowel portions 8 are pulled therethrough. In FIGS. 7 and 8, those slots that have expanded are designated as slots "28E".

FIG. 8 illustrates another retractor device 30 embodiment of the present invention that includes a body portion 32 that is configurable from a first collapsed orientation that permits the body portion 32 to be inserted through a trocar cannula or other opening in a patient's body to a second expanded position wherein a non-target portion or portions 8 of a patient's bowel 4 are supported by a central portion 34 of the bowel retractor device 30. In various embodiments, the central portion 34 may comprise a substantially flexible film such as, for example, a silicone or neoprene film having a thickness ranging from, for example, 0.020 inches to 0.120 inches that has a collar or flexible outer ring 36 formed therearound. As can be seen in FIG. 8, the outer collar 36 is formed with a plurality of spaced radially outwardly extending tabs 38. Each tab 38 has a hole 40 therethrough that is configured to receive a cinchable member 42 such as, for example, a vectran, nylon, polyglycolic acid (PGA), catgut, or polypropylene cable to be woven therethrough as shown. The end portions 43, 44 of the cinchable member 42 pass through a grommet portion 39 of the collar 36. By applying tension "T" to the end portions 43, 44 will cause the bowel retractor 30 to be cinched around the non-target bowel portions 8 pulled through an opening 35 in the central portion 34. The cinchable member 42 may also be used to manipulate the retractor 30 and retain it in a desired position.

In FIG. 9, the bowel retractor device 50 is substantially similar to the bowel retractor device 30, except that the bowel retractor device 50 lacks the cinchable member. Instead a flexible tether 52 extends from the device 50. The tether has a manipulation ring 54 attached thereto as shown. The outwardly extending tabs 38 form portions of the device 50 that may be easily grasped with a grasping instrument to facilitate the installation, manipulation and positioning of the bowel retractor device 50.

Figure 10:
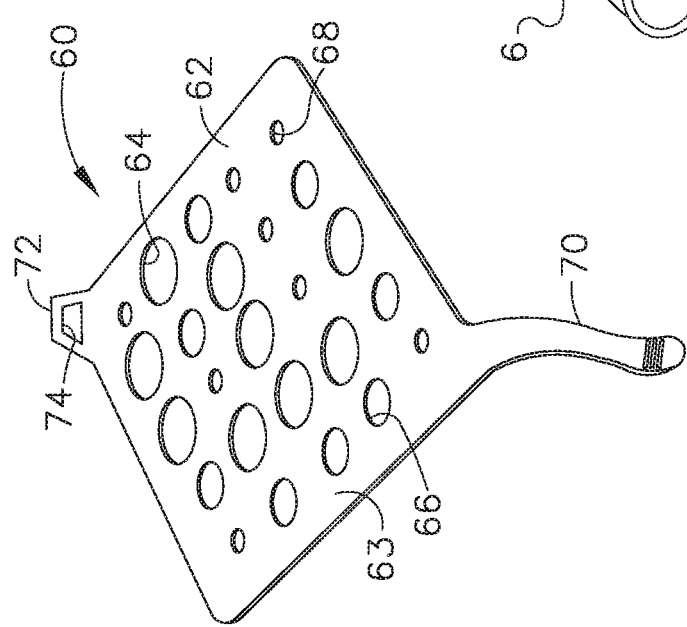
FIG. 10 is a front perspective view of another bowel retractor device embodiment of the present invention.
Figure 11:
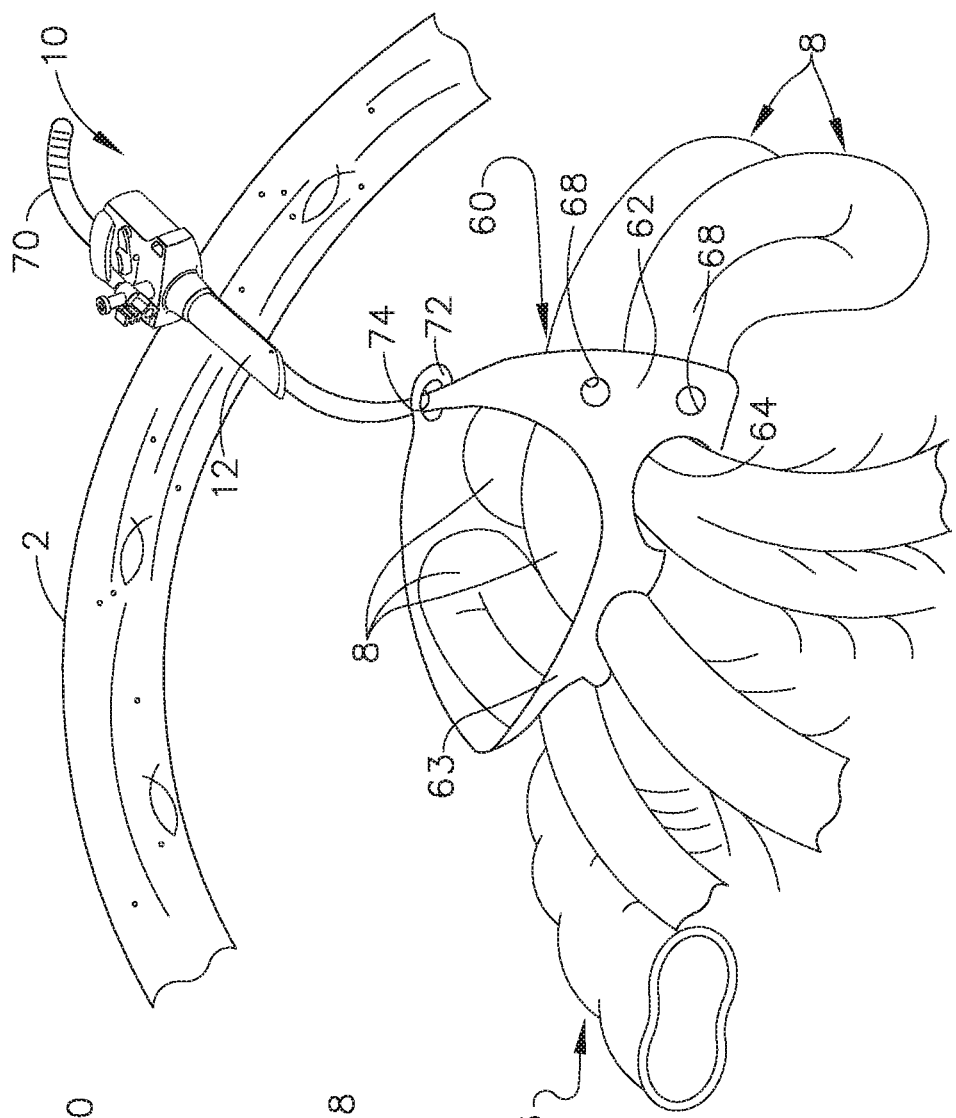
FIG. 11 is a perspective view of the bowel retractor device of FIG. 10 supporting non-target portions of a patient's bowel therein and wherein the tether portion thereof has be inserted through the cannula of a trocar.

FIGS. 10 and 11 illustrate another bowel retractor device embodiment 60 of the present invention. The bowel retractor 60 includes an elastic body portion 62 that comprises a flexible plate member 63 that has a plurality of openings 64, 66, 68 therethrough. In various embodiments, the flexible plate member 63 may comprise, for example, a silicone or neoprene film having thicknesses that range from 0.020 inches to 0.150 inches. In the illustrated embodiment, three different sizes of openings are shown. In other embodiments, all of the openings may have the same size and/or have different shapes. The scope of this embodiment of the present invention is intended to cover embodiments with a variety of differently-shaped openings and different arrangements of openings—having the same size and having different sizes. As can be further seen in FIGS. 10 and 11, a tether 70 is attached to other otherwise formed with the body portion 62 such that it protrudes therefrom. In addition, a retention tab or portion 72 is also formed on or attached to the body portion 62. In the illustrated embodiment, the body portion 62 is substantially square-shaped and the tether 70 and retention tab 72 are formed on opposite corners of the plate member 63.

The bowel retractor device 60 may be used as follows. After the device 60 has been inserted through the trocar 10 or otherwise located at the surgical site, the surgeon may use graspers or other surgical instruments to draw the non-target portions 8 of the patient's bowel 4 through one or more of the openings 64, 66, 68 in the body portion 62 in the manner described above. Once the non-target bowel portion(s) 8 have been drawn through one or more of the openings 64, 66, 68 the surgeon may loop the tether 70 through an opening 74 in the retention tab 72 and extend the tether 70 back through the trocar cannula 12 to enable the surgeon to retain, manipulate and/or position the retractor device 60 and retained non-target bowel portion(s) 8 from outside of the patient.

Figure 13:
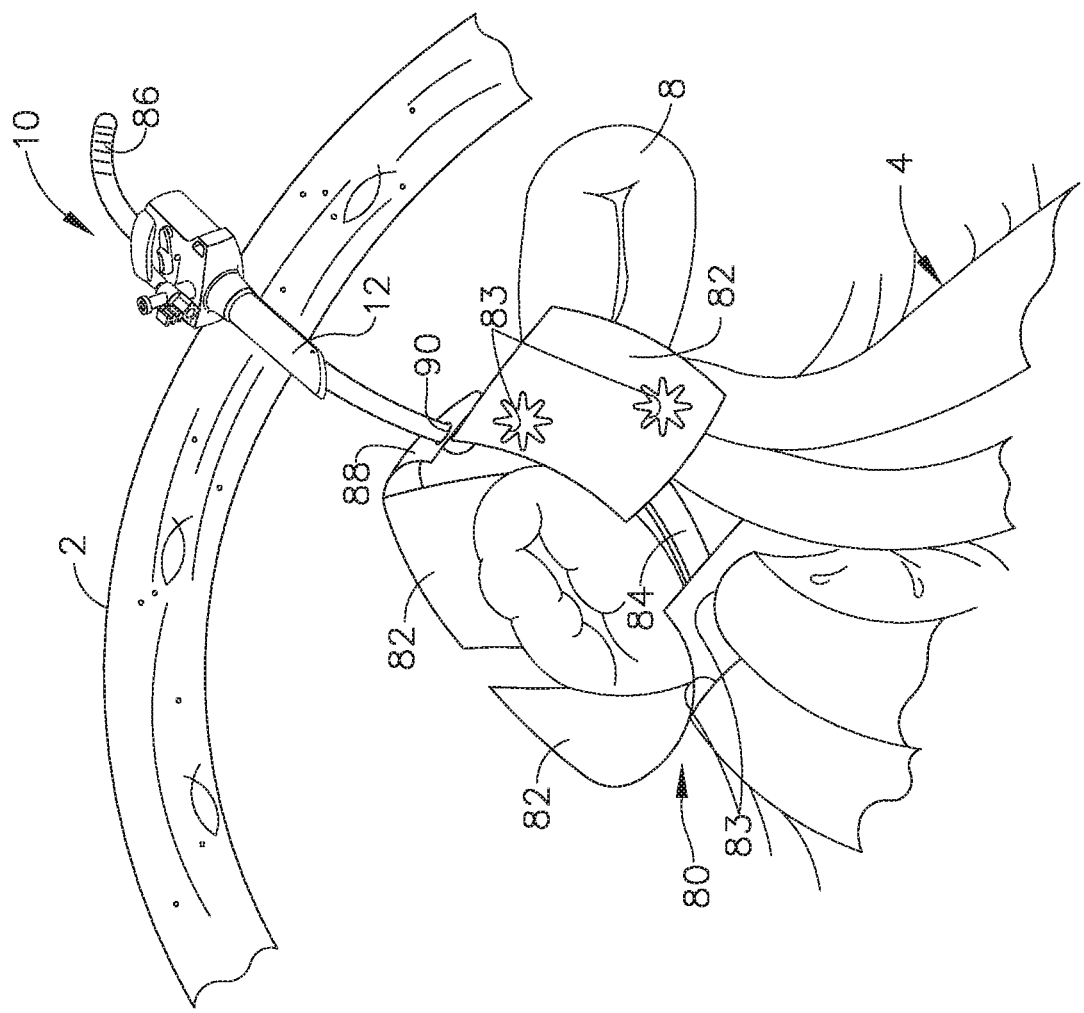
FIG. 13 is a perspective view of the bowel retractor device of FIG. 12 supporting non-target portions of a patient's bowel therein and wherein the tether portion thereof has be inserted through the cannula of a trocar.
Figure 12:
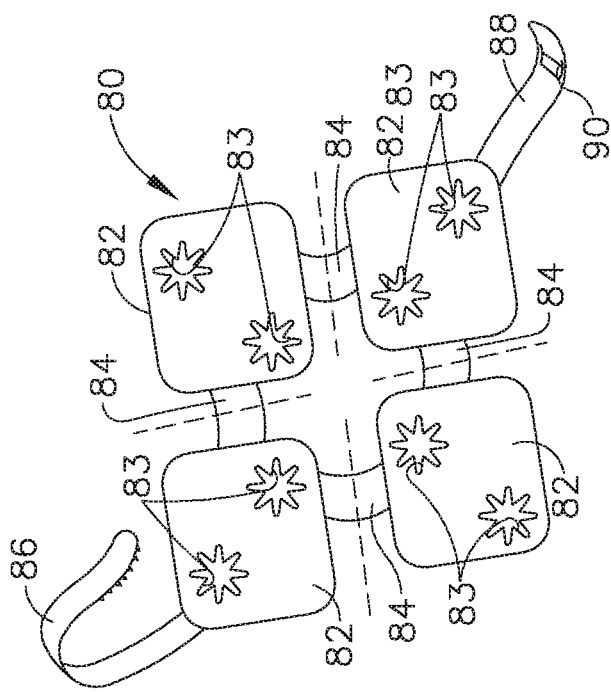
FIG. 12 is a top view of another bowel retractor device embodiment of the present invention.

FIGS. 12 and 13 illustrate another bowel retractor device embodiment 80 of the present invention. As can be seen in FIG. 12, in at least one embodiment, the device 80 comprises a plurality of (four are shown) of flexible plate members 82 that are interconnected by flexible straps 84. Each plate member 82 has at least one (two are shown) openings 83 therein. The openings 83 shown have a multiple pointed star shape. The number, shape and orientation of openings 83 may vary. One or more plate members 82 may have different numbers of differently shaped openings in arrangements that differ from the openings and arrangements in one or more other plate members 82. In still other embodiments, at least one plate member 82 has at least one opening 83 therethrough. As can also be seen in FIG. 12, a tether 86 is attached to, or is other otherwise formed with, one of the plate members 82 such that it protrudes therefrom In addition, a retention strap 88 is attached to, or is otherwise formed with, another plate member 82. In the illustrated embodiment, the four plate members 82 are shown and the tether 86 and retention strap 72 are formed on the corners of opposite plate members 82.

The bowel retractor device 80 may be used as follows. After the device 80 has been inserted through the trocar 10 or otherwise located at the surgical site, the surgeon may use graspers or other surgical instruments to draw the non-target portions 8 of the patient's bowel 4 through one or more of the openings 83 in the plate members 82 in the manner described above. Once the non-target bowel portion(s) 8 have been drawn through one or more of the openings 83, the surgeon may loop the tether 86 through an opening 90 in the retention strap 88 and extend the tether 86 back through the trocar 10 to enable the surgeon to retain, manipulate and/or position the device and retained non-target bowel portion(s) 8 from outside of the patient.

FIGS. 14 and 15 illustrate another bowel retractor embodiment 100 of the present invention. The bowel retractor 100 includes a body portion 102 that comprises a flexible mesh portion that has a plurality of openings 104 therethrough. In various embodiments, the body portion may be fabricated from, for example, silicone, neoprene, etc. In the illustrated embodiment, openings 104 may be are arranged in a grid-like fashion. In other embodiments, the openings may have different sizes. The scope of this embodiment of the present invention is intended to cover embodiments with a variety of differently-shaped openings and different arrangements of openings—having the same size and having different sizes. As can be further seen in FIGS. 14 and 15, at least one manipulation formation 106 is formed on the body portion 102. In the illustrated embodiment, the device 100 is substantially square-shaped and a manipulation formation 106 is formed on each corner thereof. Each manipulation formation 106 has a hole 108 therethrough to enable a manipulation tool to engage and manipulate the device 100. The manipulation tool may comprise a grasper or other surgical instrument. In the illustrated embodiment, two needle-like hook members 110 are inserted through the patient's abdominal wall and serve to hook the openings 108 in the manipulation formations 106.

The bowel retractor device 100 may be used as follows. After the device 100 has been inserted through the trocar 10 or otherwise located at the surgical site, the surgeon may use graspers or other surgical instruments to draw the non-target portions 8 of the patient's bowel 4 through one or more of the openings 104 in the body portion 102 in the manner described above. Once the bowel portions 8 have been drawn through one or more of the openings 104, the surgeon may insert one or more of the needle-like hook members 110 through the abdominal wall 2 to hookingly engage one or more of the manipulation formations 106 to position and or retain the device 100 in a desired orientation.

Figure 16:
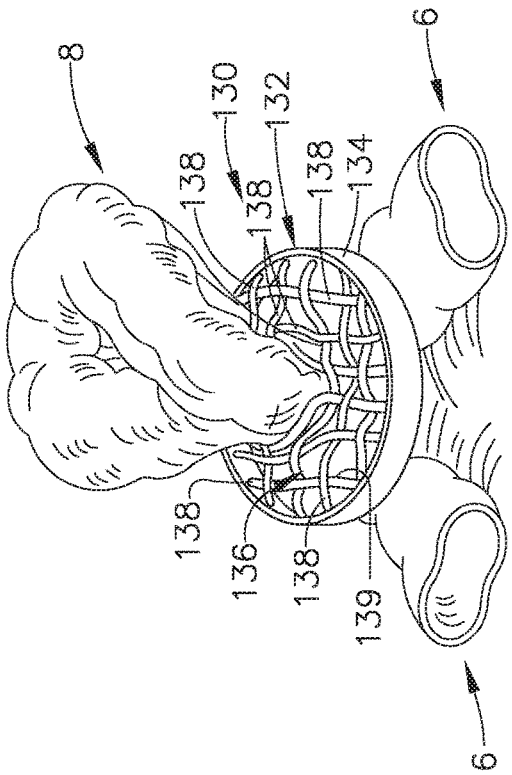
FIG. 16 is a perspective view of another bowel retractor device embodiment of the present invention.

FIG. 16 illustrates another bowel retractor device embodiment 120 of the present invention. The bowel retractor device 120 includes a body portion 122 that comprises a flexible annular ring 124 that has a flexible central portion 126 attached thereto. In at least one embodiment, the flexible central portion 126 comprises a plurality of interwoven flexible ribbon-like members 128. In various embodiments, the flexible annular ring may be fabricated from, for example, Polypropylene, Santoprene, etc. The interwoven ribbon members 128 will have weave tightness that permits non-target portion(s) 8 of the patient's bowel to be pulled therethrough without damaging the bowel, yet retain the non-target bowel portion(s) in position. To assist the surgeon with the manipulation and support of the device 120, a manipulation formation 129 may be formed on the annular ring 124 as shown.

The bowel retractor device 120 may be used as follows. After the device 120 has been inserted through the trocar 10 or otherwise located at the surgical site, the surgeon may use graspers or other surgical instruments to draw the non-target portions 8 of the patient's bowel 4 between the ribbons 128 in the manner described above. Once the bowel portions 8 have been drawn between the ribbons 128, the surgeon may use a grasper or other surgical instrument to engage the manipulation formation 129 to position and or retain the device 120 in a desired orientation.

Figure 17:
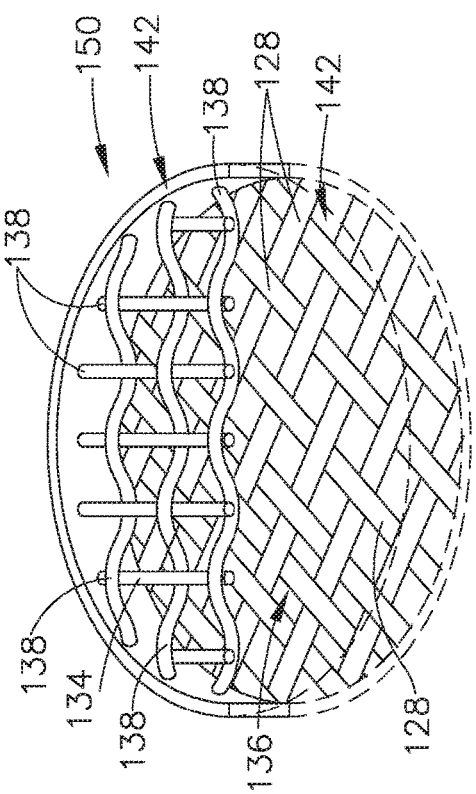
FIG. 17 is another perspective view of the bowel retractor device embodiment of FIG. 16 with a non-target portion of a patient's bowel being supported thereby.

FIG. 17 illustrates another bowel retractor device embodiment 130 of the present invention. The bowel retractor device 130 includes a body portion 132 that comprises a flexible annular ring 134 that has a flexible central portion 136 attached thereto. In at least one embodiment, the flexible central portion 136 comprises a plurality of interwoven flexible strips 138. In various embodiments, the flexible annular ring 134 may be fabricated from, for example, Santoprene, polypropylene, etc. In at least one embodiment, the interwoven flexible strips 138 have a substantially circular cross-sectional shape. The interwoven strips 138 define a plurality of openings 139 and will have weave tightness that permits non-target portion(s) 8 of the patient's bowel 4 to be pulled through one or more of the openings 139 without damaging the bowel, yet retain the bowel in position. To assist the surgeon with the manipulation and support of the device 120, a manipulation formation (not shown) may be formed on the annular ring 134 as shown.

The bowel retractor device 130 may be used as follows. After the device 130 has been inserted through the trocar 10 or otherwise located at the surgical site, the surgeon may use graspers or other surgical instruments to draw the non-target portions 8 of the patient's bowel 4 through one or more of the openings 139 in the manner described above. Once the non-target bowel portion(s) 8 have been drawn between the flexible strips 138, the surgeon may use a grasper or other surgical instrument to engage the manipulation formation to position and or retain the device 130 in a desired orientation.

Figure 18:
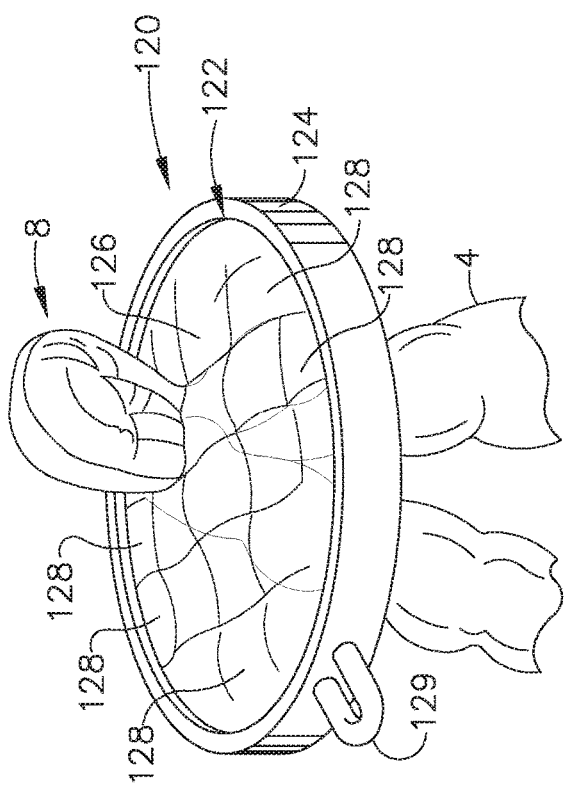
FIG. 18 is a cross-sectional view of the bowel retractor device embodiment of FIG. 16.
Figure 19:
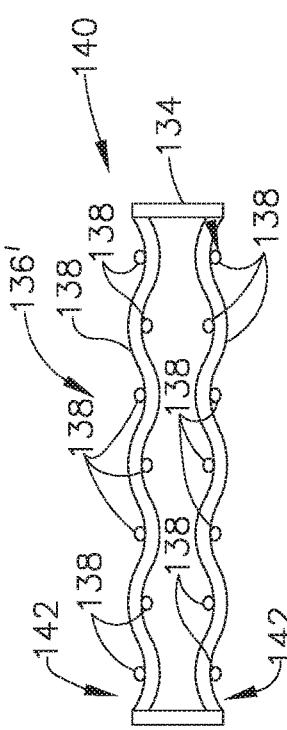
FIG. 19 is a partial perspective view of another bowel retractor device embodiment of the present invention.

FIG. 18 illustrates another bowel retractor device embodiment 140 of the present invention which is substantially similar to the bowel retractor device 130 described above except that the central portion 136' comprises a plurality of layers 142 of interwoven flexible strips 138. The bowel portions 8 may be drawn through the openings 139 in one or more of the layers 142. FIG. 19 illustrates another bowel retractor device embodiment 150 of the present invention which is substantially similar to the bowel retractor device 140 described above, except that one of the layers 142 comprises a plurality of interwoven ribbons 128 and another layer 142 comprises a plurality of interwoven flexible strips 138.

FIG. 20 illustrates another bowel retractor device embodiment 150 of the present invention. The bowel retractor device 150 includes a body portion 152 that comprises a flexible endless collar member 154 that defines an inner area 156. In various embodiments, the flexible endless collar member 154 is elongated and is sized to be passed down through a trocar cannula 12 or other opening through the abdominal wall 2. The flexible endless collar member 154 may be fabricated from, for example, Santoprene, polypropylene, etc. The device 150 further includes a plurality of flexible fingers 156, 160 that protrude inwardly from the endless collar member 154. In at least one embodiment, the flexible fingers 158 extend between fingers 160 and have a cross-sectional size that differs from a cross-sectional size of fingers 160. Also in various embodiments, each of the fingers 158 have a ball-shaped member 159 formed on the end thereof and each of the fingers 160 have a ball-shaped member 162 formed on the end thereof. In at least one embodiment, each of the ball-shaped members 159 have a diameter that differs from the diameter of the ball-shaped members 162.

The bowel retractor device 150 may be used as follows. After the device 150 has been inserted through the trocar 10 or otherwise located at the surgical site, the surgeon may use graspers or other surgical instruments to draw the non-target portions 8 of the patient's bowel 4 through the central area 156. Once the non-target bowel portions 8 have been drawn between the flexible fingers 158, 160, the surgeon may use a grasper or other surgical instrument to engage the manipulation formation 166 formed on the endless collar member 154 to position and or retain the device 150 in a desired orientation.

Figure 22:
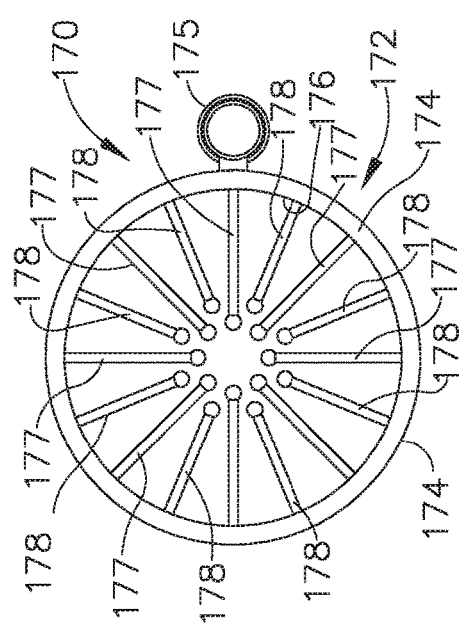
FIG. 22 is a top view of another bowel retractor device embodiment of the present invention.
Figure 23:
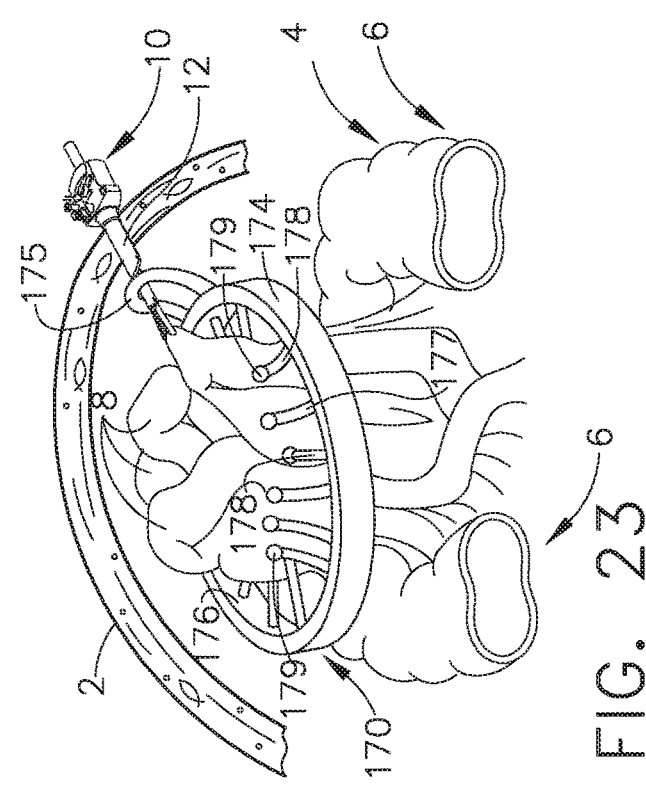
FIG. 23 is a perspective view of the bowel retractor device embodiment of FIG. 22 inside a portion of a patient's abdomen and supporting a non-target bowel portion therein.

FIG. 22 illustrates another bowel retractor device embodiment 170 of the present invention. The bowel retractor device 170 includes a body portion 172 that comprises a flexible endless collar member 174 that defines an inner area 176. In various embodiments, the flexible endless collar member 174 is elongated and is sized to be passed down through a trocar cannula 12 or other opening through the abdominal wall 2. The flexible end less collar member 174 may be fabricated from, for example, Santoprene, polypropylene, etc. The device 170 further includes a plurality of flexible fingers 177, 178 that protrude inwardly from the endless collar member 174. In at least one embodiment, the flexible fingers 178 extend between fingers 177. The flexible fingers 178 have a length that is shorter than the length of fingers 177. Also in various embodiments, each of the fingers 177, 178 have a ball-shaped member 179 formed on the end thereof. In at least one embodiment, the fingers 177, 178 lie along a common plane. Also in one embodiment, a manipulation formation 175 is formed on the endless collar member 174 to enable the device 170 to be easily manipulated with a surgical instrument such as a grasping instrument.

The bowel retractor device 170 may be used as follows. After the device 170 has been inserted through the trocar 10 or otherwise located at the surgical site, the surgeon may use graspers or other surgical instruments to draw the non-target portions 8 of the patient's bowel 4 through the central area 176. Once the non-target bowel portions 8 have been drawn between the flexible fingers 177, 178, the surgeon may use a grasper or other surgical instrument to engage the manipulation formation 175 formed on the endless collar member 174 to position and or retain the device 170 in a desired orientation.

Figure 27:
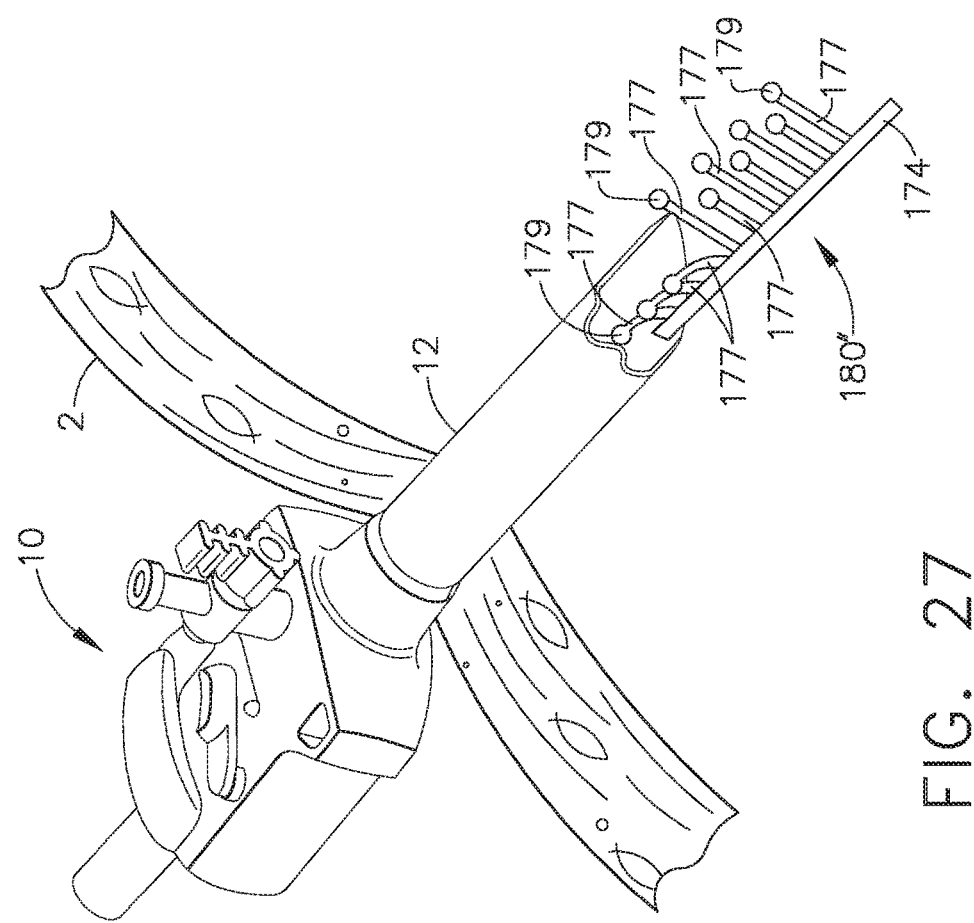
FIG. 27 is a perspective view of a trocar device inserted through the abdominal wall of a patient with a bowel retractor device embodiment being passed through the trocar cannula.

FIG. 24 illustrates a bowel retractor device 170' that is substantially identical in construction and use as bowel retractor device 170 except that device 170' only has fingers 177 that all have a common length. FIG. 25 illustrates a bowel retractor device 180 that is substantially identical in construction and use as bowel retractor device 170', except that fingers 177 protrude out of the inner area 176. In particular, the endless collar 174 defines a reference plane "RP" and each of the fingers 177 extend transversely to reference plane RP. The bowel retractor device embodiment 180 depicted in FIG. 25 is substantially identical to bowel retractor device 170', except that fingers 177 all taper away from the endless collar 174 in a general frusto-conical configuration. That is, each of the fingers 177 extend along an axes that will ultimately intersect at a common point. The bowel retractor device 180' in FIG. 26 is substantially identical in construction and use as bowel retractor device 180 except that the fingers 177 extend out of the open area such that they are substantially perpendicular to the reference plane RP and are substantially parallel to each other. The bowel retractor device 180" in FIG. 27 is substantially identical to the bowel retractor device 180' except that the fingers 177 have different lengths. The bowel retractor devices 170', 180, 180', 180" may all be used in the various manners described above.

Figure 28:
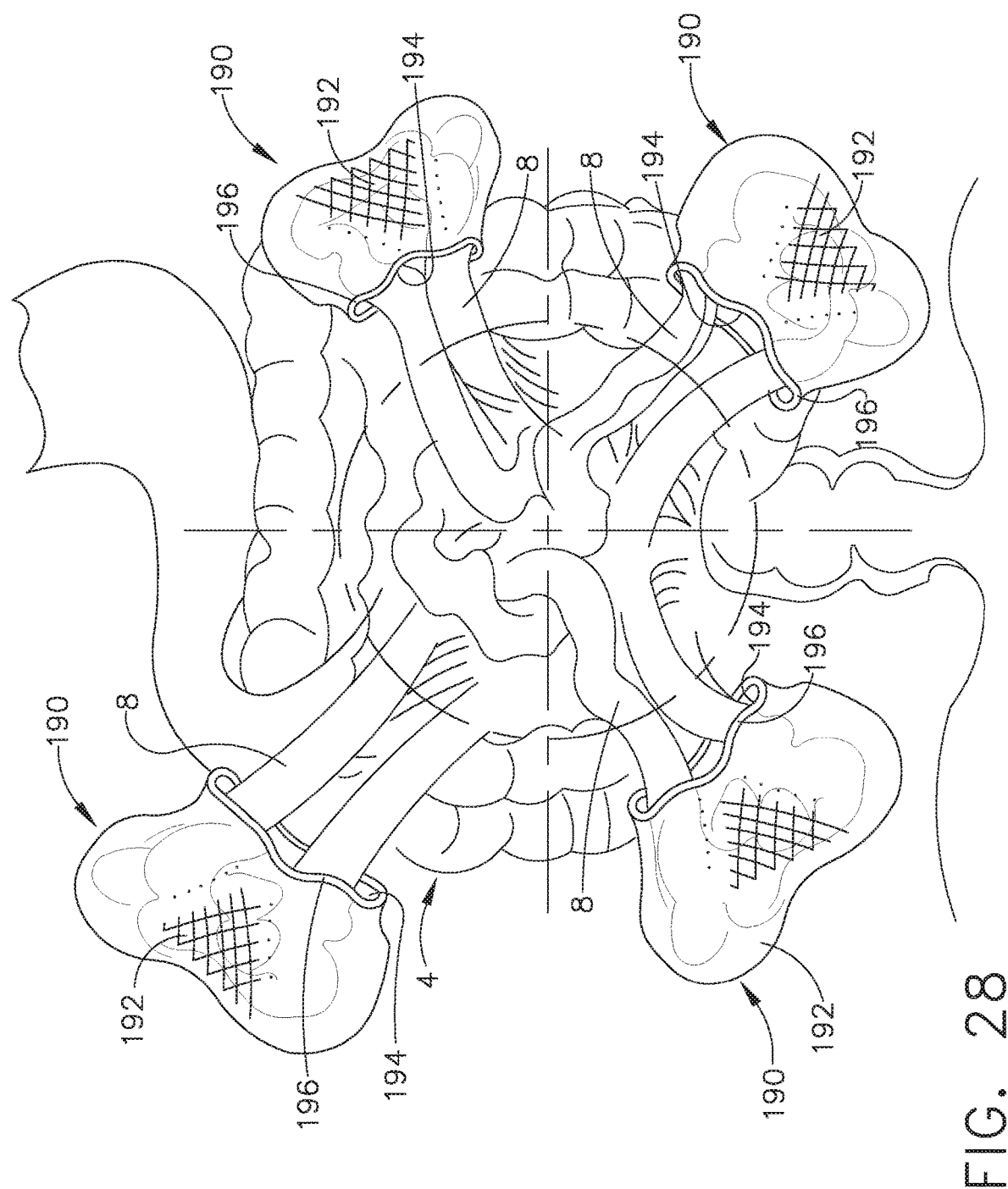
FIG. 28 is a perspective view of a portion of a patient's colon with four bowel retractor device embodiments of the present invention supporting non-target bowel portions.

FIG. 28 illustrates the use of four bowel retractor devices 190 for supporting the non-target bowel portions 8 in each of four quadrants involved in the surgical procedure. In at least one embodiment, each bowel retractor device 190 comprises a flexible pouch 192 that has an opening 194 therein. In one embodiment, the opening is surrounded by a collar member 196 in the form of an elastic band. The pouches 192 may be rolled up into a first collapsed position to enable them to be inserted through a trocar cannula 12. Once the pouches 192 have been inserted into the surgical area, the surgeon may open each pouch 192 and install it over a portion of non-target bowel 8. Once the pouches have been installed over the various non-target bowel portion(s) 8, they may be separated into quadrants which provide the surgeon with physical and visual access to the target bowel portion. Those of ordinary skill of the art will understand that various numbers of pouches 192 may be employed as needed.

Figure 29:
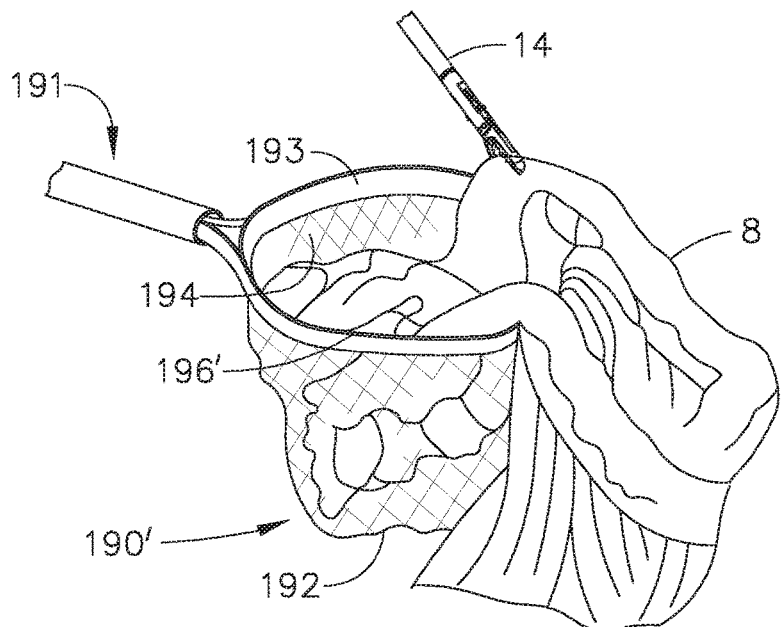
FIG. 29 is a partial perspective view of another bowel retractor device embodiment of the present invention being supported in an expanded position by an installation tool embodiment of the present invention.
Figure 30:
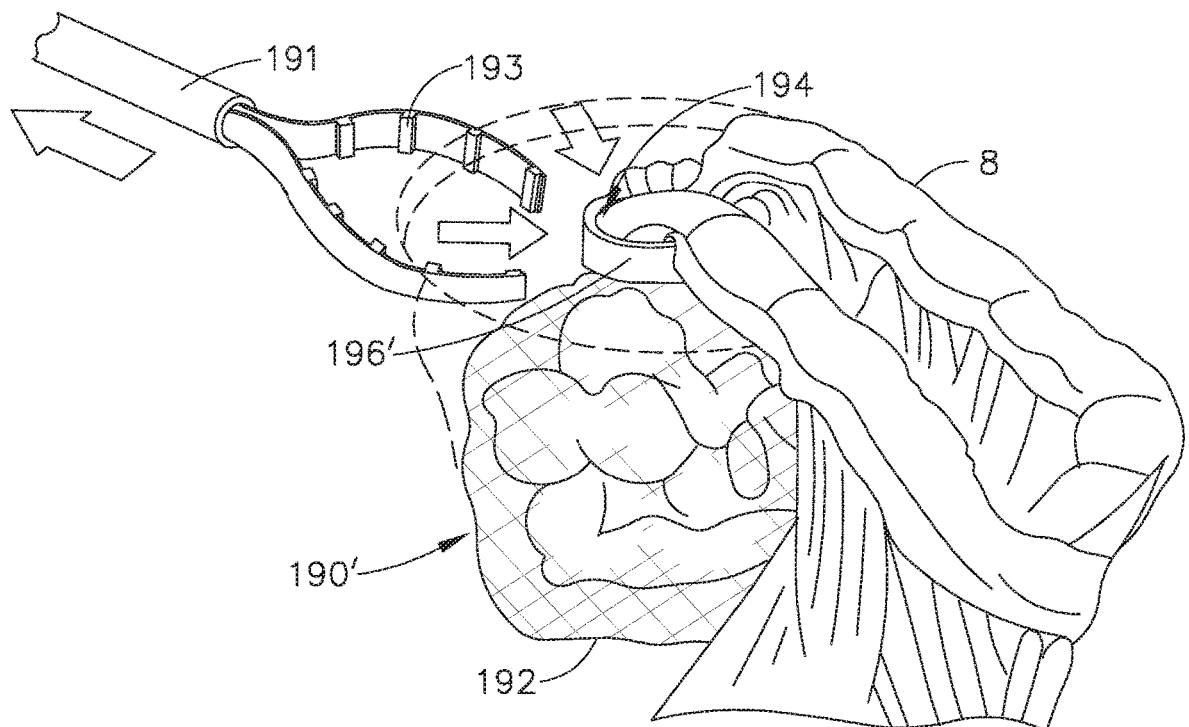
FIG. 30 is another perspective view of the bowel retractor device embodiment of FIG. 29 supporting a bowel portion therein with the installation tool removed therefrom.

FIGS. 29 and 30 illustrate another bowel retractor device 190' that is substantially identical to bowel retractor device 190, except that the collar member comprises an elastic band 196' that may be expanded from a non-expanded or collapsed state to an expanded state by inserting a selectively expandable and contractible installation head 193 of an installation tool 191 into the opening 194. When the installation head 193 is expanded, the elastic collar or band 196' is retained in the expanded state to permit the non-target bowel portions 8 to be inserted into the pouch 192 through the opening 194. Once the non-target bowel portion 8 has been inserted into the pouch, the installation head 193 is moved to the contracted position and removed from the elastic collar 196' which lightly contracts around the non-target bowel portions 8 protruding through the opening 194 to retain the non-target bowel portion 8 within the pouch 192 without damaging the non-target bowel portion 8 protruding therefrom.

The bowel retractor device 190" in FIG. 31 is substantially identical in construction and use as bowel retractor device 190 except that the collar 196" is a cinchable member. For example, the collar 196" may comprise an expandable belt-type member that may be expanded to form a desired opening and then locked in position by a lock screw 197. Thus, the surgeon may release the lock screw 197 to enable the opening to be expanded for installation over a portion of the non-target bowel portion 8 and thereafter cinched in and locked with locking screw 197 to retain the pouch 192 on the non-target bowel portion 8 captured therein.

Figure 36:
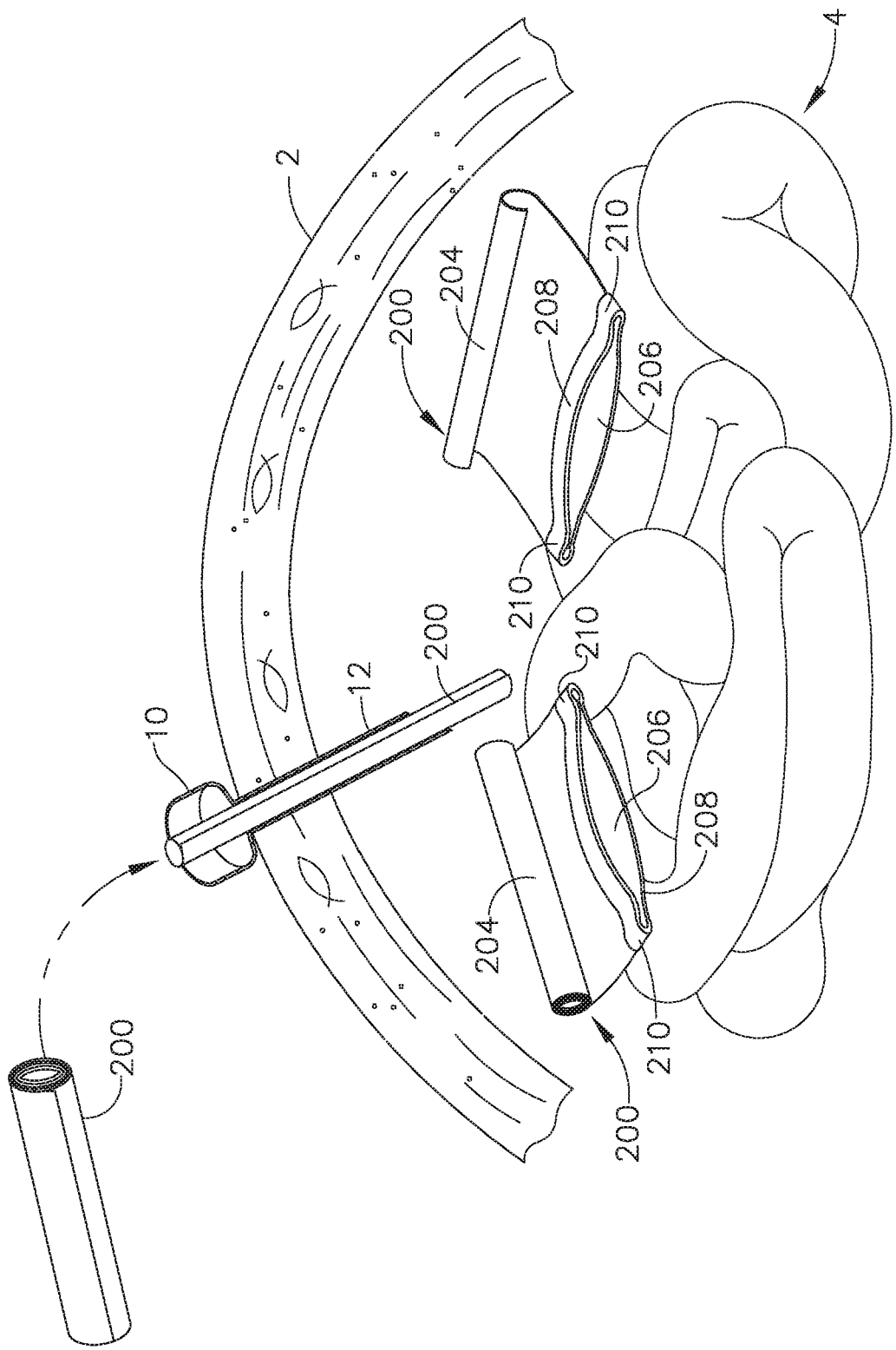
FIG. 36 is a perspective view of three bowel retractor device embodiments of FIGS. 32-35 inside a portion of a patient's abdomen.
Figure 37:
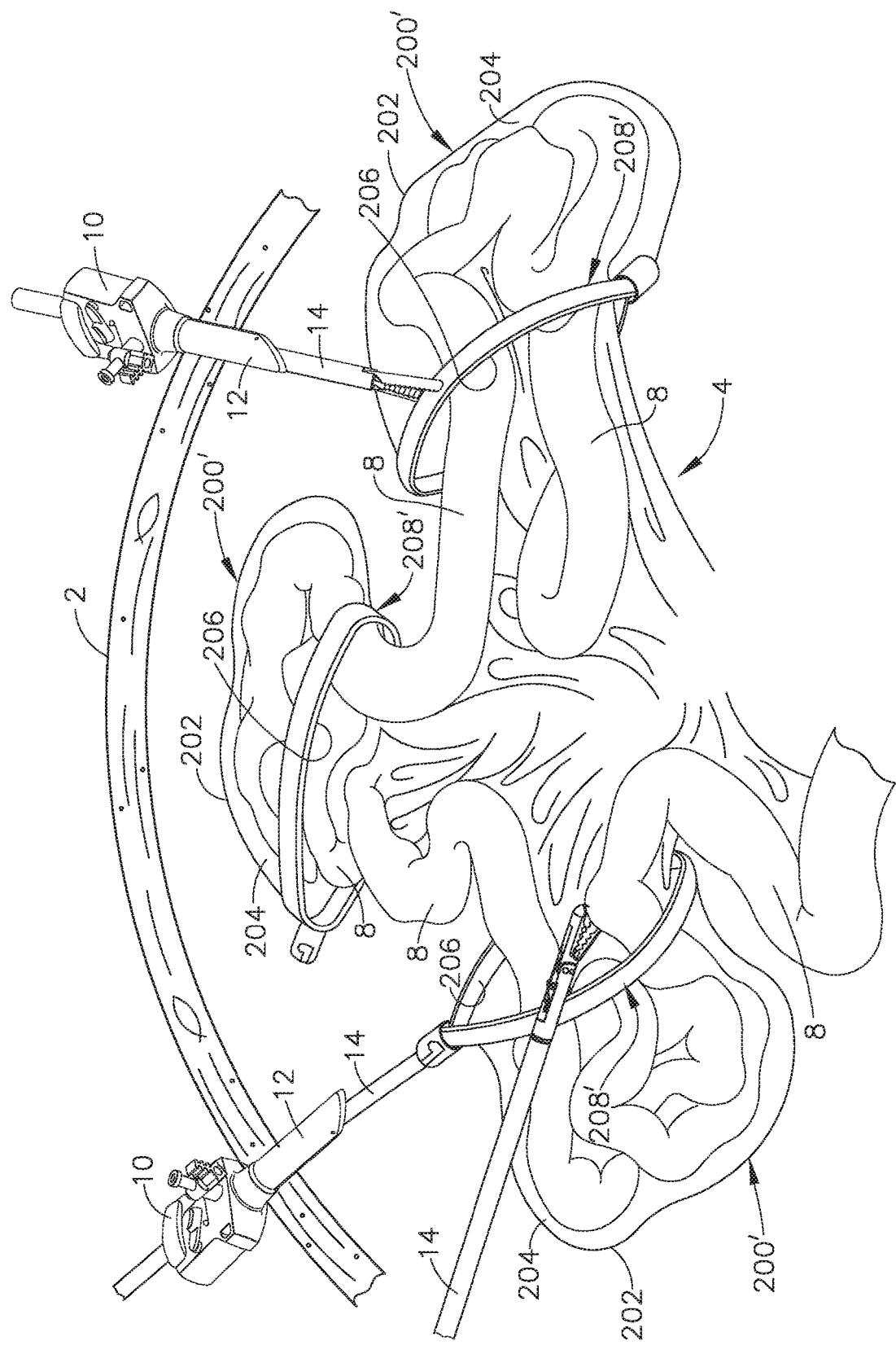
FIG. 37 is a perspective view of a patient's abdomen and bowel retractor device embodiments of the present invention supporting portions of the patient's bowel therein.
Figure 38:
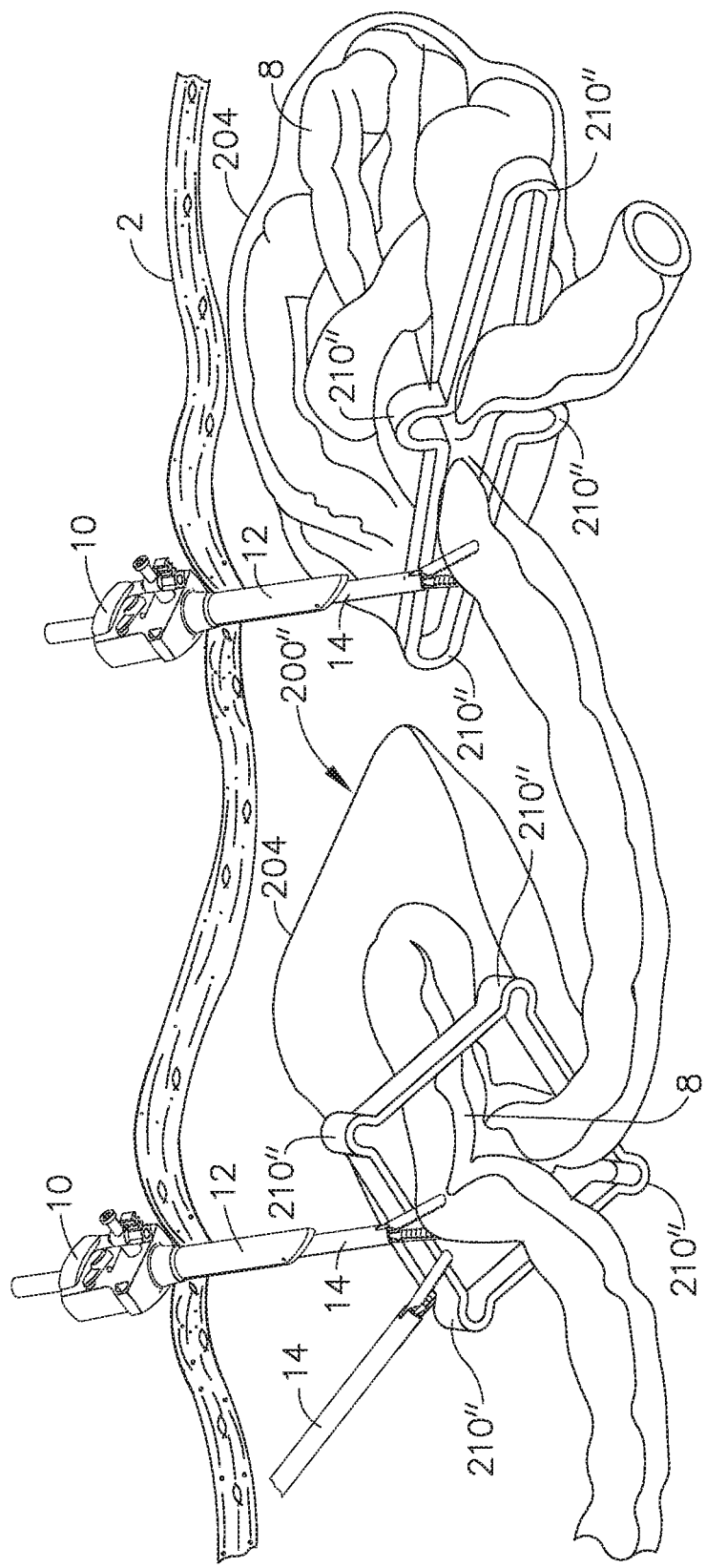
FIG. 38 is a perspective view of a patient's abdomen and bowel retractor device embodiments of the present invention supporting portions of the patient's bowel therein.
Figure 39:
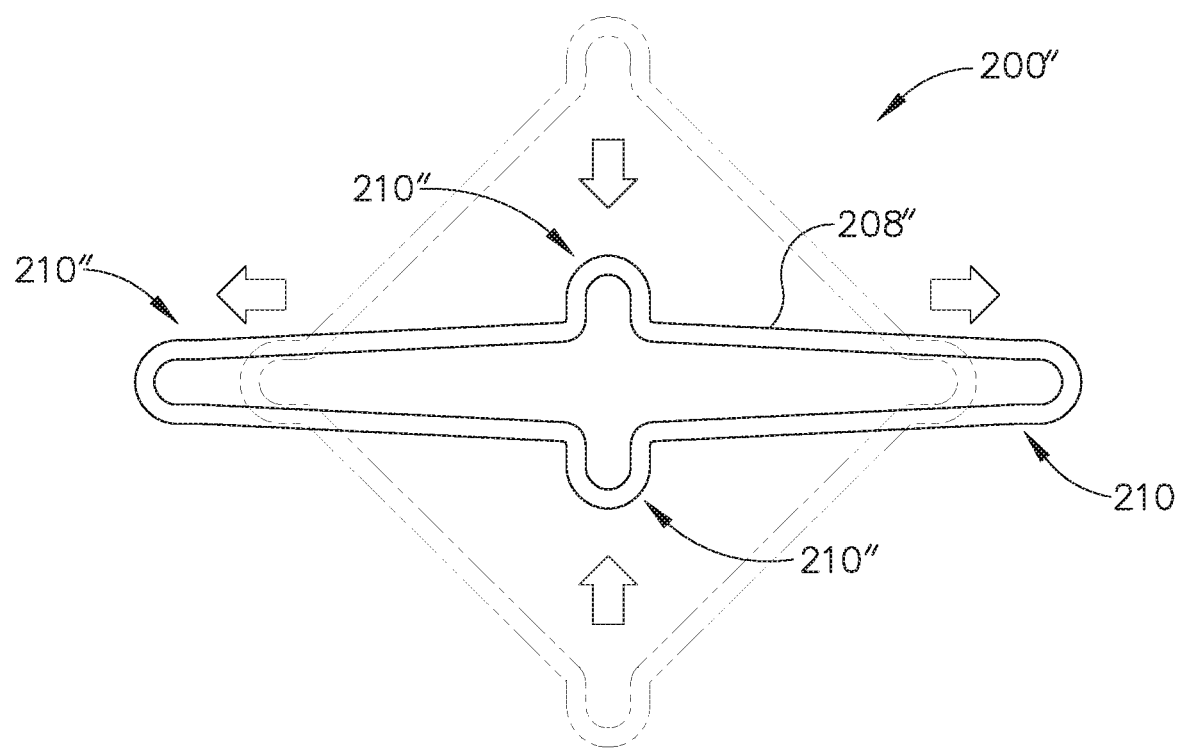
FIG. 39 is a top view of one of the bowel retractor devices depicted in FIG. 38 in a closed position.
Figure 40:
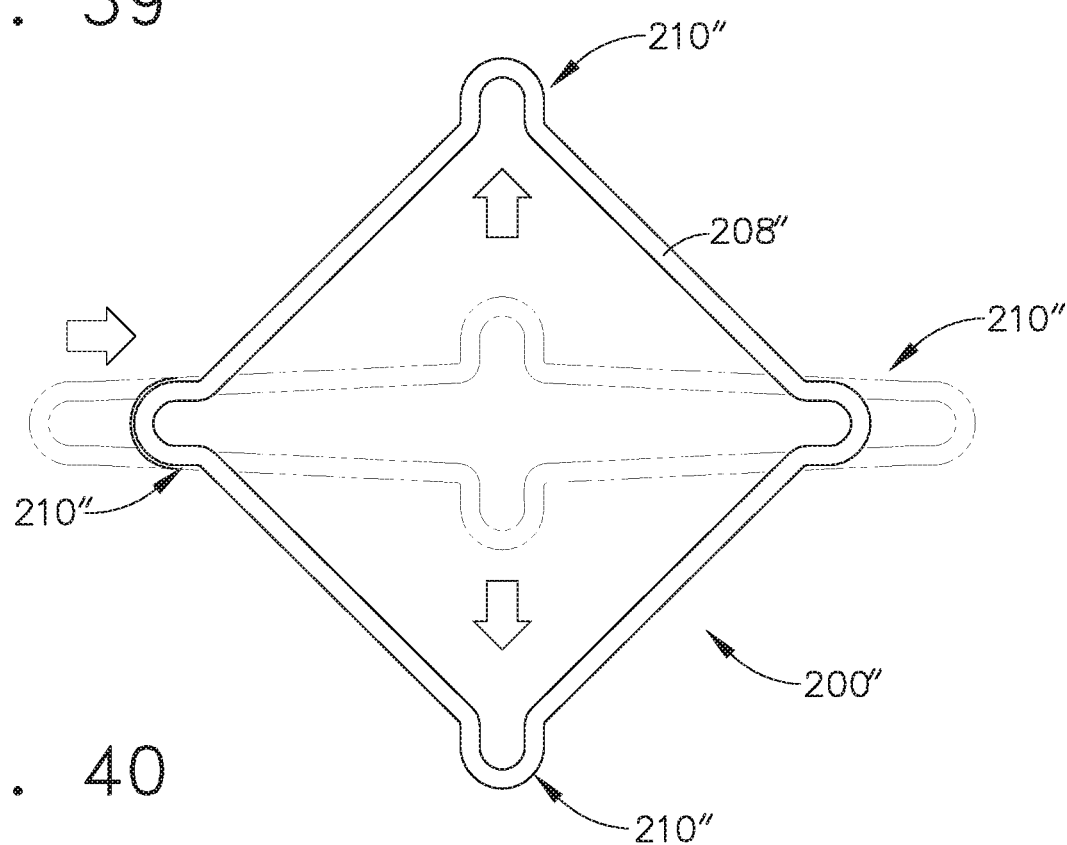
FIG. 40 is another top view of the bowel retractor device of FIGS. 38 and 39 in an open position.
Figure 45:
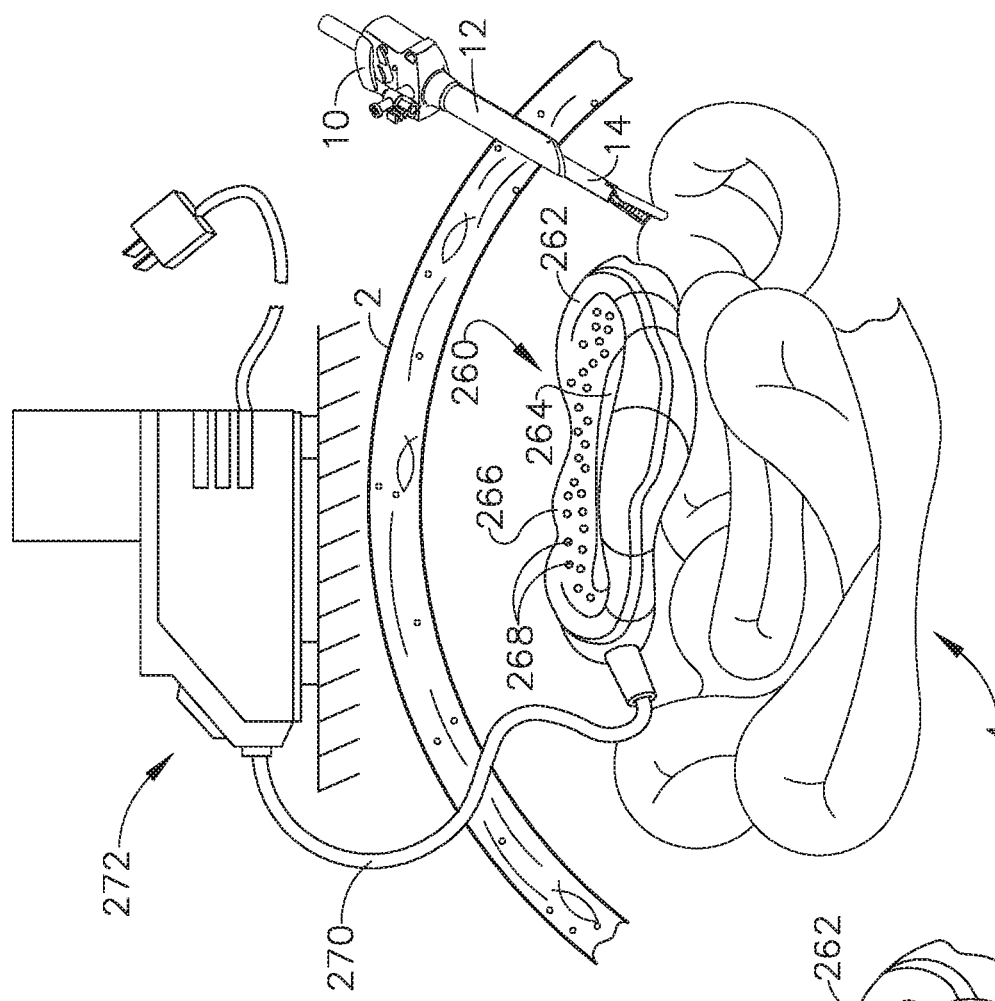
FIG. 45 is a partial perspective view of a portion of a patient's abdomen supporting the bowel retractor device embodiment of FIG. 43 therein in an uninflated state.
Figure 43:
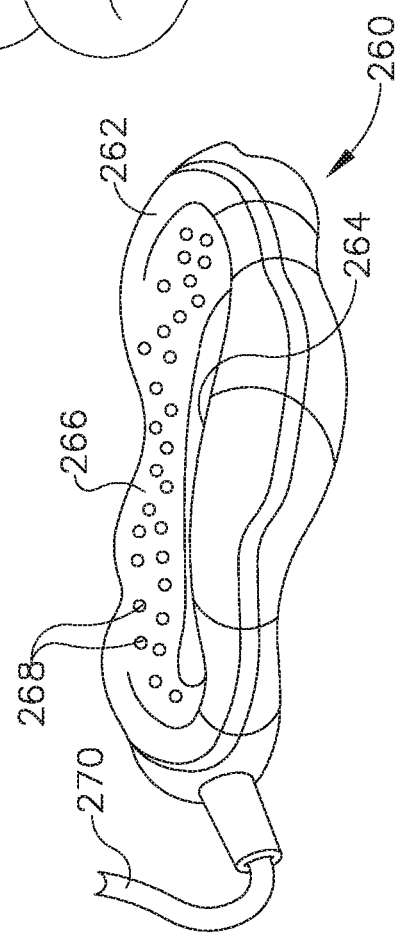
FIG. 43 is a perspective view of a portion of another bowel retractor device embodiment of the present invention in an uninflated state.

FIGS. 32-36 illustrate another form of bowel retractor device 200 embodiment of the present invention. In various forms, the bowel retractor device 200 comprises a body portion 202 in the form of a pouch 204. In various embodiments, the pouch 204 may have a cinchable opening 206 therein. In at least one embodiment, a closure member 208 is attached to the pouch 204 such that it extends around the opening 206. The closure member 208 may be configured with two diametrically opposed hinge portions 210 that facilitates movement of the closure member 208 from a collapsed or closed position (FIG. 33) to an open position (FIG. 32). As illustrated in FIG. 32, the closure member 208 may be moved to the open position by applying opposing forces "F1" on the hinge portions 210 as well as applying opening forces "F2" in opposite directions to the closure member 208. The bowel retractor device 200 may be inserted into the patient through a trocar 10 as shown in FIG. 34. To facilitate insertion of the retractor device 200 through the trocar cannula 12, the device 200 may be rolled up as shown in FIGS. 34-36. FIG. 37 illustrates another bowel retractor device 200' that is substantially identical in construction and use as bowel retractor device 200 except that the closure member 208' is substantially spring-loaded. Such spring loading may be created by the configuration of the closure member itself or be assisted with one or more spring members (not shown) embedded therein. FIGS. 38-40 illustrate another bowel retractor embodiment 200" that is essentially the same as the bowel retractor 200, except that the closure member 208" has four hinge portions 210".

The closure members 208, 208', 208" of the bowel retractor devices 200, 200', 210", respectively are designed in their normal state to be biased to a closed position or state. When in the closed state, however, the closure members 208, 208', 208" may be designed to limit the closure force exerted onto the portion of the bowel received therein to minimize the risk of occlusion of blood flow to the captured bowel portion as well as to allow peristalsis to continue. Such closure bias is designed to immediately immobilize the non-target portions 8 of the bowel placed in the pouch so that it does not slip back out. The hinge portions 210, 210', 210" enable the closure members 208, 208', 210" to be forced open for the entire loading period, or more preferably, the closure member could be opened only as bowel segments are pulled in. The closure portions then maintain the opening in a closed position while the surgeon moves to grasp the next section of bowel to be introduced into the pouch. Thus, use of the biased closed temporary bowel retractor devices 200, 200', 200" improve the ease of introducing bowel portions therein as the closure portions thereof can automatically close itself to keep the non-target bowel portion from slipping back out of the pouch. The maximum cinching load also prevents inadvertent damage to the non-target bowel during retraction. In use, the surgeon may insert several of the devices 200, 200', and/or 200" through a trocar, trocars or other openings in the patient at the beginning of the surgical procedure. Lengths of the non-target bowel portions 8 would be placed into a pouch and then when the pouch became sufficiently full, the closure member thereof would be "snapped" shut. This procedure may be repeated with other bowel retractor devices 200, 200', 200" as needed. These loaded pouches could then be easily moved from one position to another in the abdomen cavity during the procedure. The surgeon is able to easily grasp and move en masse sections of the bowel 4 to move it out of the way. Additionally, the pouches could be temporarily clipped or pinned to different abdomen wall structures to facilitate more retraction. Also, the various pouch-type bowel retractor devices disclosed above may include a grasper access hole through the bottom of the pouch to enable a grasper instrument to be inserted therethrough and out through the pouch opening to grasp bowel portions to draw them into the pouch. Such arrangement serves to facilitate easy introduction of the bowel portions into the pouch. The hinge arrangements also serve to bias the closure members closed around the bowel portions as they are drawn into the pouch.

FIGS. 41 and 42 illustrate another bowel retractor device embodiment 220 of the present invention. Various embodiments include a substantially elastic body portion 222 that is insertable through an opening in a patient's body to a second expanded position wherein a portion of the patient's bowel may be supported thereby. In various embodiments, the body portion 222 includes a central portion 224 that has at least three flexible first arms 226 that protrude from the central portion 224 in a first direction. A first opening 228 is formed between each first arm 226. In at least one embodiment, each first opening has a shape that generally resembles a portion of an hourglass. In particular, each first opening 228 has a first neck portion 229 that is narrower than a first bottom portion 230. As can be further seen in FIGS. 41 and 42, the bowel retractor device 220 further comprises at least two flexible second arms 240 that protrude from a second side of the central portion 224 in a second direction. In one embodiment, each second arm 240 protrudes from the center portion 224 at positions opposite to the first opening 228. In other embodiments, the second arms 240 may be aligned with corresponding first arms 226. A second opening 242 is formed between each second arm 240. In at least one embodiment, each second opening 242 has a shape that generally resembles a portion of an hourglass. In particular, each second opening 242 has a second neck portion 244 that is narrower than a second bottom portion 246. In other embodiments, the first and second openings may be provided in other shapes.

Various embodiments of the bowel retractor device 220 are fabricated from a foam material or other elastic material. In other embodiments, each of the first and second arms 226, 240 have a bendable wire member or wire members (nitinal, spring steel, etc.) embedded therein to enable the arms 226, 240 to be advantageously bent in position to facilitate insertion of the retractor device 220 through a trocar or other opening. In still other embodiments, the center portion 224 may have a bendable wire portion therein. In other arrangements, bendable wires may be embedded in the center portion 224 and each of the first and second arms 226, 240. In other embodiments, at least one bendable wire is embedded in at least one of the center portion 224, a first arm 226 and/or a second arm 240. Such arrangements facilitate the bending of the device 220 in a position that facilitates its insertion through a trocar cannula. In other embodiments, however, the device 220 may be sized such that it can pass through a trocar cannula without having to be bent or collapsed.

In use, once the bowel retractor device 220 has been inserted into the patient through a trocar or other opening in the patient's body, the surgeon may grasp the retractor 220 with a grasping instrument and then pull non-target bowel portions 8 through the first and/or second openings 228, 242. The bowel portions 8 may be held in place by manipulating the formable arms 226, 240. In various embodiments, a suture drawstring 250 (FIG. 42) is provided to further support and tie down the retractors position. This step could be repeated several times creating a grouped clump of small bowel that can be moved around merely by moving the bowel retractor 220. Various embodiments of the retractor 220 can be bent into whatever restraining form would be most useful to keep the clump out of the working space. It could be lodged up behind a trocar cannula 12 or held back with a grasping instrument 14, whatever is convenient for the specific case. The flexible fit holds the small bowel together without strangulating it or interfering with the peristalsis causing swelling. The fit is tight enough to prevent the bowel from slipping right back out.

FIGS. 43-46 illustrate another bowel retractor device embodiment 260 of the present invention. In various embodiments, the retractor 260 comprises an inflatable ring 262 that defines an interior area 264. The inwardly facing surface 266 of the inflatable ring 262 is textured with, for example, dimples 269, etc. The ring 262 is supplied with a pressurized medium such as, for example, through a supply conduit 270 that is attached to a source of pressurized medium 272 located outside of the patient's body. See FIG. 45.

Figure 46:
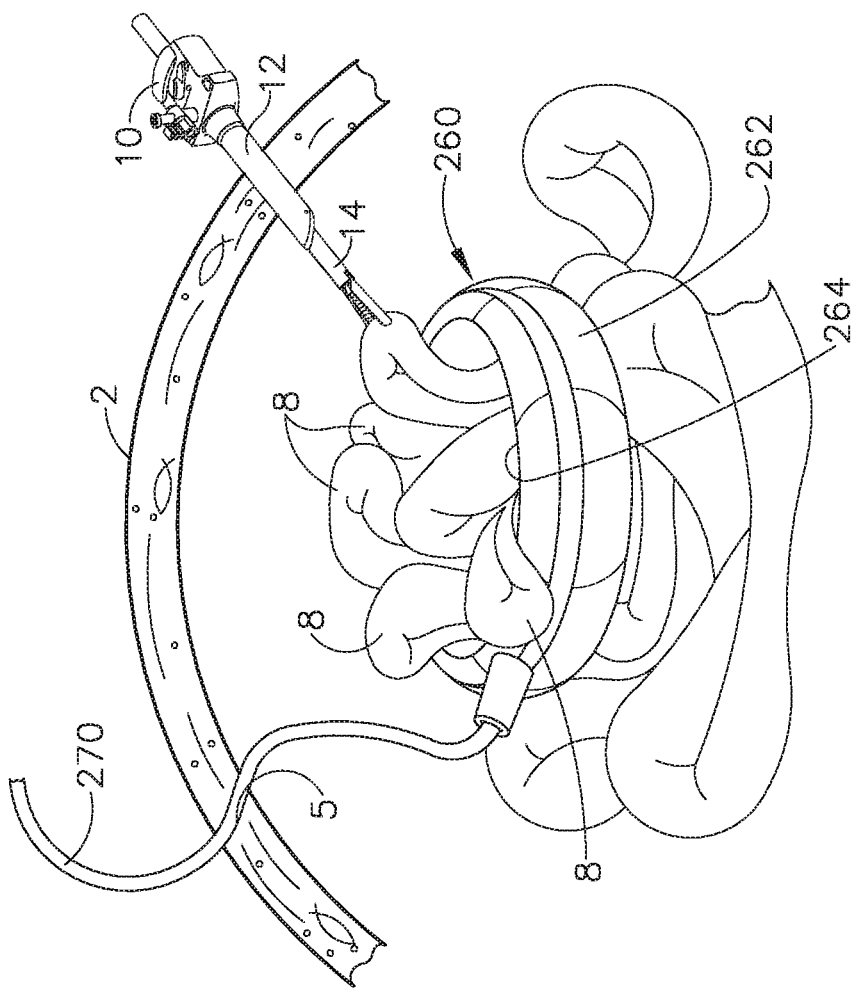
FIG. 46 is another partial perspective view of a portion of a patient's abdomen containing the bowel retractor device embodiment of FIG. 44 therein and supporting a portion of the patient's bowel therein.
Figure 44:
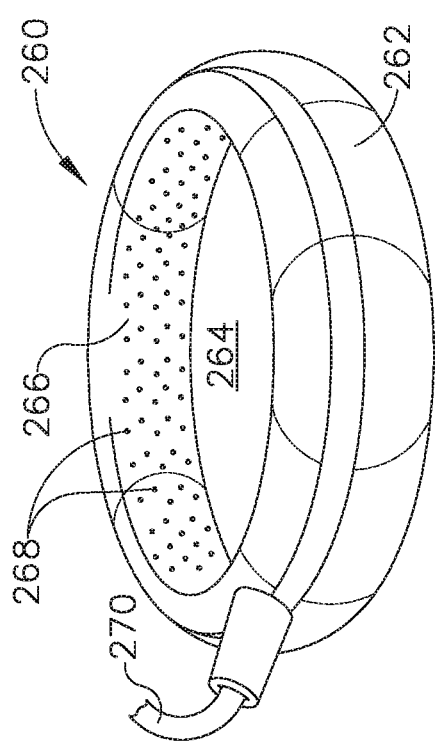
FIG. 44 is another perspective view of the portion of bowel retractor device embodiment of FIG. 43 in an inflated state.

To use the bowel retractor device 260, the retractor 262 (in its collapsed or uninflated state) as well as the supply conduit may be inserted through a trocar 10 mounted in the abdominal wall 2 or it may be inserted into the surgical site through another opening 5 in the abdominal wall 2 as shown in FIG. 46. Once in position, the surgeon may then grasp non-target bowel portions 8 with one or more grasping instruments 14 to pull the non-target bowel portions 8 through the interior area 264. The surgeon may first inflate the ring 262 prior to pulling the non-target bowel portions 8 through the interior area 264 or the surgeon may pull the non-target bowel portions 8 through the interior area 264 prior to inflating the ring 262. Once inflated, the textured surface 266 retains the bowel portions in position. One or more retractors 260 may be used in the various methods described above to advantageously provide the surgeon with physical and visual access to the target tissue during the operation.

The various bowel retraction devices disclosed herein represent vast improvements over other retraction devices and methods commonly employed with performing operations on a patient's bowel. Many embodiments may be easily inserted into the patient through a common trocar cannula. The devices are easily manipulatable with common grasping instruments. Several of such devices may be used as necessary to advantageously locate non-target portion(s) of bowel in a desired position to provide the surgeon with physical and visual access to the target tissue. Once bunches of bowel have been gathered together, the bunches may be easily moved and positioned en masse to a desired location. The retractors may be easily clipped to portions of the abdomen to hold the retractor in position if necessary. While the various retractor devices disclosed herein have been described in detail for use in connection with bowel surgeries, it is conceivable that various embodiments of the present invention could also be employed to retract other forms of tissue/organs without departing from the spirit and scope of the present invention.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A bowel retractor device, comprising:
    an elongated flexible endless collar member comprising an inner wall that defines a central open area;
    a plurality of discrete first flexible fingers protruding inwardly from a first portion of said inner wall into said central open area, wherein each said discrete first flexible finger comprises a first end, wherein said first ends are spaced from each other to define a first space therebetween, and wherein each said first end comprises a first ball-shaped member formed thereon; and
    a plurality of discrete second flexible fingers protruding from a second portion of said inner wall that faces said first portion of said inner wall, wherein each said discrete second flexible finger comprises a second end, wherein said second ends define a second space therebetween, wherein each said second end extends into a corresponding said first space, wherein each said first end extends into a corresponding said second space, and wherein each said second end comprises a second ball-shaped member formed thereon.

2. The bowel retractor device of claim 1, wherein each said first ball-shaped member comprises a first diameter, and wherein each said second ball-shaped member comprises a second diameter that differs from said first diameter.

3. The bowel retractor device of claim 1, further comprising at least one manipulation formation on said elongated flexible endless collar member.

4. The bowel retractor device of claim 3, wherein said elongated flexible endless collar member comprises an external surface, and wherein said at least one manipulation formation protrudes from said external surface.

5. The bowel retractor device of claim 1, wherein said central open area is elongated and comprises:
   a first open area end portion that has a first width; and
   a second open area end portion that has a second width that differs from said first width.

6. A bowel retractor device, comprising:
   an elongated flexible endless collar member comprising an inner wall that defines an elongated central open area, wherein said elongated central open area comprises:
      a first open area end portion, wherein said first open area end portion comprises a first width; and
      a second open area end portion, wherein said second open area end portion comprises a second width that differs from said first width, and wherein said bowel retractor device further comprises:
   a plurality of discrete first flexible fingers protruding inwardly from a first portion of said inner wall into said elongated central open area, wherein each said discrete first flexible finger comprises a first end, wherein said first ends are spaced from each other to define a first space therebetween; and
   a plurality of discrete second flexible fingers protruding from a second portion of said inner wall that faces said first portion of said inner wall, wherein each said discrete second flexible finger comprises a second end, wherein said second ends define a second space therebetween, wherein each said second end extends into a corresponding said first space, wherein each said first end extends into a corresponding said second space.

7. The bowel retractor device of claim 6, further comprising at least one manipulation formation on said endless collar member.

8. The bowel retractor device of claim 7, wherein said elongated flexible endless collar member comprises an external surface, and wherein said at least one manipulation formation protrudes from said external surface.

9. A bowel retractor device, comprising:
   a flexible endless collar member comprising an inner wall that defines a central open area; and
   a plurality of discrete first flexible fingers protruding from a first portion of said inner wall, wherein said discrete first flexible fingers are spaced from each other to define a first space therebetween; and
   a plurality of discrete second flexible fingers protruding from a second portion of said inner wall that faces said first portion of said inner wall, wherein each said discrete second flexible finger comprises a second end that extends into a corresponding said first space, and wherein at least one of said discrete first flexible fingers and at least one of said discrete second flexible fingers each comprise a ball-shaped feature formed on an end thereof.

10. The bowel retractor device of claim 9, wherein each said discrete first flexible finger comprises a first diameter, and wherein each said discrete second flexible finger comprises a second diameter that differs from said first diameter.

11. The bowel retractor device of claim 10, wherein said second diameter is greater than said first diameter.

12. The bowel retractor device of claim 9, wherein said discrete second flexible fingers are spaced from each other to define a second space therebetween, and wherein each said discrete first flexible finger comprises a first end that extends into a corresponding second space.

13. The bowel retractor device of claim 9, further comprising at least one manipulation formation on said flexible endless collar member.

14. The bowel retractor device of claim 13, wherein said flexible endless collar member comprises an external surface, and wherein said at least one manipulation formation protrudes from said external surface.

\* \* \* \* \*